(12) United States Patent
Cui et al.

(10) Patent No.: US 7,038,107 B2
(45) Date of Patent: May 2, 2006

(54) ELIMINATION OF ENDOGENOUS PORCINE RETROVIRUS

(75) Inventors: Cunqi Cui, Plainsboro, NJ (US); Lisa E. Diamond, Princeton, NJ (US); John S. Logan, Robbinsville, NJ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 120 days.

(21) Appl. No.: 10/113,664

(22) Filed: Mar. 28, 2002

(65) Prior Publication Data

US 2003/0224350 A1  Dec. 4, 2003

Related U.S. Application Data

(60) Provisional application No. 60/279,337, filed on Mar. 28, 2001.

(51) Int. Cl.
 *A01K 67/033* (2006.01)
 *A01K 67/027* (2006.01)
 *C12N 15/00* (2006.01)

(52) U.S. Cl. ............... 800/17; 800/8; 800/9; 800/14; 800/21

(58) Field of Classification Search ............ 800/8, 800/9, 14, 17
 See application file for complete search history.

(56) References Cited

U.S. PATENT DOCUMENTS

| | | | |
|---|---|---|---|
| 6,100,034 A * | 8/2000 | Stoye et al. ............ | 435/6 |
| 6,190,861 B1 * | 2/2001 | Fishman ................ | 435/5 |
| 6,261,806 B1 | 7/2001 | Banerjee et al. | |
| 6,867,347 B1 * | 3/2005 | Patience ............... | 800/8 |

FOREIGN PATENT DOCUMENTS

WO WO 00/73512 A1 12/2000

OTHER PUBLICATIONS

Magre et al. "Xenotransplantation and pig endogenous retroviruses," Rev Med Virol 13:311-329, 2003.*
Wilson et al. "Extended analysis of the in vitro tropism of porcine endogenous retrovirus," J Virol 74(1): 49-56, 2000.*
Mang et al, J Gen Virol 2001;82:1829-34.*
Patience et al, J Virol 2001;2771-5.*
Gorbovitskaia et al, Immunogenitics 2003;55:262-70.*
Zhang et al, Transplant Proc. 2004;36;2495-7.*
Jin et al, Transpl Infect Dis 2000;2:11-14.*
Deng et al, Nucleic acids Res Dec. 2000;28;28(e103):1-4.*
Herring et al, J. Virol 2001;75;12252-65.*
Akiyoshi et al., "Identification of a Full-Length cDNA for an Endogenous Retrovirus of Miniature Swine", *Journal of Virology* 72:5: 4503-4507 (1998).
Bosch et al., "Study of Full-Length Porcine Endogenous Retrovirus Genomes with Envelope Gene Polymorphism in a Specific-Pathogen-Free Large White Swine Herd", *Journal of Virology* 74:18: 8575-8581 (2000).
Czaudema et al., "Establishment and Characterization of Molecular Clones of Porcine Endogenous Retroviruses Replicating on Human Cells", *Journal of Virology* 74:9: 40248-4038 (2000).
C. Cui, et al., "Evidence of High Frequency of Allelic Polymorphism in Potentially Infectious PERV Loci from a Transgenic Pig Herd," Xenotransplantation 8(Supp. 1):16, 2001.
Database EMBL, "Sus Scrofa Back Fat mRNA; Expressed Sequence Tag (5'; cDNA clone PT7F9)," 1999 (Abstract).
Database EMBL, "298293 MARC 1PIG Sus Scrofa cDNA 5', mRNA Sequence," 2001 (Abstract).
U. Krach, et al., "Howe Many Functional PERVs Exist in Pigs?," Xenotransplantation 8(Supp. 1): 16, 2001.

* cited by examiner

*Primary Examiner*—Q. Janice Li
(74) *Attorney, Agent, or Firm*—Quarles & Brady LLP

(57) ABSTRACT

Porcine nucleic acid sequences flanking potentially infectious porcine endogenous retroviral (PERV) insertion sites have been identified and isolated. The unique flanking sequences include porcine nucleic acid sequences that flank the 3' end and porcine nucleic acid sequences that flank the 5' end of PERV insertion sites. The present invention provides compositions and methods for detecting presence of PERV in a sample, particularly those with infectious potential. In addition, the invention relates to breeding of pigs or selection of porcine tissue that is free of infectious PERV for use as a xenotransplant tissue.

4 Claims, 22 Drawing Sheets

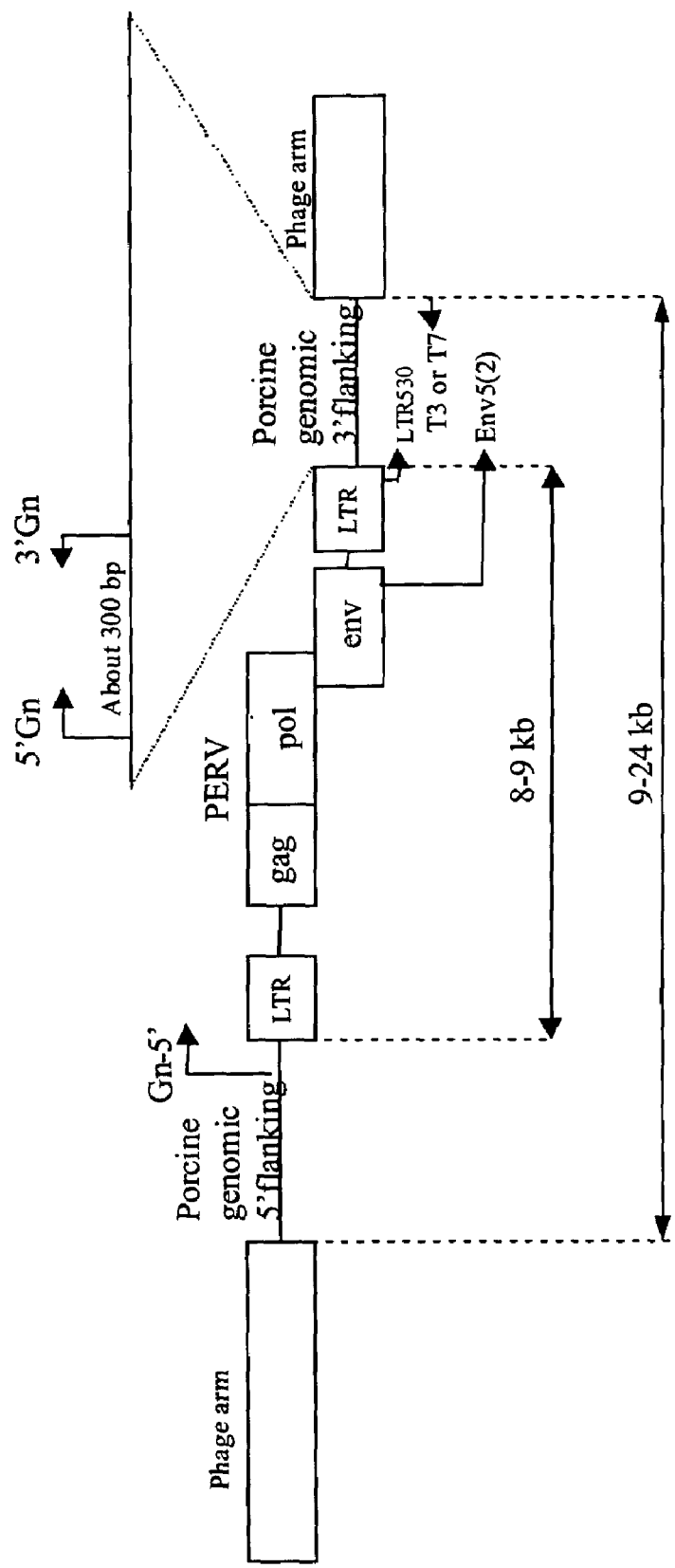
Figure 2. Map of a vector with PERV insert

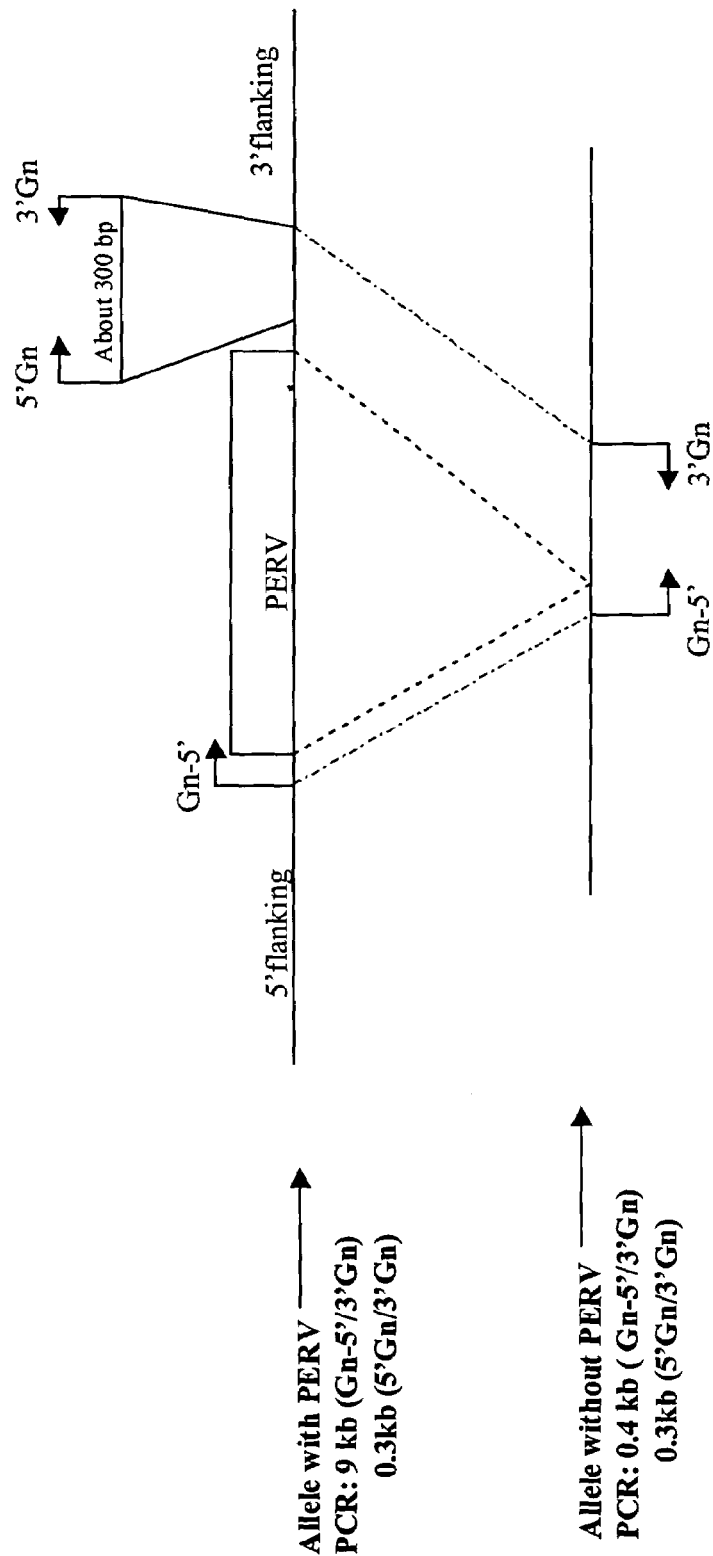
Figure 3. Identification of Allele polymorphism of PERV locus by PCR analysis

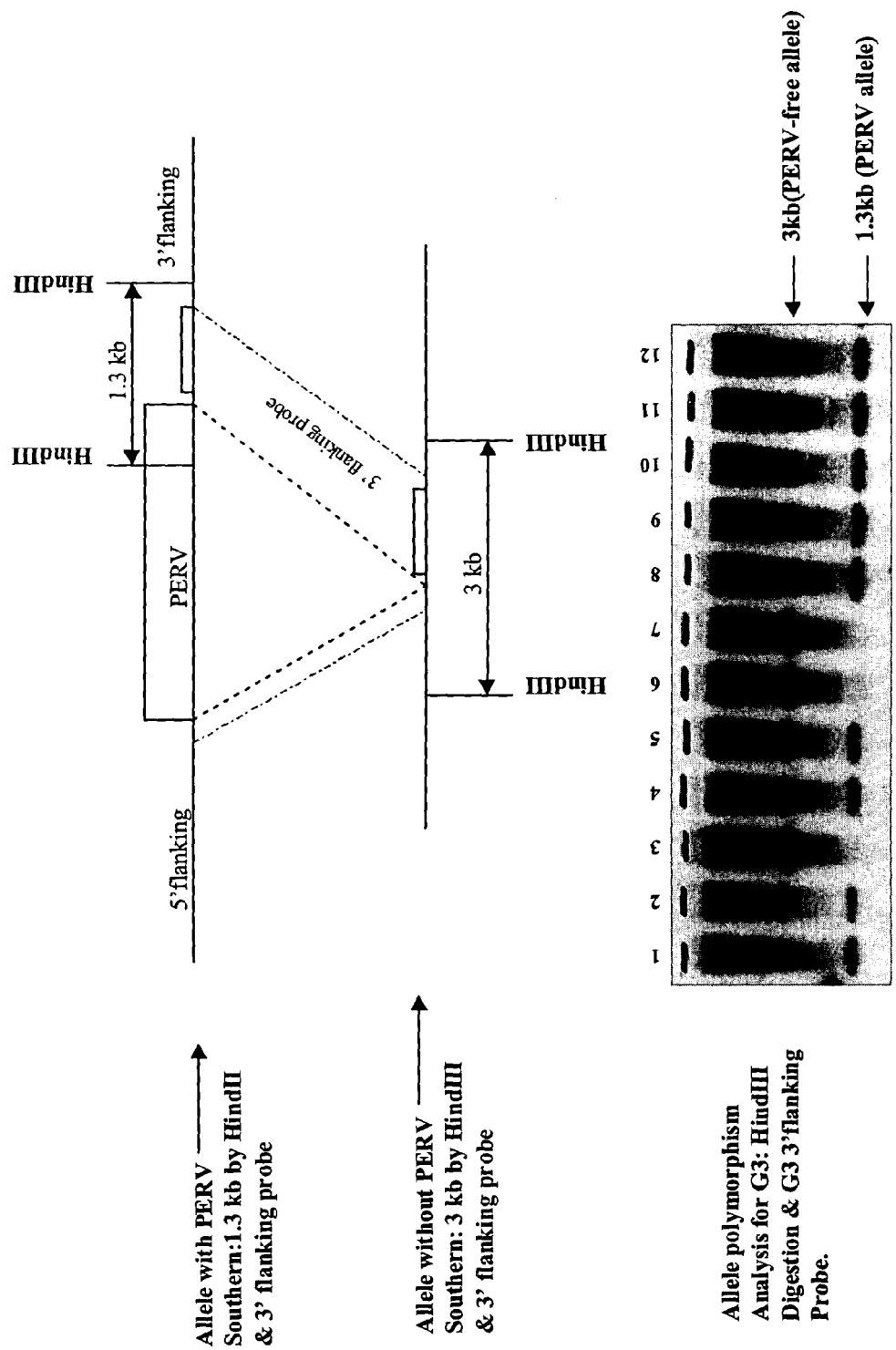
Figure 4. Identification of allele polymorphism of PERV locus by Southern analysis

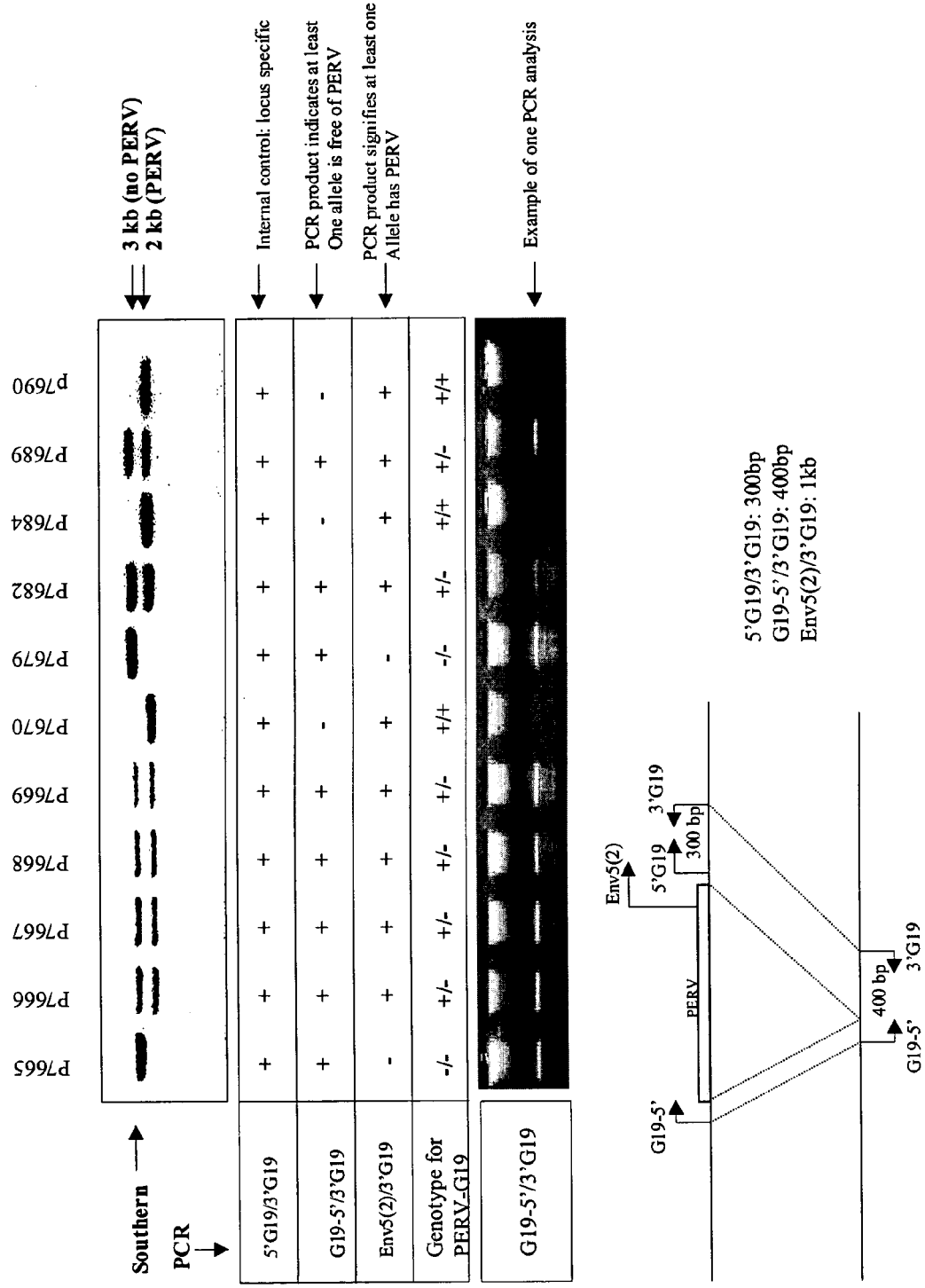
Figure 5. Identification of allele polymorphism analysis of G19 locus by PCR analysis

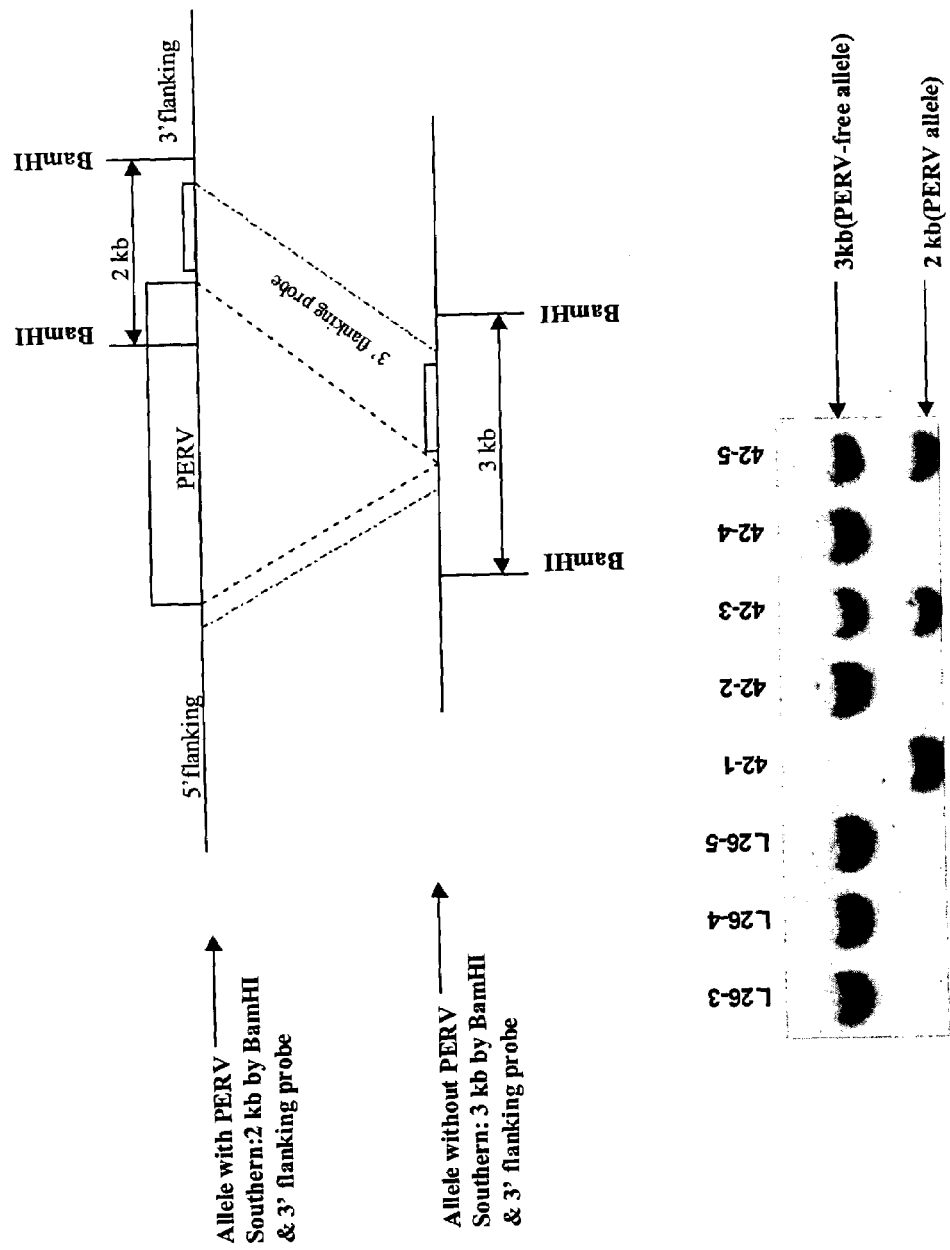
Figure 6. Identification of allele polymorphism of PERV locus G19

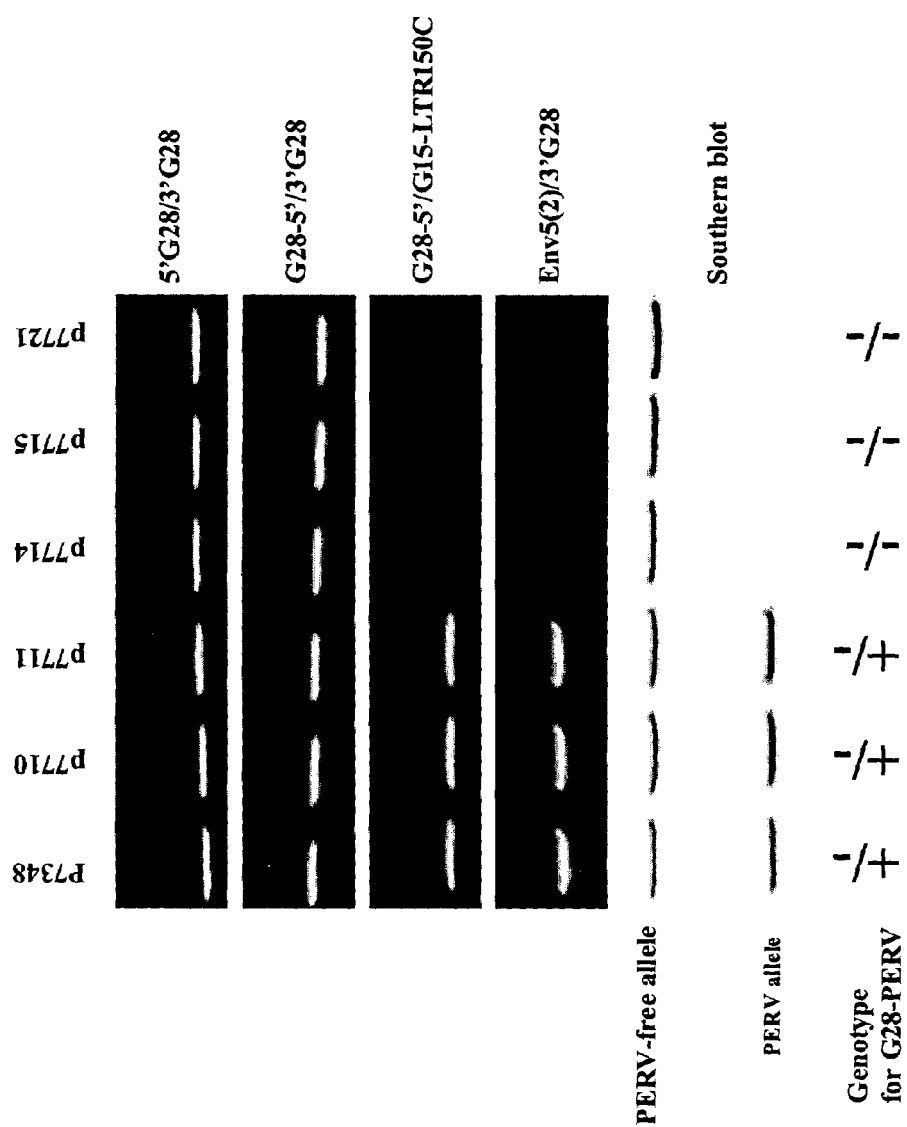
Figure 7. Allele polymorphism analysis of G28-PERV.

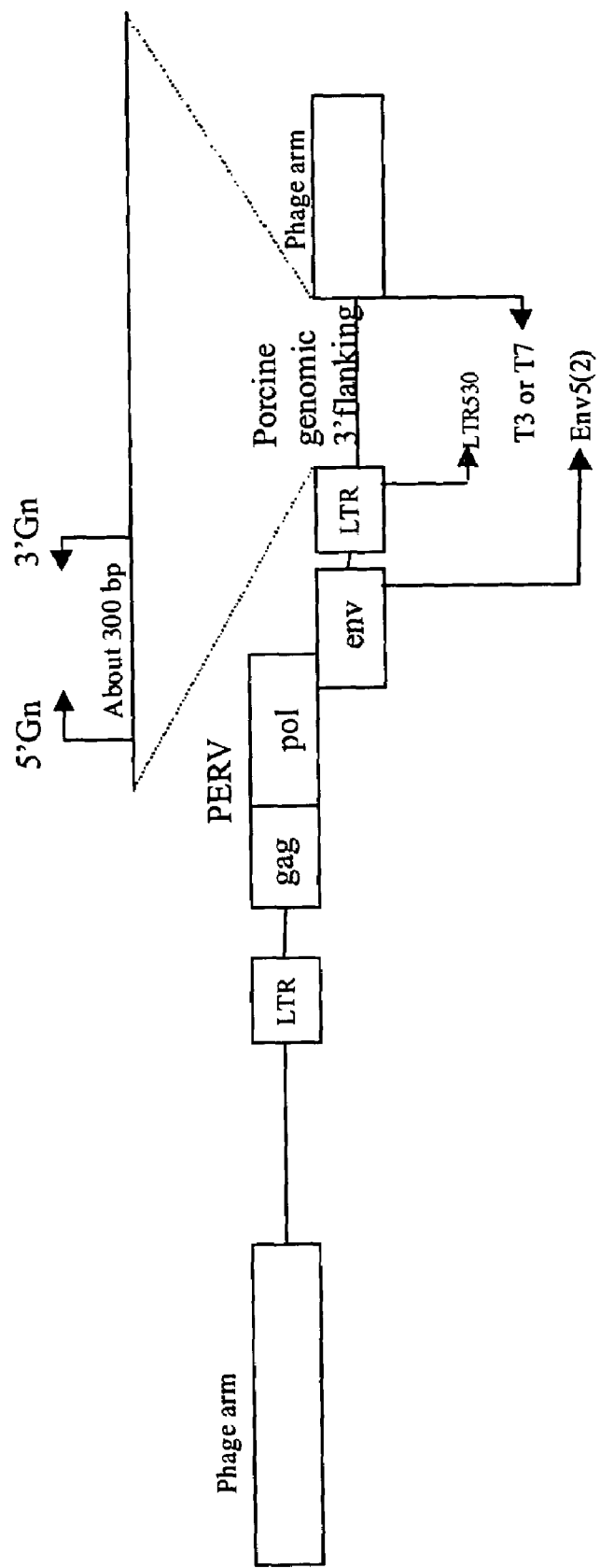
Figure 8. Determination of 3' flanking sequence

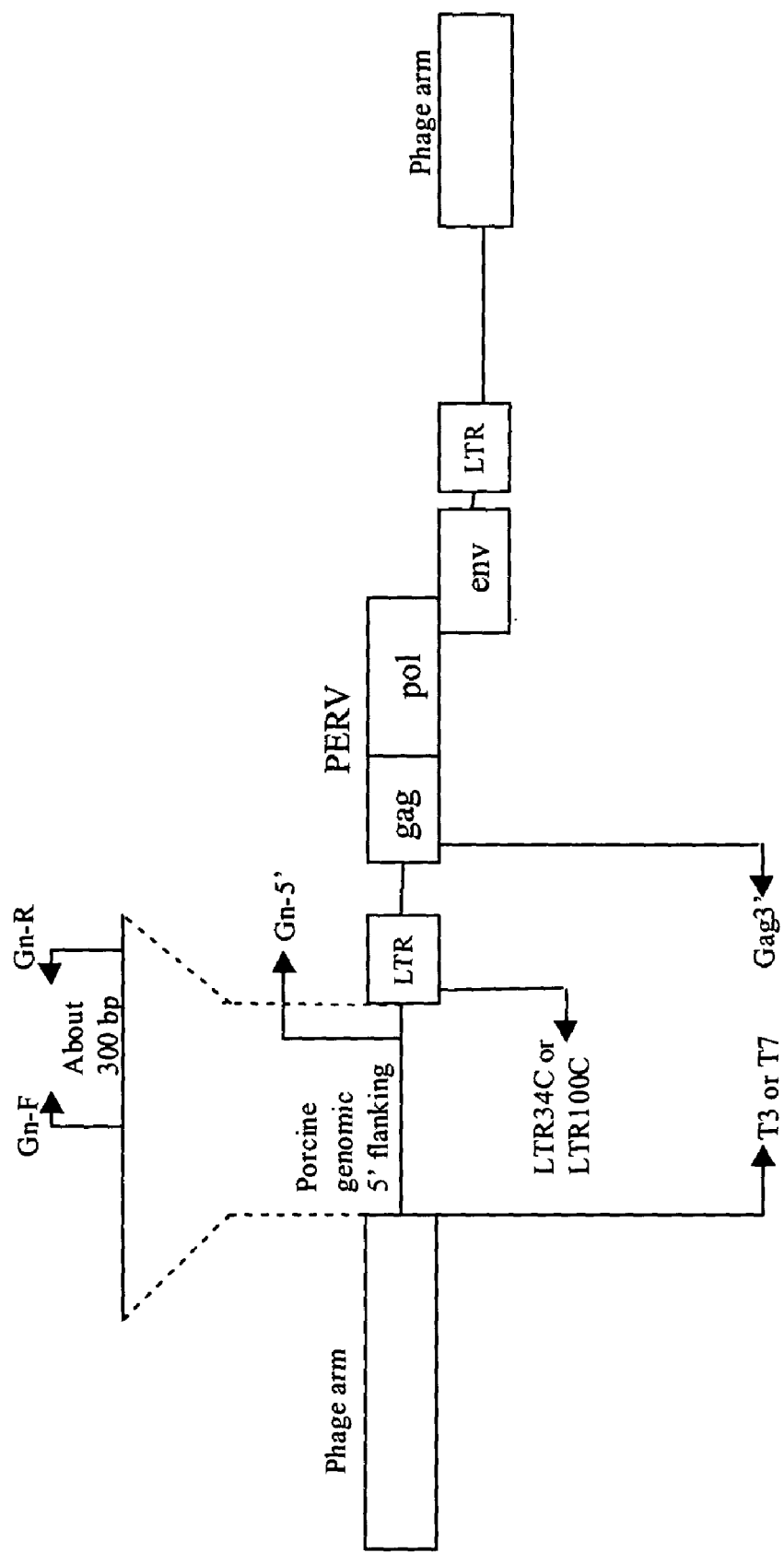
Figure 9. Determination of 5' flanking sequence

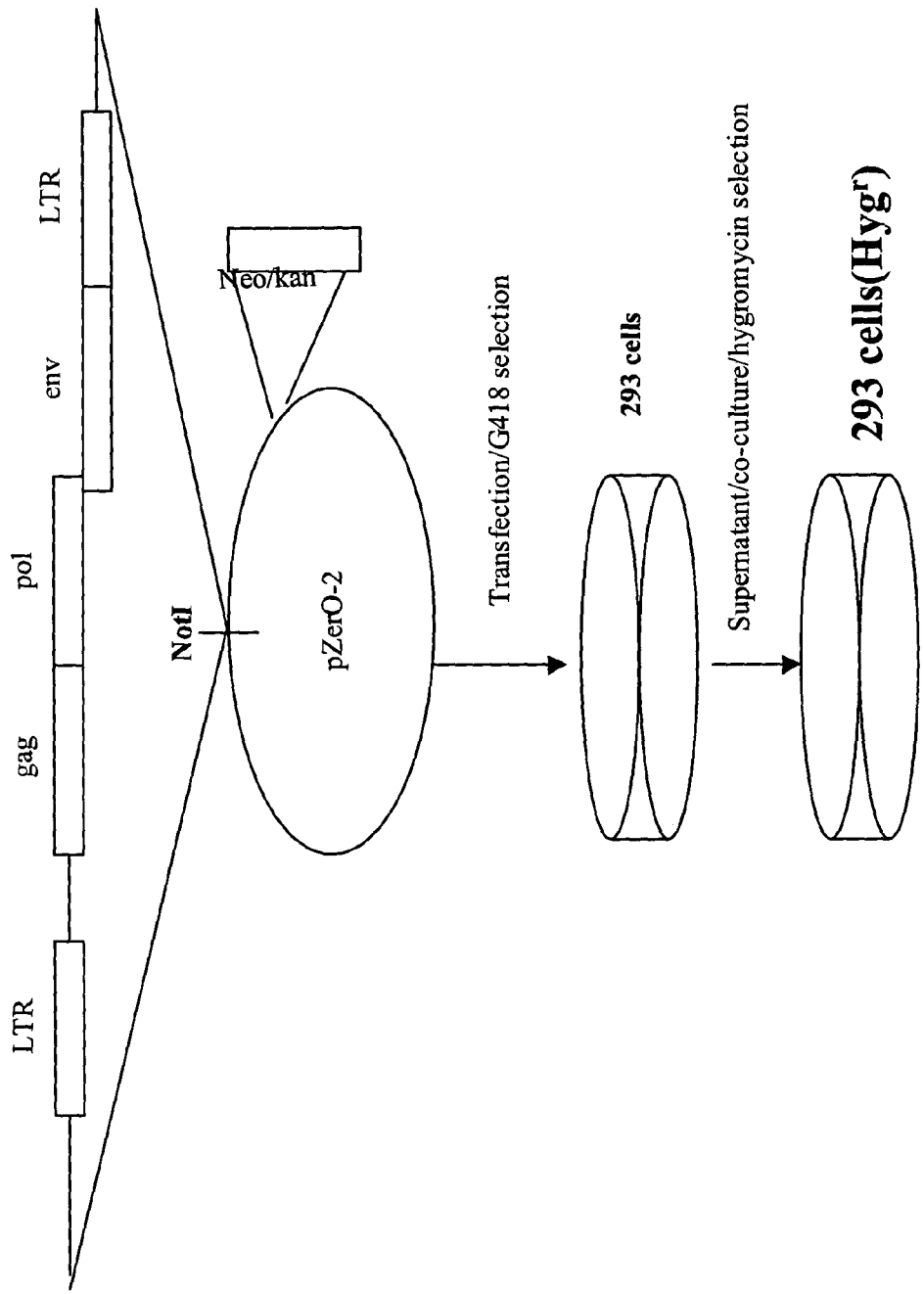
Figure 10. Subcloning of PERV

```
TGAAGGATGAAAATGCAACCTTAACCCTCCCAGAACCCAGGAAGTTAATAAAAGCTCTAAATGCCCCCGAATTCC
AGACCCTGGCTGCTGGCTAAATGAGTTGACTAATAGGTAGAAGGTCACACTTCCTATTGTTCCAGGGCCTGCTATCCTGGCCTAAGT
AAGATAACAGGAAATGAGTTGACTAATCGCTATCTGGATTCTGTAAAACTGACTGGCACCATAGAAGAATTGATTA
CACATTGACAGCCCTAGTGACCTATCTCAACTCGTCTCACTCTGCCCAGGAGCCCACGCAGATGCGACCTCC
GGAGCTATTTAAAATGATTGGTCCAGAGCGCGGGCTTCTCGATATTTAAAATGATTGGTCCACGGAGCGCGGGC
TCTCGATATTTAAAATGATTGGTTTGTGACGCACAGCTTTGTTGTGAACCCATAAAAGCTGTCCCGATTCCGCA
CTCGGGGCCAGTCCTCTACCCCTGCGTGGTGTACGACTGTGGGGTGCGCCTTGGAATAAAAATCCTCTGC
TGTTTGCATCAAGACCGCTTCTCGTGAGTGATTTGGGGTGTCGCCTCTTCCGAGCCCGGACGAGGGGATTGTTCTT
TTACTGGCCTTTCATTGGTCAATTGTGTGTCCGCCGGTCTCTGTTCTGAGTGTCTGTTTCGGTGATGCGCT
AAGGATCCCCTTTGAACTGTCCTCTCAGACCGTAAGGACTGGAGGACTGTGATCAGCAGACTGTCCTAGGAGGATCACAGGC
TTCGGTTTGCAGCTGTCCTCTCAGACCGTAAGGACTGGAGGACTGTGATCAGCAGACTGTCCTACTGTCGTCAGAGGACC
TGCCACCCTGGGGGACGCCCCGGAGGTGGGAGAGCCAGGAGACGCCTGGTGGTTCTCCGACTCTCTTTGCCTGCTGTGGAAGACGGACG
GAGTTCTGTTGTCGATCTGTTGGTTTCGTGTTCTGACTCTCGACCATTGGACTGAAGTTAGATCCAGGGCTCATAATTTGT
GGGACAGACAGTGACGACCCCCCTTAGTTTGACTCTCGACCATTGGACTGAAGTTAGATCCAGGGCTCATAATTTGT
CAGTTCAGGTTAAGAAGGACCTTGGCAGACTTTCTGTGTTAAGGCAATCATTTCAGACTGGACCCAGCTCTCATCCTGA
GAGGGACCTTTAATTCTGAAATTATCCTGGCTGTGTTAAGGCAATCATTTCAGACTGGACCCAGCTCTCATCCTGA
TCAGGAGCCCTATATCCTTACGTGGCAAGATTTGGCAGAAGATCTCCGCCATGGGTTAAACATGCTAAATAAAC
CAAGAAAGCCAGGTCCCCGAATCCTGGCTCTGGAGAGAGAAAACAAACACTCGGCCGAAAAAGTCGAGCCCTCTCCT
CGTATCTACCCCGAGATCGAGGAGCCGCGACTTGGCCGGAACTTGTTCCCCAACCTGTTCCCCACCCCTTATCCAGCACA
GGGTGCTGTGAGGGACCCCTCTGCCCCTCCTGGAGCTCCGGTGTGAGGGACCCTGCGCCGGGACTCGGAGCCGGA
GAGGCGCCACCCGGACGGAGCAGAGATCGCGATATTACCGCTGCGCACCTATGCCCTCCACGGAAAACTAACCATCCCCCTTTCTC
CAATTGCAGCCCCAACGCCTCCAGTATTGGCCCTTTGGTGGAGTCCCTTATGTTCTCTCACCAGCCTACTTGGGATGATTGTCAAC
GGAGGATCCCCAACGCCTCACACCGAGGAGCGAGAGAATTCTGTTAGAGCTAGAAAAAATGTTCCTGGGCC
AGCTGCTGCAGACACCACGAGTTGCAAAATGCAAAATCTATCGCCAGGCTCTGGTGGCGCTCCCGGGGCGCCTCAAGACGGCCA
GACGGCGACCCCACGAGTTGCAAAATGCAAAATCTATCGCCAGGCTCTGGTGGCGCTCCCGGGGCGCCTCAAGACGGCCA
GGCTGAAGTAGGAGAGCTTAAGAGAGGTGATGCAGGGACCGAACGAACCTCCCTCGTATTTCTTGAGAGGCTCATGAA
CTAATTTGGCTAAGGTAAGAGAGGTGATGCAGGGACCGAACGAACCTCCCTCGTATTTCTTGAGAGGCTCATGAA
GCCTTCAGGCGGTTCACCCTTTGATCCTACCTCGGAGGCCCAGAAAGCCTCAGTGGCCCTGGCCTTCATTGGGCA
GTCGGCTCTGATATCAGAGAAAGAACTTCAGAGACTGAAGGGTTACAGGAGGCTGAGTTACGTGATCTAGTGAGAG
```

Figure 11

```
AGGCAGAGAAGGTGTATTACAGAAGGGAGACAGAAGAGAGGAGAAGAAACAGAGAAAAGGAGAGAGAGAAGG
GAGGAAAGACGTGATAGACGGCAAGAGAGAAGAATTTGACTAAGATCTTGGCCGCAGTGGTTGAAGGGAAGAGCAGCAG
GGAGAGAGAGAGAGATTTAGGAAAAATTAGGTCAGGCCCTAGACAGTCAGGGAACCTGGGCAATAGAGACCCCACTCG
ACAAGGACCAGTGTGCTATTGTAAAGAAAAGGACACTGGGCAAGAACTGCCCAAGAAGGAAACAAAGGACCG
AAGTCCTAGCTCTAGAAGATAAAGATTAGGGGAGACGGGGTTCGGACCCCCTCCCCCGAGCCCCAGGTAACTTT
GAAGGTGGAGGGGCAACCAGTTGAGTTCCTGGTTGATACCGGAGCCATTCAGTGCTGTACAACCATTAGGAA
AACTAAAAGAAAAAAAAATCCTGGTGGTGCCACAGGGCAGGGCAGTATCCATGACTACCCGAAGAACCGTT
GACTTGGCAGTGGGACGGGTAACCCACTCGTTTCTGGTCATCCCTGAGTGCCCAGTACCCCTTCTAGGTAGAGACTT
ACTGACCAAGATGGGAGCTCAAATTTCTTTTGAACAAGAAGACCAGAAGTGTCTGAATAACAAACCATCACTG
TGTTGACCCTCCAATTAGATGATGAATATCGACTATATTCTCCCAAGTAAAGCCTGATCAAGATATACAGTCCTGG
TTGGAGCAGTTTCCCCAAGCCTGGGCAGAAAACCGCAGGGATGGGTTTGGCAAAGCAAGTTCCCCACAGTTATTCA
ACTGAAGGCCAGTGCTACACCAGTATCAGTCAGACAGTACCCCTTGAGTAGAGAGGCTCGAGAAGGAATTTGGCCGC
ATGTTCAAAGATTAATCAACAGGGCATCCTAGTTCCTGTCCAATCCCCTGGAATACTCCCCTGCTACCGGTTAGG
AAGCCTGGGACCAATGATTATCGACCAGTACAGGACTTGAGAGAGGTCAATAAAAGGGTGCAGGACATACACCCAAC
GGTCCCGAACCCTTATAACCTCTTGAGCGCCCCTCCCCGCCTGAACCTGGTACACAGTGGACTTGGACTTAAAGATG
CCTTCTTTCGCTGAGATTACACACCCCACTAGCCAACCGCGTTTTGCCTTCGAATGGAGAGATCCAGGTACGGGAAGA
ACCGGGCAGCTCACCTGACCCTGACCCTGCGCCCCAAGGGTTCAAGAACTCCCCGACCATCTTTGACGAAGCCTACACAG
GGACCTGGCCAACTTCAGGATCCAACACCCTCAGGTGACCCTCAGGTGATGACCGTAGTACGTGACCTGCTTCTGCGGGAG
CCACCAAACAGGACTGCTTAGAAGGTACGAAGGCACTACTGCTGGAATTGTCTGACCTAGGCTACAGAGCCTCTGCT
AAGAAGGCCCAGATTTGCAGGAGAGAGGTAACATACTTGGGTACAGTTTGCGGGGCGGCAGCGATGCGCTGACGGA
GGCACGGAAGAAAACTGTAGTCCAGATACCGGCCCCAACCACAGCCAAACAAGTGAGAGTTTTGGGACAGCTG
GATTTGCAGACTGTGGATCCCGGGTTTGCGACCTTAGCAGCCCCACTCTACCCGCTAACCAAAGAAAGGGGAA
TTCTCCTGGCGTAACTAAACCCTTTACCCTTGATGCTATCAAAAGGCCCTGCTCGAGCCCGAGGAGTTTAACCAAACCC
CCCTGACGTACGTTCGGCAGCCCCAGACCGATGAGTAAGGAGTAGCCCGAGGAGTTGATCTGTAGCAGTGGTTGCCCTG
TAGGACCATGGAGGAGACCTGTTGCCTACCTGTCAAGAAGCTTGATCCTGTAGAAGCGCTGACAAATTGACTTTGGACAGAATATAACTGTAATAGC
AAGGCTATCGCAGCTGTGGCCATACTGGTCAAGGACGCTGACACCGATGACCCCGCCACTCTTCTGCCTCAAA
CCCCCATGCATTGAGAACATCGTTCGGCAGCCCCAGACCGATGACCCCGCCACTCTTCGCCACTCTTCTGCCTCAAA
GCCTGCTTCTCACAGAGGGTCACTTCGCTCAACCCTGCCACCAGCCGCTCTCCAACCCTGCCACTCTTCTGCCTGAAGAGACT
GATGAACCAGTGACTGACTCATGATTGCCATCAACTATTGATTGAGGAGACTGGGGTCCGCAAGGACCTTACAGACATACC
```

Figure 11 (cont'd)

GCTGACTGGAGAAGTGCTAACCCTGGTTCACTGACGGAAGCAGCTATGTGGTGAAGGTAAGAGGATGGCTGGGGCGG
CGGTGGTGGACGGGGACCCACACGATCTGGGCCAGCCCTGCCGAAGGAACTTCAGCGCCAAAAGGCTGAGCTCATG
GCCCTCACGCAAGCTTTGCGGCTGGCCGAAGGGAATCCATAAACATTTATACGGACAGCAGGTATGCCTTTGCGAC
TGCACACGTACACGGGGCCATCTATAAACAAGGGGTTGCTTACCTCAGCAGGAGGAAATAAGAACAAAGAGG
AAATTCTAAGCCTATTAGAGCCCTTACATTTGCCAAAAAGCTAGTTGCCAAGCCAGCAGCCCTGTTAACCTTCTGCC
AAAGATCTCATATCTAGAGGGAACCAGATGGCTGACCGGGTTGCCAAGCACCCTAGAGACTGGCAAGAGATAAAAAGATAG
TATAATAGAAACGCCCAAAGCCCAGAACCCAGACAGTACACCCTAGAAGGAAATCCTGCCCCACAAAGAAGGTTA
ACCAGTTCTCTGAGACTCCGGAGGGGACCTGCTATACCTCATATGCTAGAACTAAACACCTGCAGCAGTTGGTCAGAACATCCCTTA
GAATATGTCCAACAGATACATCGTCTCACCCACCTAGGAACTAAACACCTGCAGCAGTTGGTCAGAACATCCCTTA
TCATGTTCTGAGGCTACCAGGAGTGGCTGGTCAAACATTGTGCCCTGCCCAGCTGGTTAATGCTAATC
CTTCCAGAATACCTCCAGGAAAGAGAACTAAGGGAAGCCACCCAGGCGCTCACTGGGAAGTGGACTTCACTGAGGTA
AAGCCGGCTAAATACGGAAACAAATATCTATTGGTTTTGTAGACACCTTTTCAGAGGCTTATCCTAC
TAAGAAAGAGACTTCAACCGTGGTGCTAAAAATACTGGAGGAAATTTCCGAGATTTGGAATACCTAAGGTAA
TCGGGTCAGACAATGGTCCAGCTTTGTTGCCCAGGTAAGTCAGGGACTGGCCAAGATATTGGGATTGATTGGAAA
CTGCATTGTGCATACAGAGACTGGCATACCCCAAAGCTCAGGACACAGGTAGAGAGGATGAATAGAACCATTAAAGAGACCCTTACCAA
ATTGACCACAGAGACTGGCATTAATGATTGCTAGCTCTCCTGCCCTTTGTGCTTTTAGGGTTAGGAACACCCTG
GACAGTTTGGGCTGCTGACCCCTATGAATTGCTGTTTCTCTCTAGGCTCAAGGGTTGGTAGAAATTGCTTCTGTACATAGT
GCTGATGTGCTGCTTTCCCAGCCTTTGTTCTCTAGGCTCAAGGGTTGAGGCAACGAGCGTGGAAGCA
GCTCCGGGAGGCCTACTCAGGAGAAGGAGACTTGCAAGTTCCACATCGCTTCCAAGTGGGAGATTCAGTCTATGTTA
GACGCCACCGTGCAGGAAACCCTCGAGACTCGGGTGGAAGGGCCCTTATCTCGTACTTTGACCACCACCAACGGCTGTG
AAAGTCGAAGGAATCTGAGAATCTCCACCTGGATCCATCCGCCCTCCATCGCCCTGGTTCCTTACTCTAACAATAACTCCCCAGCCAGT
CGAAAAGACTGAGAATCCCCTTAAGCTTCGAACCCCCATAGACCCTTTATCCCCTGGTGCTGATTATGTGACCCTGATACGGG
AGTAAACGCCTTATAGAATAGCACTCGAGTGTTGCTCCTAGAGGCACCTGGTGGCCTGAACTGCATTCTGCCTCCGATTGA
TGTCACTGTAAAAGCACACACCCTCCAACCTAGTCCGTAGTTATGGTTCTATTGCTGCCAGCACAGAGAAA
TTAACCCGCTGTTAAAAGCACACCCTCCAACCTAGTCCGTAGTTATGGTTCTATTGCTGCCAGCACAGAGAAA
GAGAAATACTGTGGGGTTCTGGGAATCCTTCTGTAGGAGATGGAGCTGCGTCACCTCCAACGATGGAGACTGAA
ATGGCCGATCTCTCTCCAGGACCGGGTAAAATTCTCCTTTGTCAATTCCGGCCCGGGCAAGTACAAAGTGATGAAAC

Figure 11 (cont'd)

```
TATATAAAGATAAGAGAGCTGCTCCCCATCAGAGACTTAGATTATCTAAAGATAAGTTTCACTGAAAAAGGAAAACAGGAA
AATATTCAAAAGTGGATAAATGGTATGAGCTGGGAATAGTTTTTATAAATATGGCGGGGAGCAGGGTCCACTTT
AACCATTCGCCTTAGGATAGAGACGGGACAGAACCCCTGTGCCAGTGGGACCCGATAAAGTACTGGCTGAACAGG
GGCCCCCGGCCCTGGAGCCACCGTACCAACACGCCGATAATTGCCGTGCCAATTAACCTGCTGCGCCCTGACATAACACAGCCG
CCTAGCAACGGTACCACTGGATTGATTCCTACCAACACGCCTAGAAACTCCCCAGGTGTTCCTGTTAAGACACAGACA
GAGACTCTTCAGTTCTCATCCAGGGAGCTTTCCAAGCCCATCAACTCACCGACCCTGATGCCACTTCTTCTTGTTGGC
TTTGTCTATCCTCAGGGCCTCTTATTATGAGGGGATGGCTAAAGAAGGAAAATTCAATGTGACCAAAGAGCATAGA
AATCAATGTACATGGGGGTCCCGAAATAAGCTTACCCTGAAGTTTCCGGAAGGGACATGCATAGGAAAAGC
TCCCCCATCCACCAACACCTTGCTATAGTACTGGTTATGAGCAGGCCTCAGAAAATCAGTATTAGTACCTG
GTTATAACAGGTGGTGGGCATGCAATATCGTCCCCGAGTGTACTACCATCCTGAGGAAGTGGTCCTTGATGAATATGACTATCG
TTCTGTGTCATGTCCAAATCGTCCCCCGAGTGTACTACCCTAGCTGTAATGCTCGGATTAGGACGGCCGTTGGCGTAG
GTATAACCGACCAAAGAGAGAACCCGTATCACAGAGACCAGCAGCTAGAGAAAGGACTTGGTGAGCTACATGCGGCCATGACA
GAACAGGACGACAGCTGCCCCTGATCACAGAGAGTCTGTTAGCAACCTAGAAGAGTCCCTGACTTCTTGTCTGAAGTGGTTCTACA
GAAGATCTCCGAGCCTTAGATAGATCTGCTGTTTCTAAGAAGAGACTCAGCAGCCTTAAGAAGAATGTTGCTTCT
GAACCGGAGGGGATTAGATCACTCAGGAGCCATCAGAGAGACTCCATGAGCAAGCTTAGAGAGGCGTCGAAGGAAAGA
ATGTAGATCACTCACCAGGAAGCTTAGAGACTCCATGAGCAAGCTTAGAGAGGCGTCGAAGGAAAGA
GAGGCTGACCAGGGGTGGTTTGAAGGATGTTCAACAGGTCTCCCTTGGATGACCACCCTGCTTTCTCTGACGGG
ACCCCTAGTAGTCCTCGTGTTACTTACAGTTGGGCCTTAATTAATAGGTTGTTGTGCCTTTGTTAGAGAAC
GAGTGAGTGCAGTCCAGATCATGTACTTAGGCAACAGTAGGCAACAGAAGAAGTTGGGCAAGGAGAAACTGACCTCTAG
CCTTCCCAGTTCTAAGATTAGAATTAACAAGACAAGAAGTTGGGGAATGAAAGATGAAAATGCAACCTAACCCT
CCCAGAACCCAGGAAGTAATAAAAGCTCTAAATGCCCTGCTATCCTGGCCTAAGTAAGAACAGGAAATGAGTTGACTAATAGTA
GAAGGTCACACTTCCTATTGTTCCAGGCCTGTAAAACTGACTGGCACCATGGAAGAATTGATTACACATTGAAAGCCCTAGTGACGTATCTCA
CTTATCTGATTCTGTAAAACTGACTGGCACCATGGAAGAATTGATTACACATTGAAAGCCCTAGTGACGTATCTCA
ACTGCAATCTGTCACTCTGCCCAGGAGAGCCCGTGCAGATGCGGACCTCCGGAGCTATTTTAAAATGATTGGTCCACGG
AGCGCGGGGTCTCACTCCGATATTTAAAATGATTGGTCCCAGAGCGGGACACTCCGCACTCGGGGCCACTGGTTGCATCAAGAACCGCTCTCTGCGT
GGTGTACGACTGTGGGGCCCCAGCGCGCTTGGAATAAAAATCTCTTGCTGGTTGCATCAAGAACCGCTTCTGCGTGAG
TGATTTGGGGTGTCGCCCTCTTCCGAGCCCGGAACGAGGGGGATTGTTCTTTTACTGCCTTTCA
```

Figure 11 (cont'd)

```
TGAAGGATGAAAATGCAACCTGACTCTCCCAGAACCTGGAAGCTCTAAATGCCCTCGAATTCCA
GACCCTGTTCCCTATAGTAAAAGATCATACTTTTGCTGTGTTTAGGCTTGCTTTCTGCTCTGTACAAACTTTGT
GGAAGGGAAAAACAGGCCCCTGAGTATGTGCCTCTATGCTTGAAACTTCTTGAAACTGCTCCTAACTGCTGTTTG
GCTTCTGTAAACCTGCTTGCATAGATAAAATATATCTGATAAATTGGTCCACAAAGCGGGCTCCTCCCACCCAGAGACAGCACAAACAT
CCACAAAAATGTTGAAAATCCTGATAAATATATCTGGTGACAATATGTCTCCCCACCCAGAGACAGGCACAAACAT
GTAACTCCAGAACAACTTAAAATTAATTGGTCCACAAAGCGCGGGCTCTCGAAGTTTTGAATTGACTGGTTTGCGAT
ATTTTAAAAATGATTAGTTTGTAAAAGCGCGGCTTTGTTGTGAACCCCATAAAAGCTGTCCCGACTCCACACTCGG
GGCCAGTCCCTCTACCCCTGGCGTGAGCTGCCTGGGCCCCAGCGCGCTCGGAATAAAAATCCTCTTGCTGTTT
GCATCAAGACCGCTTCTCGTGAGTGATTGGGGTGTCGCCCTCTTCCGAGTCAGGATGAGAGGGATTTTAACTCGACT
GGCCTTTCAGTTGGTGCGTTGGCCGGGAAACCCGACTACCCCTCACACCCGAGAACCGACTTGGAGGTAAAGGG
ATCCCCTTTGGAACGTGTGAGTGTGTCGGCTGGCGTCTCGTGTTCTGAGTGTCTGTTCCGGTGATGCGCGCTT
TCGGTTTGCAGCTGTCCTCTCAGACCGTAAGACCGGACTGGGGACTGTGATCAGCAGACGTGCTAGGAGGATCACAGGCT
GCCACCCTGGGGACGCCCCGGAGGTGGGGAGAGCCAGGAGCGCCTGGTGTCTCCTTCGCTGCTTGTGTGAAGACGCGGACCG
AGTTCTGTGTTGAAGCGAAAGCTTCCCCCCCTCGTGTTTGGTTTCTGTTTGTCTGTGCGTCCTTGTCTACAGTTTTAATATG
GTCGCGTGTGTCTCGGATCTGTCTTGGTTCTGTTTGACTCTCGACCATTGACTGAAGTTAAATCCAGGCTCATAATTGTC
GGACAGACGGTGACGACCCCTCTTAGTTTGACTCTCGACCATTGACTGAAGTTAAATCCAGGCTCATAATTGTC
AGTTCAGGTTAAGAAGGACCCCTCTGCCGCAGACCTTGGCAGACTTTCTGTGTCTGTTAAAGCAATTATTTTCAGACTGGACCCGGCTCTCATCCGAT
AGGGGACCTTTAATTCTGAGATTATCCTGGCTGTTAAAGCAATTATTTTCAGACTGGACCCGGCTCTCATCCGAT
CAGGAGCCCTATATCCTTACGTGGCAAGATTTGGCAGAGGATCTCCCGCCATGGGTTAAACCTTGGCTGAATAAGCC
AAGAAAGCCAGGTCCCCGAATTCTGCTCTTGGAGAGAGAAAAACAAACACTCGGCTGAAAAAGTCAAGCCCTCTCCTC
ATATCTACCCCGAGATTGAGGAGCCGGCCTTGGCCGGACCGCTTGCCCCAATCGTTCCCCACCCCCCTTATCCGGCACAG
GGTGCTGCGAGGGGACCCTCTGCCCCCTCCTGGAGCTCCGGAGGGACCTGCTGCAGGGGACTCGGAGGCCGGAG
GGGCGCCACCCCGAGCGGAACAGAGATCGCGACATTACCGCTGCGCAGCCCTCCCATACCGGGGGCC
AATTGCAGCCCCCACTCTTCACAACCGAGAGAGAGAGAATTCTGTTAGAGCTAGAAAAATGTTCCTGGGCCG
ACGGGGACCACCAGCAGTTGCAAAATGAGCTTGAAAATCTATCGCCAGCTCGGTTGGCGCCTCAAGACGCCCAC
GCTGAAGGTAGGAGAGCTTAAGAGAGGTGATGCAGGGACCGAATGAACCTCCCTCAGTTTTTCTTGAGAGGCTCATGGAAG
TAACTTGGCTAAGGTAAGG
```

Figure 12

```
CCTTCAGGCGGGTTCACCCCTTTGATCCTACCTCGGAGGCTCAGAAAGCCTCAGTGGCTCTCGGCCTTCATAGGACAG
TCAGCCCTGATATCAGAAAGAAGAGCTTCAGAGACTTGGAAGGTTACAGGAGGTCGAAGGCTGAGTTACGTGATCTAGTGAAGGA
GGCAGAGAAAGTGTATTACAAAGGGAGACAGAAGAATTTGACTAAGATCTTGGCTGCAGTGGTTGAAGGAAAAGCAATAGG
AGGAAAGACGTAATAAACGGCAAGAGAGATTTTAGGAAATAAGCTGAAGATAAAGACTAGGGAAGACGGGGTTCGAGGCCCAGGTAACTTTA
AAGGTGGAGGGCAACCAGTTGAGTTTCTGGTTGATACGCGGAGCGAAACATTCAGTGCTACTACAGCCATTAGGAAA
ACTAAAAGATAAAAAATCCTTGGGTGATGGGTGCCACAGGGAAACAACAATATCCATGACTACCCGAAGAACAGTT
GACTTGGGAGTGGGACGGGTAACCACTCGTTCTGGTCATACCTGAGTGCCCAGCACCCCTCTTAGGTAGAGACTT
ACTGACCAAGATGGGAGCACAAATTTCTTTGACGAAACCAGAAGTCTCTGCAAATAACAAACCTATCACTG
TGTTGACCCTCCAATTAGATGACGAATATCGACTATATTCTCCCCTAGTAAAGCCTGATCAAAATATACAATTCTGG
TTGAACAGTTTCCCCAAGCCTGGGCAGAAACCGCAGGATGGGTTTGGCAAAGCAAGTTCCCCACAGTTATTCA
ACTGAAGGCCAGTGCTGCACCAGTGTCAGACAGTACCCCTGAGTAAAGAAGCTCGAGAAGGAATTCGGCCGC
ATGTTCAAAGATTAATCAACAGGGCATCCTAGTTCCTGTCCAATCTCCCTGAATACTCCCCTGCTACCGGTTAGA
AAGCCTGGGACTAATGACTATCGACCAGTACAGGACTTGAGAGAGTCAATAACGGGTGCAGGATATACACCAAC
AGTCCCGAACCCTTATAACCTCTGTGTCCTCCCACCCAAGGGTTCAAAAACTCCCCGACCATCTTTGACGAAGCCCTACACAG
CCTTCTCTGCCTGAGACTACATCCCACTAGCAGCACCACCACTTTTGCCTTTGCTGGAATGGAGAGATCCAGTGCGGAAGA
ACGGGCAGCAGTCCACTTGGACTGCCCCAAGGGTTCAAAAACTCCCCAGTACGTGGATGACCTAGGCTACAGAGCCTCGCT
AGACCTGGCCAACTTCAGGATCCAACACCCCAGGTGACCTGACCTACTGGAAGGCACTACATACTTGGGATACAGTTTGCGGGGCG
CCACCAAACAGGACTGCTTAGAAGGTAACAACGGCGAAGGCACTAACATACTTGGGATACAGTTTGCGGGGCG
AAGAAGGCCAGATTGCAGGAGAACTGCTAGTCAGATCCAGATGAGCCCCACCACAGTGAGGACAAGTGAGAGAGTTTTGGGACAGCTG
GGCACGGAAGAGAACTGTAGTCAGATCCAGATGAGCGTAAGGAGCGTAAGGAGTAGCCCGGGGAGTTGTAACCCAAACTC
GATTTGCAGACTGTGAGACTCCGGGGTTTGCGATCCAGAAGGCATTTGATGCTATCAAAAAGGCCCTGCGAGCGCACCTGCTCTGCCCT
TTCTCCTGGGCTCGACTACTAAACCCTTTACCCTTTATGTGGATGAGCGTAAGGAGTAGCCCGGGGAGTTTTAACCCAAACTC
TAGGACCATGAGAGAGACCTGTTGCCTACCTGTCAAGGACGCTGACAAATTGACTTTGGACAGAATATAACTGTAATAGC
AAGGCTATCGCAGCTGTGCCATACTGGTCAAGGACGCTGACAAATTGACTTTGGACAGAATATAACTGTAATAGC
CCCCATGCATTGAGAACATCGTTCGGCAGCCCCAGACCGATGATGACCAACGCCCGCATGACCACTACTATCAAA
GCCTGCTTCTCACAGAGAGGTCACGTTCGCTCCAACCCTGCTCTCCCACTCTTCTGCCTGAAGAGACT
```

Figure 12 (cont'd)

```
GATGAACCAGTGACTCATGATTGCCATCAACTATTGATTGAGGAGACTGGGGTCCGCAAGGACCTTACAGACATACC
GCTGACTGGAGAAGTGTTAACCTGGTTCACTGACGGAAGCAGCTATGTGGTGAAGGTAAGAGGATGGCTGGGGCGG
CGGTGGTGGACGGGACCCGCACGATCTGGGCCAGCAGCCTGCCGAAGGAACTTCAGCACACAAAGGCTGAGCTCATG
GCCCTCACGCAAGCTTTGCGGCTGGCCGAAGGGAAATCCATAAACATTTATACAGACAGCAGGTATGCCTTTGCGAC
TGCACACGTACACGGGGCCATCTATAGAAGCCTTACATTTGCCAAAAAGGTAGCTATTATACACTGTCCTGGACATCAGAAAGCC
AAATTCTAAGCCTATTAGAAGCCTTACATTTGCCAAAAAGGTAGCTATTATACACTGTCCTGACATCAGAAAGCC
AAAGATCCCATATCCAGAGGGAACCAGATGGCTGCCAAGCAGCGGGGTTGCCAAGCAGCCCAGGGTGTTAACCTTCTGCC
TATGATAGAAACACCCAAAGCCCAGAACCCGACGACAGTACACCCTAGAAGACTGGCAAGAATAAAAAAGATAG
ACCAGTTCTCTGAAACTCCGGAGGGACCTGCTATACCTCAGATGGAAGGAAATCCTGCCCCACAAAGAAGGTTA
GAATATGTCCAACAGATACATCGTCTAACCACCTAGAGAACTAAACACCTGCAGTTGGTCAGAACATCCCCTTA
TCATGTTCTGAGGCTACCAGGAGTGGCTGACTCGGTGGTCAAACATTGTGTGCCCTGCCAGCTGGTTAATGCTAATC
CTTCCAGAATACCTCAGGAAAGAGACTAAGGGGAAGCCACCCAGGCGCTCACTGGGAAGTGGACTTCACTGAGGTA
AAGCCCGGCTAAATACGAAACAAATATCTATTGGTTTTTGTAGACACCTTTTCAGATGGGTAGAGGCTTATCCTAC
TAAGAAGAGACTTCAACCGTGGTGCTAAGAAAATACTGGAGGAAATTTTCCAAGATTGGAATACCTAAGGTAA
TAGGGTCAGACAATGGTCCAGCTTTCGTTGCCCAGGTAAGTCAGGGACTGGCCAAGATATTGGGATTGATTGGAAA
CTGCATTGTGCATACAGAGATCAGGAGGACAGGTAGAGAGGATGATGAATAGAACCATTAAAGAGACCCTTACCAA
ATTGACCACAGAGACTGGCATTAATGATTGGATAGCTCTCCTGCCCTTTGTCTTTTTAGGGTGAGGAACACCCCTG
GACAGTTTGGGCTGACCCCCTATGAATTGCTCTACGGGGACCCCGTTGGCAGAAATTGCCTTTGCACATAGT
GCTGATGTGCTGTTTCCCAGCCTTGTTCTCTAGGCTCAAGGCTCGAGTGGGTGAGGCAGCGAGCGTGGAAGCA
GCTCGGAGGCCTACTCAGGAGGAGACTTGCAAGTTCCACATCGCTTCCAAGTTGGAGATTCAGTCTATGTTAGAC
GCCACCGTGCAGGAAACCTCAGAGAAACTCGGTGGAAGGAGACCTTATCTCGGCGCCACCTCCCGATTCGGGGTGAAAGCCGA
GTCGAAGGAATCCCACCTGGATCCATGCATCCGGCCGTTAAGCCACGTTCCTTACTCTGTCAATAACTCCTCAAGTTAATGGT
AAAGACTGAAAATCCCCTTAAGCCCGAACTCCCATAAACCCTTATCTCTCACCTGGTTACTTACTGACTCCGGTACAGGTAT
AACGCCTTGTGGACAGCCCGAACTCCCATAAACCCTTATCTCTCACCTGGTTACTTACTGACTCCGGTACAGGTAT
TAATATTAACAGACACTCAAGGGAGGCTCCTGGTGGCCTGAGTTATATGTCTGCCTTCGATCAGTAA
TCCCTGGTCTCAATGACCAGGCCACACCCCGATGTACTCCGTGCTTACGGTTTTACGTTTGCCCAGGACCCCA
AATAATGAAGAATATTGTGAATATCCTCAGGATTTCTTTTGCAAGCAATGGAGCTGCGTAACTTCTAATGATGGGAA
TTGGAAATGGCCAGTCTCTCAGCAAGACAGAGTAAGTTACTCTTTTGTTAACAATCCTACCAGTTATAATCAATTTA
ATTATGGCCATGGGAGATGAAAAGATTGGCAACAGCGGTACAAAAAGATTACGAAATAAGCAAATAAGCTGTCAT
```

Figure 12 (cont'd)

```
TCGTTAGACCTAGATTACTTAAAAATAAGTTTCACTGAAAAAGGAAAAACAAGAAAAATATTCAAAAGTGGGTAAATGG
TATGTCTTGGGAATAGTGTACTATGGAGGCTCTGGGAGAAAGAAGATCTGTTCTGACTATTCGCCTCAGAATAG
AAACTCAGATGAACCTCCGGTTGCTATAGGACCAAATAAGGGTTTGGCCGAACAAGGACCTCCAATCCAAGAACAG
AGGCCATCTCCTAACCCCCTCTGATTACAATACAAACCTCTGAGCCTGAGCCTAACATCACTATTAAAAC
AGGGGCGAAACTTTTTAGCCTCATCCAGGGAGCTTTTCAAGCTCTTAACTCCACGACTCCAGAGGCTACCTCTCTT
GTTGGCTTTGCTTAGCTTCGGCCCCACCTTACTGAGGGAATGGCTAGAGGAGGGAAATTCAATGTGACAAAGGAA
CATAGAGACCAATGTACATGGGATCCCAAATAAGCTACCCTTACTGAGGTTTCTGAAAAGGCACCTGCATAGG
GATGGTTCCCCATCCACCAACACCTTTGTAACACTGAAGCCTTTAATCGAAGCTCTGAGAGTCAATATCTGG
TACCTGGTTATGACAGGTGTGTGGGCATGTAATACTGGATTAACCCCTGTGTTTCCACCTTGGTTTTCAACCAAACT
AAAGACTTTGCGTTATGTCCAAATTGTCCCCCGGGTGTACTACTATCCCGAAAAAGCAGTCCTGATGAATATGA
CTATAGATATAATCGGCCAAAAAGAGAGCCCATATCCCTGACACTAGCTGTAATGCTCGGATTGGGAATGGCTGCAG
GCGTGGGAACAGGAACGGCTGCCCTAATCACAGGACCGCAACAGCTGGAGAAAGGACTTAGTAACCTACATCGAATT
GTAACGGAAGATCTCCAAGCCCTAGAAAAATCGTCAGTAACCTGAGGAATCCCTAACCTCCTATCTGAAGTGGT
TCTACAGAACAGAAGGGGGTTAGATCGTTATTTCTAAAGAAGGAGGGTTATGTGTAGCCTTAAAGAGGAATGCT
GCTTTATGTGGATCATTCAGGAGCTATCAGGGACTCCATGAGCAAGCTCAGAGAAAGTTAGAAAAACGTCACAAA
GAAAAGAGGCTGGCCAAGGAAGTTAATAAGAAGCTCTAAATGCCCTGAATTCCAGACCCTGTTCCCTATAGGTAAA
AACAGGACCCCTAGTAATACTGCTCTCCTGTTGCTTACAGTTGGGCTTGCTTACAGTCGGTTTGTTGCCTTTGTTA
GAGAACAAGTGAGTGCAGTTCGGATCATGTCAGTTAGACAGCAGTAGACAGAGAAGTGGGAATAAGGATGAAAATGCAACCT
CTTTAGCCTTCCTAGTTCTAAGATTAGAATTAACAAGAGAAGAAGTGGGAATAATGCCCTGAATTCCAGACCCTGTTCCCTATAGGTAAA
GACTCTCCCAGAACCCAGGAAGTTAATAAGAAGCTCTAAATGCCCTGAATTCCAGACCCTGTTCCCTATAGGTAAA
AGATCATACTTTTGCTGTGTTTTAGGGCTTGCTTCTGCTCTGTACAAAACTTGTGGAAGGGAAAAACAGGCCCCT
GAGTATGTGCCTCTATGCTCTTGAAACTTCTTGAAACTGCTCCTAACTGCTCTGTTGTTTGGCTTCTGTAACCTGCTTGCAT
AAGATAAAAGAGGAGAAGTCAATTGCCTAACGGACCCCAGTAAGACTGGGCGTGCCACAAACATGTAACTCCAGAACAACTTAAAA
ATAAATATATCTTGTGACAATATGTCTCCCCCAGAGACAGGCACAAACATGTAACTCCAGAACAACTTAAAA
TTAATTGGTCCACAAAGCGCGGCTCTCGAAGTTTGAATTGACTGGTTTGCGATATTTTAAAAATGATTAGTTTGT
AAAGCGCGGGCTTTGTTGTGAACCCCATAAAGTGTCCCACTCCACACTCGGGGGCCAGTCCTCTACCCCTGC
GTGGCGTACGACTGTGGGCCCTCTTCGCCCTCTTCCGAGTCAGGATGCAGGAGAGGATTTAACTCGACTGGCCTTTCA
GTGATTTGGGGGTGTCGCCCTCTTCGCCCTCTTCCGAGTCAGGATGCAGGAGAGGATTTAACTCGACTGGCCTTTCA
```

Figure 12 (cont'd)

```
TGAAAGGATGAAAATGCAACCTGACTCTCCCAGAACCCAGGAAGTTAATAAGAAGCTCTAAATGCCCTCGAATTCCA
GACCCTGTTCCCTATAGGTAAAAGATCATACTTTTGCTGTGTTTAGGGCTTGCTCTGTCTGTCTGTACAAACTTTGT
GGAAGGGGAAAAACAGCCCCTGAGTATGTGCCTCTATGCTTGAAACTTCTTGAAACTGCTCCTAACTGCTGTTGTTG
GCTTCTGTAAACCTGTTGAAAATGTTGATAAGATAAAATATATCTTGGTGACAATATGTCTCCCCACCCAGAGACAGGCACAAACAT
CCACAAAATGTTGAAAATCCTGATAAATATATCTTGGTGACAATATGTCTCCCCACCCAGAGACAGGCACAAACAT
GTAACTCCAGAACAACTTAAAATTAATTGGTCCACAAAGCGCGGGCTCTCGAAGTTTGAATTGACTGGTTTGCGAT
ATTTAAAATGATTAGTTTGTAAAAGCGGGCTTTGTTATGAACCCCATAAAAGCTGTCCGACTCCACACTCGGG
GCCGCAGTCCTCTACCCCTCGCTGAGTGATTGGGGTCGCCTCTCCGAGTCAGGACGAGAGGATTTAACTCGACTG
CATCAAGACCGCTTCTGTCGTGAGTGATTGGGGTCGCCTCTCCGAGTCAGGACGAGAGGATTTAACTCGACTG
GCCTTTCAGTTGGTGCGTTGGCCGGGAAACCCGGCGACTACCCCCTCACACCCTGAGTGTCTCTGTTTCGGTGAGGTAAAGGA
TCCCCCTTTGAACGTGTAGTGTGTCCTCTCAGACCGTAAGGACTGGGGACTGTGATCAGCAGACGTGCTAGGAGGATCACAGGCTG
CGGTTTGCAGCTGTGTCCTCTCAGACCGTAAGGACTGGGGACTGTGATCAGCAGACGTGCTAGGAGGATCACAGGCTG
CCACCCTGGGGACGCCCCGGAGGTGGGGAGAGCCAGGAGCGCCTGGTCTCCTTCTGTCGTTGGAAGACGCGGACGGG
GTTCTGTGTTGAAGCGAAAGCTTCCCCCTCGCCGTCCGACTCTTTGCCTGCTTGTGGAAGACGCGGACGGG
TCGCGTGTCGTGTCTCGATCTGTCTGGTTCTGTCTTGTCTCTTGTCTCTGTCTCCTGCTGCTGTCTCTACAGTTTTAATATGG
GACAGACGGTGACGACCCCCTCTAGTTGACTCTCGACCATTGGACTGAAGTTAAATCCAGGGCTCATAATTTGTCA
GTTCAGGTTAAGAAGGACCTTGGCAGATTCTGTGTCTCTGAATGGCCGACATTCGATGTTGGATGGCCATCAGA
GGGGACCTTTAATTCGAGATTATCCTGGCAAGATTGGCAGAGATCCTCCGCCATGGGTTAAACCTTGGCTGAATAAGCCA
AGGAGCCCTATATCTTACGTGACAAGATTGGCAGAGATCCTCCGCCATGGGTTAAACCTTGGCTGAATAAGCCA
AGAAAGCCAGGTCCCCGAGATTGAGGAGCCGGTTGGCCGGAACCCAATCTGTTCCCCACCCCTTATCCGGCACAGG
TATCTACCCCGAGATTGAGGAGCCGGTTGGCCGGAACCCAATCTGTTCCCCACCCCTTATCCGGCACAGG
GTGCTGCGAGGGGACCCTCTGCCCCCTCCTGGAGCTCCGGCGGTGGAGGACCTGCTGCAGGACCTGCGGAGCCGGAGG
GGCGCCACCCCGGAGCGGACAGAGATCGCGACATTACCGCTGCGCACGTACGGCCCTCCCATACCGGGGGCCA
ATTGCAGCCCCTCCAGTATTGGCCCTTTTCTCTCTGCAGATCTCTATAATTGGAAAACTAACCATCCCCCTTTCTCGG
AGGATCCCAACGCCTCACGGGGTTGATGAGTCCCTTATGTTCTCTCACCAGCCTACTTGGGATGATTGTCAACAG
CTGCTGCAGACACTCTTCACAACGAGGAGGAGAGAGAATTCTGTTAGAGGCTAGAAAAATGTTCCTGGGCCGA
CGGGCGACCCACGCAGTTGCAAATGAGATTGACATGGGATTCCCTTGACTCGCCCCGGTTGGGACTACAACACGG
CTGAAGGTAGGGAGAGCTTGAAAATCTATCGCCAGGCTCTGTGGCGGGTCTCCGGGCCTCAAGACGGCCACT
AACTTGGCTAAGAGAGAGAGGTGATGCAGGAGACCGAATGAACCTCCCTCAGTTTTCTTGAGAGGCTCATGGAAGC
```

Figure 13

```
CTTCAGGCGGTTCACCCCTTTGATCCTACCTCGGAGGCTCAGAAAGCCTCAGTGCCCTGCCTTCATAGGACAGT
CAGCCCTGGATATCAGAAGAAGCTTCAGAGACTTCAGAGGGTTACAGGAGGCTGAGTTACATGATCTAGTGAAGGAG
GCAGAGAAAGTGTATTACAAAGGGAGCAAGAGAAGAAGAGAAGAACAAAGAAAAGAGAGAAAGAGAGAAAGGAA
GGAAAGACGTAATAAACGGCAAGAGAGAAGAATTTGACTAAGATCTTGCTGCAGTGGTTGAAGGAAAGCAATAGG
AAAGAGAGACCAATGTGCATATTGTAAAGAAAAAGGACACTGGCAAGGACTGCCCAAGAAGGAAACAAAGGACTGAA
AAGGACCAATGTGCATATTGTAAAGAAAAAGGACACTGGCAAGGACTGCCCAAGAAGGAAACAAAGGACTGAA
GGTCTTAGCTCTGGAAGAAGATAAAGACTAGGGAAGACGGGGTTCGGACCCCCCGAGCCCAGGTAACTTTAA
AGGTGGAGGGCAACCAGTGAGTTTCGGTTGATACCCGAGCGAACAACATTCAGTGCTACTACAGCCATTAGGAAAA
CTAAAAGATAAAAAATCCTGGGTGGTGCCACAGGGCAACAACATATCCATGACTACCCGAAGAACAGTTGA
CTTGGGAGTGGGACGGTAACCCACTCGTTTCTGGTCATACCTGAGTGCCCAGCACCCCTCTTAGGTAGAGACTTAC
TGACCAAGATGGGAGCACAAATTCTTTTGAACAAGGAAACCAGAAGTGTCTGCAAATAACAAACCTATCACTGTG
TTGACCCTCCAATTAGATGACGAATATCGACTATATTCTCCCCTAGTAAAGCCTGATCAAAATATACAATTCTGTT
GAACACAGTTTCCCCAAGCCTGGGCAGAAACCTGGAGCAGTGGTTTGCAAAGCAAGTTCCCCACAGTTATTCAAC
TGAAGGCCAGTGCTGCACCAGTGTCAGTCAGAGACTTCAGACAGGTAAAGAAGCTGAGAAGGAATTCGGCCGCAT
GTTCAAAGATTAATCAACAGGGCATCCTAGTTCCTGTGTCCAATCTCCCCTGAATACTCCCCTGTACCGGTTAGAA
GCCTGGGACTAATGACTATCGACCAGTACAGGACTTGAGAGAGGTCAATAAACGGGTGCAGGATATACACCAACAG
TCCCGAACCCTTATAACCTCTCTGTGTCTCCCACCCAACCACTTTTGCCTTGAATGAGAGATCCAGGTGCGGAAGAAC
TTCTTCTGCCTGACTCACTTGGACTGCCCCAAGGGTTCAAAAACTCCCCGACCATCTTTGACGAAGCCTACACAGAG
CGGGCAGCTCACTTGGACTGCCCCAAGGGTTCAAAAACTCCCCGACCATCTTTGACGAAGCCTACACAGAG
ACCTGGCCAACTTCAGGATCCAACACCCCAGTGACCCTCCTCCAGTACGTGGATGACCTGCTTCTGCGGGAGCC
ACCAAACAGGACTGCTTAGAAGGTACGAAGCACTACTGCTCTGGAATTGTCTGACCTAGGCTACAGAGCCTCGCTAA
GAAGCCCAGATTTGCAGGAGAGAGGTAACATACTTGGGGTACAGTTTGCGGGGGCAGGGGATGGCTGACGGAGG
CACGGAAGAGAACTGTAGTCCAGATACCGGCCCAACCACAGCCAAACAAGTGAGAGAGTTTTGGGACAGTCTGA
TTTTGCAGACTGTGGATCCCGGGGTTTGCGACCAGCCTTAGCGCGACCCTACTAACCAAAGAAAAGGGGAATT
CTCCCTGGGCCTCCTGAGCACCAGAAGGCATTTGATGCTATCAAAAAGGCCCTGCTGAGCGCCACCTGCTCTGCCCTCC
CTGACGTGACTAAACCCTTTACCCTTATGTGGATGAGCGTAAGGAGTAGCCCGGGGAGTTTTAACCCAAACCTA
GGACCATGGAGAGACCTGTTGCCACTACTGGTCAAAGAAGCTCGATCCTGTAGCCAGTGGTTGGCCCGTATGCCTGAA
GGCTATCGCAGTGATGTGGAGAACATCGTTCGGCAGCGACAAATTGACTTTGGACAGAATAACTGTAATAGCCC
CCCATGCGTTGAGACCGTTGGAGAACATCGTTCGGCAGCGACAAATTGACTTTGGACAGAATAACTGTAATAGCCC
CTGCTTCTCACAGAGAGGGTCACGTTCGCTCCAACCCTGCCACTCTTCTGCCTGAAGAGACTGA
```

Figure 13 (cont'd)

```
TGAACCAGTGACTCATGATTGCCATCAACTATTGATTGAGGAGACTGGGGTCCGCAAGGACCTTACAGACATACCGC
TGACTGGAGAAGTGTTAACCTGGTTCACTGTTGGTGACGAAGCAGCTATGTGGTGAAGGTAAGAGGATGGCTGGGCGCG
GTGGTGGACGGGACCCCGACCGATCTGGGCCAGCAGCCTGCCGAAGGAACTTCAGACACAGACCAGGTATGCCTTTGCGACTG
CCTCACGCAAGCTTTGCGGCTGGCCGAAGGGAAATCCATAAACATTTATACAGACAGCAGGTATGCCTTTGCGACTG
CACACGTACACGGGCCATCTATAAGCAAAGGGGTTGCTTACCTCAGCAGGAGGAGAAATAAAGACAAAGAGAA
ATTCTAAGCCTATTAGAAGCCTTACATTGCCAAAAAGGCTAGCTATTATACACTGTCCTGGACATCAGAAAGCCAA
AGATCCCATATCCAGAGGGAACCAGATGGCTGACCGGGTTGCCAAGCAGGCAGCCAGGGTGTTAACCTTCTGCCTA
TGATAGAAACACCCAAGCCAGAACCCCAGAACGACAGTACACCCTAGAAGACTGGCAAGAAATAAAAAGATAGAC
CAGTTCTCTGAAACTCCGGAGGGACCTGCTATACCTCAGATGGAAGGAAATCCTGCCCCACAAAGAAGGGTTAGA
ATATGTCCAACAGATACATCGTCTAACCACCTAGGAACTAAACACCTGGTCAGAAGCAGTTGGTCAGAACATCCCCTTATC
ATGTTCTGAGGCTACCAGGAGTGGCTGACTCGGTGGCTGGTCAAACATTGTGTGCCCTGCCAGCTGGTTAATGCTAATCCT
TCCAGAATACCTCCAGAGAGTGGGGAGCTAAGGAGACTAAGGGGGAGCCACCCAGGCGCTCACTGGAAGTGGACTTCACTGAGGTAAA
GCCGGCTAAATACGGAAACAAATACCTATTGGTGTTTTGTAGAGAAAATACTGGAGGAAATTTTCCAAGATTGGAATACCTAAGGTAATA
AGAAAGAGACTTCAACCGTGGTGCTAAGAAAATACTGGAGGAAATTTTCCAAGATTGGAATACCTAAGGTAATA
GGGTCAGACAATGGTCCAGCTTTCGTTGCCCAGGTAAGTCAGGGACTGGCCAAGATATTGGGATTGATTGGAAACT
GCATTGTGCATACAGACCCCAAAGCTCAGGAGTAGACAGGATGAATAGAACCATTAAAGAGACCCTTACCAAAT
TGACCACAGAGACTGGCATTAATGATTGGATAGCTCTCCAGGGAAGTGCTCTTTTAGGGTGAGGAACACCCTGGA
CAGTTTGGGCTGACCCCCCCTAAGCTTCCAGCCTTTGTTCTCTAGGCTCAAGGCTGAGTGGGTGAGCAGCAGCAGC
TGATGTGCTGTTTCCCAGCCTACTCAGGAGGAGACTTGCAAGTTCCACATCGCTTCCAAGTGGAGATTCAGTCTATGTTAGACGC
TCCGGGAGGCCTACTCAGGAGGAGACTTGCAAGTTCCACATCGCTTCCAAGTGGAGATTCAGTCTATGTTAGACGC
CACCGTGCAGGAAACCTCGGTGGAAGGACTCGGTTGAAGGAGACCTTATCTCGTACTTTTGACCACACCAACGGCTGTGAAAGT
CGAAGGAATCCCACCTGGATCCATGCGGCCATCCCACGTTAAGCCGGCGCCCGATTCGGGGTGGAAAGCCGAAA
AGACTGAAAATCCTCTCAGCAGAGACTCAGCAGAGAGTAAGTTACTCTTTGTTAACAATCCTACCAGTTATAATCATTTAAT
ACGCCTTGTGACAGCCCGAACTCCCATAAACCCTTATCTCTCACCTGGTTACTTACTGACTCCGTACTCAGTATTA
ATATTAACAGCACTCAAGGGCCCGAGGCTCCCTTGGGGACCTGGTGGCCTGAATTATATGTCTGCCTTCGATCAGTAGT
CCTGGTCTCAATGACCAGGCCACACCCCCCCGATGTACTCCGTTGCTTGGTTTACGTTTTGCCCAGGACCCCAAA
TAATGAAGAATATGTGAAATCCTCAGGATTCTTTTGCAAGCAATGGAGCTGCTAACTTCTAATGATGGAATT
GGAAATGCCAGTCTCTCTCAGCAGACTAAGTTACTCTTTTGTTAACAATCCTACCAGTTATATAATCATTTAAT
TATGGCCCATGGGAGATGAAAGATTGGCAACAGCGGGTACAAAAAGATGTACGAAATAAGCTGTCATTC
```

Figure 13 (cont'd)

```
GTTAGACCTAGATTACTTAAAAATAAGTTTCACTGAAAAGGAAAACAAGAGAAATATTCAAAAGTGGGTAAATGGTA
TGTCTTGGGAATAGTGTACTATGGAGGCTCTGGGAGAAAGAAAGGATCTGTTCTGACTATTCGCCTCAGAATAGAA
ACTCAGATGGAACCTCCGGTTGCTATAGACCAAATAAGGGTTTGGCCGAACAAGGACCTCCAATCCAAGAACAGAG
GCCATCTCCTAACCCCTCTGATTACAATACAACCTCTGACAGTCGCCCACTGAGCCTAACATCACTATTAAAACAG
GGGCGAAACTTTTTAGCCTCATCCAGGAGCTCTTCAAGCTCTTACACTCCACGACTCCAGAGGCTACCTCTTCTGT
TGGCTTTGCTTAGCTTCGGGCCCACCTTACTATGAGGGAATGCTAGAGGAGGGAATTCAATGTGACAAAGGAACA
TAGAGACCAATGTACATGGGGATCCCAAAATAAGCTTACCCTTACTGAGGTTTCTGGAAAAGGCACCTGCATAGGA
GGGTTCCCCATCCACCAACACCTTTGTAACCACTGAAGCCTTTAATGAACCTCTGAGAGTCAGTATCTGGTA
CCTGGTTATGACAGGTGGTGGCATGTAATACTGGATTAACCCCTTGTGTTTCCACCTTGTTTTCAACCAAACTAA
AGACTTTGCGTTATGTCCAAATTGTCCCCGGGTGTACTATCCCGAAAAAGCAGTCCTTGATGAATATGACT
ATAGATAATCGGCCAAAAGAGAGCCCATATCCCCTGTAATGCTCGGATTGGGAGTGGCTGCAGGC
GTGGGAACAGAACGGCTGCCCTAATCACAGGACCGCAACAGTCGGAGAAGGACTTAGTAACCTACATCGAATTGT
AACGGAAGATCTCCAAGCCCTAGAAATCGTCAGTGGAGAATCCCTAACCTCCTTATCTGAAGTGGTTC
TACAGAACAGAAGGGGTTAGATCGTTATTCTAAAAGAAGGAGGGTTATGTGTAGCCTTAAAAGAGGAATGCTGC
TTTTATGTGATCATTCAGGAGCTATCAGGAAGGTTGAGGGATGGTTCAACAAGTCCCCATGGTCAAGTGTGACCACCCTGCTTCTCGTCTAA
AAAGAGGCTGGCCAAGGATGGTTTGAGGGATGGTTCAACAAGTCCCCATGGTCAAGTGTGACCACCCTGCTTTCTGCTCTAA
CAGGACCCTAGTAATACTCGATCATGTCTTAGATTAGACAGCAGTAGAACAAGAGAAGTGGGGAATTCCAGACCCTGTTAGA
GAACAAGTGAGTCCAGTTCTAAGAAGTTAATAAGAAGCTCTAAATGCCTCTGTACAAACTTTGTGAAGGGGAAAACTGACCT
TTAGCCTTCCCAGAACCCCAGAAGTTAATAAGAAGCTCTAAATGCCTCTGTACAAACTTTGTGAAGGGGAAAACAGGCCCCTGA
CTCTCCCCAGAACCCCAGAAGTTTTAGGCTTTGCTTGTTTTAGGGCTTGCTCTTGTAAACCTGCTTGCATAA
GTATGTGCCTCTATGTTGCTTATGCTTGAAACTTCTTGAAACTGCTCTTGTTTGGCTTCTTGTAAACCTGCTTGCATAA
GATAAAGAGAGGAGTCAATGCGGCGGTGCCACAAATGTTGAAAATCCTGAT
AAATATCTTGTGACAATATGTCTCCCCCACCCAGAGACAGGCACAAACATGTAACTCCAGAACACTGAT
AATTGGTCCACAAAGCGCGGGCTCTCGAAGTTTGAATTGACTGGTTTGCGATATTTTAAAATGATTAGTTTGTAAA
AGCGGCGGGCTTTGTATGAACGCCCCAGCGCTCCCACACTCCACACTCCGGGGCCGCAGTCTTCATCAAGACCGCTTCATCAAGACCGCTTCTGTGCGTG
GCGTACGACTGTGGGCCCTCTTCCGAGTCAGGATCAGGAGACGAGGGATTTAACTCGACTGGCCTTTCA
ATTTGGGGTGTCGCCCTCTTCCGAGTCAGGATCAGGAGACGAGGGATTTAACTCGACTGGCCTTTCA
```

Figure 13 (cont'd)

SEQUENCE LISTING

<160> NUMBER OF SEQ ID NOS: 139

<210> SEQ ID NO 1
<211> LENGTH: 253
<212> TYPE: DNA
<213> ORGANISM: Sus scrofa
<220> FEATURE:
<223> OTHER INFORMATION: 1881-2133bp, Y12238 PERV env conserved sequence

<400> SEQUENCE: 1

```
cttctatgta gatcactcag gagccatcag agactccatg agcaagctta gagaaaggtt      60
agagaggcgt cgaagggaaa gagaggctga ccaggggtgg tttgaaggat ggttcaacag     120
gtctccttgg atgaccaccc tgctttctgc tctgacgggg ccctagtag tcctgctcct      180 gttacttaca gttgggcctt gcttaattaa taggtttgtt gcctttgtta gagaacgagt     240
gagtgcagtc cag                                                        253
```

<210> SEQ ID NO 2
<211> LENGTH: 253
<212> TYPE: DNA
<213> ORGANISM: Sus scrofa
<220> FEATURE:
<223> OTHER INFORMATION: 2572-2824 bp, Y12239
    PERV-B env conserved sequence

<400> SEQUENCE: 2

```
cttctatgta gatcactcag gagccatcag agactccatg agcaagctta gagaaaggtt      60
agagaggcgt cgaagggaaa gagaggctga ccaggggtgg tttgaaggat ggttcaacag     120
gtctccttgg atgaccaccc tgctttctgc tctgacggga cccctagtag tcctgctcct     180
gttacttaca gttgggcctt gcttaattaa taggtttgtt gcctttgtta gagaacgagt     240
gagtgcagtc cag                                                        253
```

<210> SEQ ID NO 3
<211> LENGTH: 253
<212> TYPE: DNA
<213> ORGANISM: Sus scrofa
<220> FEATURE:
<223> OTHER INFORMATION: PERV-C env conserved sequence; 7227-7479 bp,
    AF038600

<400> SEQUENCE: 3

```
tttttatgtg gatcattcag gggccatcag agactccatg aacaagctta gagaaaggtt      60
ggagaagcgt cgaagggaaa aggaaactac tcaagggtgg tttgagggat ggttcaacag     120
gtctctttgg ttggctaccc tactttctgc tttaacagga cccttaatag tcctcctcct     180
gttactcaca gttgggccat gtattattaa caagttaatt gccttcatta gagaacgaat     240
aagtgcagtc cag                                                        253
```

<210> SEQ ID NO 4
<211> LENGTH: 2040
<212> TYPE: DNA
<213> ORGANISM: Sus scrofa
<220> FEATURE:
<223> OTHER INFORMATION: PERV-A; 94-2133 bp, Y12238

<400> SEQUENCE: 4

```
cagtctatgt tagacgccac cgtgcaggaa acctcgagac tcggtggaag ggaccttatc      60
tcgtactttt gaccacacca acggctgtga aagtcgaagg aatccccacc tggatccatg     120
catcccacgt taagccggcg ccacctcccg attcggggtg gaaagccgaa aagactgaaa     180
atccccttaa gcttcgcctc catcgcgtgg ttccttactc tgtcaataac tcctcaagtt     240
aatggtaaac gccttgtgga cagcccgaac tcccataaac ccttatctct cacctggtta     300
cttactgact ccggtacagg tattaatatt aacagcactc aaggggaggc tcccttgggg     360
acctggtggc ctgaattata tgtctgcctt cgatcagtaa tccctggtct caatgaccag     420
gccacacccc ccgatgtact ccgtgcttac gggttttacg tttgcccagg accccccaat     480
aatgaagaat attgtggaaa tcctcaggat ttcttttgca agcaatggag ctgcataact     540
tctaatgatg ggaattggaa atggccagtc tctcagcaag acagagtaag ttactctttt     600
gttaacaatc ctaccagtta taatcaattt aattatggcc atgggagatg gaaagattgg     660
caacagcggg tacaaaaaga tgtacgaaat aagcaaataa gctgtcattc gttagaccta     720
gattacttaa aaataagttt cactgaaaaa ggaaaacaag aaaatattca aagtgggta      780
```

```
aatggtatat cttggggaat agtgtactat ggaggctctg ggagaaagaa aggatctgtt      840
ctgactattc gcctcagaat agaaactcag atggaacctc cggttgctat aggaccaaat      900
aagggtttgg ccgaacaagg acctccaatc caagaacaga ggccatctcc taacccctct      960
gattacaata caacctctgg atcagtcccc actgagccta acatcactat aaaacagggg     1020
gcgaaacttt ttagcctcat ccagggagct tttcaagctc ttaactccac gactccagag     1080
gctacctctt cttgttggct ttgcttagct tcgggcccac cttactatga gggaatggct     1140
agaggaggga aattcaatgt gacaaaggaa catagagacc aatgtacatg gggatcccaa     1200
aataagctta cccttactga ggtttctgga aaaggcacct gcatagggat ggttcccccca     1260 tcccaccaac acctttgtaa ccacactgaa gcctttaatc gaacctctga gagtcaatat     1320
ctggtacctg gttatgacag gtggtgggca tgtaatactg gattaccccc ttgtgtttcc     1380
accttggttt tcaaccaaac taaagacttt tgcgttatgg tccaaattgt cccccgggtg     1440
tactactatc ccgaaaaagc agtccttgat gaatatgact atagatataa tcggccaaaa     1500
agagagccca tatccctgac actagctgta atgctcggat tgggagtggc tgcaggcgtg     1560
ggaacaggaa cggctgccct aatcacagga ccgcaacagc tggagaaagg acttagtaac     1620
ctacatcgaa ttgtaacgga agatctccaa gccctagaaa aatctgtcag taacctggag     1680
gaatccctaa cctccttatc tgaagtggtt ctacagaaca aaggggggtt agatctgtta     1740
tttctaaaag aaggagggtt atgtgtagcc ttaaaagagg aatgctgctt ctatgtagat     1800
cactcaggag ccatcagaga ctccatgagc aagcttagag aaaggttaga gaggcgtcga     1860
agggaaagag aggctgacca ggggtggttt gaaggatggt tcaacaggtc tccttggatg     1920
accaccctgc tttctgctct gacggggccc ctagtagtcc tgctcctgtt acttacagtt     1980
gggccttgct taattaatag gtttgttgcc tttgttagag aacgagtgag tgcagtccag     2040
```

<210> SEQ ID NO 5
<211> LENGTH: 2030
<212> TYPE: DNA
<213> ORGANISM: Sus scrofa
<220> FEATURE:
<223> OTHER INFORMATION: PERV-B; 794-2823 bp, Y12239

<400> SEQUENCE: 5

```
cagtctatgt tagacgccac cgtgcaggaa acctcgagac tcggtggaag ggcccttatc       60
tcgtactttt gaccacacca acggctgtga aagtcgaagg aatctccacc tggatccatg      120
catcccacgt taagctggcg ccacctcccg actcggggtg gagagccgaa aagactgaga      180
atccccttaa gcttcgcctc catcgcctgg ttccttactc taacaataac tccccaggcc      240
agtagtaaac gccttataga cagctcgaac ccccatagac ctttatccct tacctggctg      300
attattgacc ctgatacggg tgtcactgta aatagcactc gaggtgttgc tcctagaggc      360
acctggtggc ctgaactgca tttctgcctc cgattgatta ccccgctgt taaaagcaca      420 cctcccaacc tagtccgtag ttatgggttc tattgctgcc caggcacaga gaaagagaaa      480
tactgtgggg gttctgggga atccttctgt aggagatgga gctgcgtcac ctccaacgat      540
ggagactgga aatggccgat ctctctccag gaccgggtaa aattctcctt tgtcaattcc      600
ggcccgggca agtacaaagt gatgaaacta tataaagata agagctgctc cccatcagac      660
ttagattatc taaagataag tttcactgaa aaggaaaaac aggaaaatat tcaaaagtgg      720
ataaatggta tgagctgggg aatagttttt tataaatatg gcggggagc agggtccact      780 ttaaccattc gccttaggat agagacgggg acagaacccc ctgtggcagt gggacccgat      840
```

-continued

```
aaagtactgg ctgaacaggg gcccccggcc ctggagccac cgcataactt gccggtgccc    900
caattaacct cgctgcggcc tgacataaca cagccgccta gcaacggtac cactggattg    960
attcctacca acacgcctag aaactcccca ggtgttcctg ttaagacagg acagagactc   1020
ttcagtctca tccagggagc tttccaagcc atcaactcca ccgaccctga tgccacttct   1080
tcttgttggc tttgtctatc ctcagggcct ccttattatg aggggatggc taaagaagga   1140
aaattcaatg tgaccaaaga gcatagaaat caatgtacat gggggtcccg aaataagctt   1200
accctcactg aagtttccgg gaaggggaca tgcataggaa aagctccccc atcccaccaa   1260
cacctttgct atagtactgt ggtttatgag caggcctcag aaaatcagta tttagtacct   1320
ggttataaca ggtggtgggc atgcaatact gggttaaccc cctgtgtttc cacctcagtc   1380
ttcaaccaat ccaaagattt ctgtgtcatg gtccaaatcg tcccccgagt gtactaccat   1440
cctgaggaag tggtccttga tgaatatgac tatcggtata accgaccaaa aagagaaccc   1500
gtatccctta ccctagctgt aatgctcgga ttagggacgg ccgttggcgt aggaacaggg   1560
acagctgccc tgatcacagg accacagcag ctagagaaag gacttggtga gctacatgcg   1620
gccatgacag aagatctccg agccttagag gagtctgtta gcaacctaga agagtccctg   1680
acttctttgt ctgaagtggt tctacagaac cggaggggat tagatctgct gtttctaaga   1740
gaaggtgggt tatgtgcagc cttaaaagaa gaatgttgct tctatgtaga tcactcagga   1800
gccatcagag actccatgag caagcttaga gaaaggttag agaggcgtcg aaggaaaga   1860 gaggctgacc agggtggtt tgaaggatgg ttcaacaggt ctccttggat gaccaccctg   1920
ctttctgctc tgacgggacc cctagtagtc ctgctcctgt tacttacagt tgggccttgc   1980
ttaattaata ggtttgttgc ctttgttaga gaacgagtga gtgcagtcca             2030

<210> SEQ ID NO 6
<211> LENGTH: 306
<212> TYPE: DNA
<213> ORGANISM: Sus scrofa
<220> FEATURE:
<223> OTHER INFORMATION: G1-3' Locus

<400> SEQUENCE: 6
gtggggttaa tgattggggc tatatctatg gaagtgccta ttcgatccct agcctgttgc     60
attggattaa ggattcagtg ttttttgtagc tgtggtgcag gtcacagctc tggctcacgt    120
taggtctctg gcctgggact tccatatact gtgagtgtgg ctggaaaaaa atctgtaaat    180
tgttttgttt agtatggcca ttttagcaat attaaatgtt ttcaatccaa aatcatcttt    240
ccatttattt gtatcatctc attcatcaat gttttatagt tttcagcata caggtccttt    300
acctca                                                               306

<210> SEQ ID NO 7
<211> LENGTH: 323
<212> TYPE: DNA
<213> ORGANISM: Sus scrofa
<220> FEATURE:
<223> OTHER INFORMATION: G2-3' Locus

<400> SEQUENCE: 7
gagggcttca ttattgtgtc ctgaactgca ggtcaaaaac agatcctaaa agagagactg     60
catgtcataa aaacacacaa ggtaatttta cctttaaaag ggggacaag gaggcgctct    120 gttctgctaa caaaggcccc taggctttat cccacaatac ttttattaag gaaggtgact    180
```

```
tgtttaggta agtgagcaaa agcaggcttg gggagtatcg aagcaatcac ttagtgagac      240
ttagggagac taatagcaat gaaaatcaca ggtgtatgca tctaggatat agcgtagctg      300
cttaaagaac agtgtagtac agc                                              323
```

<210> SEQ ID NO 8
<211> LENGTH: 336
<212> TYPE: DNA
<213> ORGANISM: Sus scrofa
<220> FEATURE:
<223> OTHER INFORMATION: G3-3' Locus

<400> SEQUENCE: 8

```
cctttctttt cttttctgcc tcagcatgtc atccaccggc ggaccggata ctttgtttat      60
cttgaaactg tgtgttaaca tttagcacaa catttaaagg acagttggaa tctaaaacaa     120
aattccaaca agaaagcaa aacacagagg aagtaaaaac tcttgcaact tctgtttttc      180
aacaatactt ctgagttccc tgggggcaca gcaagttatg gatccacggt gtcactgcag     240
aggctcgggt caccgcgtga cgcagatttg acctctggcc tgggaacttc cacgtggaaa     300
gaaaagcttc ctgtgattgt ttccgtgttt cttttc                                336
```

<210> SEQ ID NO 9
<211> LENGTH: 328
<212> TYPE: DNA
<213> ORGANISM: Sus scrofa
<220> FEATURE:
<223> OTHER INFORMATION: G4-3' Locus

<400> SEQUENCE: 9

```
gaactcctct aaggttttga tatgagaact tctgaggtaa atcactagag aaaaaataac      60
atatttgcaa tggtggtaaa gataaaagaa cagtatagat tttcagagtt ttgggatatc     120
taccagtata ctgcagttga ccctacatcc accctgtcag gctgactctg tcaaccaaac     180
ctaagccatt aaatatcttc aggggggtgga aaatgggaac ccacatgtag cttgtccatg    240
gtccaggaat aaccatcacc atgacctcta ttgaagaaaa atccacctct ggagttttct     300
actctgaagt caaaagttca gctccaac                                         328
```

<210> SEQ ID NO 10
<211> LENGTH: 262
<212> TYPE: DNA
<213> ORGANISM: Sus scrofa
<220> FEATURE:
<223> OTHER INFORMATION: G5-3' Locus

<400> SEQUENCE: 10

```
cccccaaaag aaagaagaat gcatatttgt cccaatcctg attcctatct gaaaacctct      60
ttttctcctt tttactgtaa acccccttgc aattctttct aaaaggtggt tgggtgggga    120
cagtcttaaa ggcatctgtc tgctgtgacc ctcttctgcc tggcaaagca atagctattt     180
ttctctcctt tacccaaaac tctgtctctg cgtttcgatt cagcaccgtc agacagaggc     240
cgagttccag caacaggtct ga                                               262
```

<210> SEQ ID NO 11
<211> LENGTH: 288
<212> TYPE: DNA
<213> ORGANISM: Sus scrofa
<220> FEATURE:
<223> OTHER INFORMATION: G5-3' Locus

<400> SEQUENCE: 11

-continued

```
tgatgcagca gaaatgattc cgactaggaa tcatgagttt gagggtttga tccctggcct      60
tgctcagtgg gttaaggatc cggcattgcc ctgagctgtg gcgtagatcg cagatgcagc     120
gatctggcat tgctgtggct gtggcgtggg ctggcggata cagctccaat tagacccta     180 gcctgggaac ctccatgtgc cacaggttcg gccctaaaaa gacaaaaaaa aaaaggtatt    240
attttatttg tggtgttttg gaggtgccta tttccctaaa cctcacca                 288
```

<210> SEQ ID NO 12
<211> LENGTH: 315
<212> TYPE: DNA
<213> ORGANISM: Sus scrofa
<220> FEATURE:
<223> OTHER INFORMATION: G7-3' Locus

<400> SEQUENCE: 12

```
atgtgcacgt gtgtgcatgt gaagaataag acaaattcca tcatcagcaa gtcacttaat     60
ttctctgcga cttcattttc actcccataa acagttattt cttaaagtat tgtaatgatt    120
agagaaaatt tactttaaat tcttgtcact cagtggttag gctcttgtaa atgttagtt     180 attgtcattc ttccgtgaga atgttgtct gacttcaatt ctgttgctaa tctactgagt     240
tggatgtggg gatgctcatt cctattgact attcattgaa ttgaatgttt tggatccagc    300
tcctatgtaa gaaat                                                    315
```

<210> SEQ ID NO 13
<211> LENGTH: 316
<212> TYPE: DNA
<213> ORGANISM: Sus scrofa
<220> FEATURE:
<223> OTHER INFORMATION: G8-3' Locus

<400> SEQUENCE: 13

```
tggtatgttc ccccaaacct ggtcttttgg ttggcaacaa attaatcaca gttggcacat     60
cagatagcat gggtgttact cctgtcatag gtgatctgcg gaccccttcc tagaattaag    120
ttgtcttgtt ctgagacagt aggtgtggcc attcaggtac tacagtaaca gcccaggttt    180
gtgggtgcca ggacctgcca gctcccatgc caagtgttat ctatccgtca gggcctgctg    240
tgagtgcctg ttcacgacgt tgctctttca ggtggatctg tgtacacagg ctccgtggag    300
gtcctcttca tgtcaa                                                   316
```

<210> SEQ ID NO 14
<211> LENGTH: 465
<212> TYPE: DNA
<213> ORGANISM: Sus scrofa
<220> FEATURE:
<223> OTHER INFORMATION: G9-3' Locus

<400> SEQUENCE: 14

```
ccaccaaagg aaaatacaac agaaccaaag aaaaaaacca aaggcattgc taatctgcca     60
tctgcagcaa tgatgtagga aaataaacga gagctaaaca aaacaaaaca aaacgccttt   120
aaacaaaaaa gtcttctttt gagacagaag gaaagctctg tctcccaagg ccacagtcat   180
gttttccgtg tttgtgctat ggtgtgacca gggcctcaga gtcctgttgg ggggcctgtc   240 ccttttttatg caacatggct taatctgtct ccatcatttc ccagagtcag atgaaaccgg   300
cttaaaatgc caaggcttga cttcagctgt gtgggcccct gtcttccaag ccacaacatc   360
tgaacgcagc ctcctcccag gcaaagaaac agtcaataag gaaataccat agttaggctc   420
```

```
tttgcaactt gctcgaagtg tgaggcagcc gcttcatttc ctgat              465
```

```
<210> SEQ ID NO 15
<211> LENGTH: 309
<212> TYPE: DNA
<213> ORGANISM: Sus scrofa
<220> FEATURE:
<223> OTHER INFORMATION: G10-3' Locus

<400> SEQUENCE: 15
tctagtcaac tctgctccct cctgctagga ttataaagag aaaactacac agagactaaa    60
tccctacaat gatagcctta ggatcatgtt tgaaataatg taaacaaaaa tttgagaaga   120
gaatgaatga agatggaata gtgtgtaagc aatgagattg gtgcttttta gatctctatt   180
atatgtctgg caaaaaaaga tgcatcatgt atttattgtg tacatattgc atatgaggaa   240
ctgtgttagg caatgtatga gacaccgtaa ataattagtt gaggagttcc cattgtggca   300
cagtggaaa                                                          309
```

```
<210> SEQ ID NO 16
<211> LENGTH: 374
<212> TYPE: DNA
<213> ORGANISM: Sus scrofa
<220> FEATURE:
<223> OTHER INFORMATION: G11-3' Locus

<400> SEQUENCE: 16
ctttgcctaa acacccagct tgttctcttt ttctccgcgc tcgccttaca atttttatct    60
agctttgaaa gctatatgcg tattataaat acataaggct atgtacagat tacaaacata   120
cacacaatta aatacatgta ataaaattgc atacttggag tatttcatta gattatacca   180
gcttgtgaaa catatattat cacacttaag catttacaaa aagtggattc taagctaagg   240
aagaataact ttaggtaaaa acagtcataa taattctgtg agaaattatc tcttacctct   300
atagctgcat cttttcattc tgaactcata attaagttgc cttgttctag aactctgctc   360
tgattacatt agaa                                                     374
```

```
<210> SEQ ID NO 17
<211> LENGTH: 276
<212> TYPE: DNA
<213> ORGANISM: Sus scrofa
<220> FEATURE:
<223> OTHER INFORMATION: G12-3' Locus

<400> SEQUENCE: 17
gtcttgatac cctaatgtga atgagtaaaa attcttcttt cttaggagga tgtaagagaa    60
gtgacaaagg gatggttagg gtggagggaa ctgaaagtca cagctctcta tcgcctggaa   120
ataacattta ctcctttcaa agttagcata gacctggccc agaaagccct acattagact   180
taattttcta ggtgttttcc agagttgtat ggaatttaaa attatgactt tgctattgag   240
aaatattaga agagccagga caaatcaaag caacca                             276
```

```
<210> SEQ ID NO 18
<211> LENGTH: 280
<212> TYPE: DNA
<213> ORGANISM: Sus scrofa
<220> FEATURE:
<223> OTHER INFORMATION: G13-3' Locus

<400> SEQUENCE: 18
cacatcacac caatcagaat ggccatcatt catcagtcca caaataacaa atgctggagc    60
```

```
aggtgtggag aaaacggaac cctcctgcac tgttggtggg aatggaaact ggtacagcca    120
ctatggagaa ctgtatggaa gtaccttaga aatctattca tagaactacc atatgatcca    180
gcaattccac tcacgggcat atatttggac aaaatgttcc ttcaaaaaga cacatgcacc    240
cacatgttca ctgcagctct atttacaata gccaagacaa                         280

<210> SEQ ID NO 19
<211> LENGTH: 274
<212> TYPE: DNA
<213> ORGANISM: Sus scrofa
<220> FEATURE:
<223> OTHER INFORMATION: G14-3' Locus

<400> SEQUENCE: 19
caagctggca ctatgttctg taaactccag ttcccctag ccaggtagcc cccagcagta     60
ggacaggtgt ccagccatta ttgcacctgt gtggtggggg gaagtggggg ggtgagaggg   120
gaggccagtg gggagcaaag gtgaggctgt gtgcatgctt ttcctggccc ctggtatatt   180
cagatccgcc cccatggggt cgatgtgaag tcagggcccg tggatctcta tgactcttac   240
atggtttatg gctctgggga ctgggttttt tttg                               274

<210> SEQ ID NO 20
<211> LENGTH: 231
<212> TYPE: DNA
<213> ORGANISM: Sus scrofa
<220> FEATURE:
<223> OTHER INFORMATION: G15-3' Locus

<400> SEQUENCE: 20
gctccatagg tttagtaagt aatattctaa attcatagaa tatggagaat taatttctga    60
ggatatcaga taatattttg ttaaaatata tactttgcct tttagaagaa ttgcaatgtc   120
caccatggtc ttgcattgtg gtggctggtt gctgacatat ggtcaggat atattgcttg   180 ggttggattt aagaatatag actacttggc agagttcaaa gggaatgaca t            231

<210> SEQ ID NO 21
<211> LENGTH: 353
<212> TYPE: DNA
<213> ORGANISM: Sus scrofa
<220> FEATURE:
<223> OTHER INFORMATION: G16-3' Locus

<400> SEQUENCE: 21
gctccaccat ctgacctcat agatttattc gcttactttc tgccactttc acctgccaat    60
agtatgttag ctctctgaag gcagggactc tgattacttt gctcttgtaa tacctgcccc   120
taggacagtg cctggccaac acttttggtg cagtaaaagc tgcaggaatt gaatgccttt   180
tgaactattt cctctttatc tttctaagca gctgttcttt ctgaccaatt gatggcactc   240
aaatactttc tacgcattga aacagtgtcc taagttttgt taatgggacc cacaggggct   300 cccctgctg agacctgaat tttttaaaat gatgttcctg ctttgggtct ttg           353

<210> SEQ ID NO 22
<211> LENGTH: 534
<212> TYPE: DNA
<213> ORGANISM: Sus scrofa
<220> FEATURE:
<223> OTHER INFORMATION: G17-3' Locus

<400> SEQUENCE: 22
```

```
gtgactgtga aataagattc tgaacaatta atcttaaagc taaaatagta tgaagagcaa      60
atggaaatta tagatgtctg taagtttctt atattagtcc cattttttctg gtttgtatta    120 tataaaataa ttaagctttc ctttaaaaaa atccatcatg attatactgg gaaaatgtt     180 ggtacctgcc ttttagaaat agttttaaat atactctgtt ggcttttat aactgattga      240 attctcagac atattttaag taaattaatt aaaaatgttt gttttaagag cttgtgttgg     300
aaaatgattc ttacatttct gcaagaaaaa aatctgtggg tagaacaaaa aatcagataa    360
ccctgttttt ttttttttta aatccttatt ctagcaatag tcttaataaa accgcaaagc    420
atttgttgga aaggatctga gggtcatgta gttaacttcc taccagacat ataaatcttc    480
tgacgtcacc caaatagtca tgcagcctcc cttgaacatt gccactaaca ctgg           534
```

```
<210> SEQ ID NO 23
<211> LENGTH: 396
<212> TYPE: DNA
<213> ORGANISM: Sus scrofa
<220> FEATURE:
<223> OTHER INFORMATION: G18-3' Locus

<400> SEQUENCE: 23
tggtttgtcc catttgtgtg ctagccacct aaagaaaga cacgtccttg agaaaattac       60
cctgccattg acagttgctt gaaacaacag ctcctttacc tctctctcgc cttcttttca    120
tctccttctc tctagctctc tcactctccc ctttgccccc cttcaatttc tcctgtatcc    180
tcctgctaca attcgacctg gggtaataat ggatcaaata tattagccaa agaaatgctc     240
caagttatcc cccagccttt tctccctgtc atcctaggtc tgatcgcata taaattccgt     300
ggtcctggta gactctgtgc tgtgtgggag acacccaact aggtcagcct taaacatact    360
ccatatcatc cttctatgga acgctgacac tcaatg                              396
```

```
<210> SEQ ID NO 24
<211> LENGTH: 250
<212> TYPE: DNA
<213> ORGANISM: Sus scrofa
<220> FEATURE:
<223> OTHER INFORMATION: G19-3' Locus

<400> SEQUENCE: 24
ccactctggt tacacaaaga aagaaatgtc tttataaaaa agggttccgt cttcatcttg       60
gctgttttaa aatacagatt tatcccaaaa tgttttctta gtgctctaac tacctccaaa    120
tgaagcaccc tgcaatatta tgactttgga tataatgtga ccagtgattg gccaaccctc    180
acaagacctc ttatttcatt aacctagcag ttgttacccc attcatgcaa ctgaagtttt    240
tggacccctc                                                          250
```

```
<210> SEQ ID NO 25
<211> LENGTH: 359
<212> TYPE: DNA
<213> ORGANISM: Sus scrofa
<220> FEATURE:
<223> OTHER INFORMATION: G20-3' Locus

<400> SEQUENCE: 25
gccttgctct tatgcttcag gatccatgag ctctagatta ggtcgttgac cgataaagga       60
tatttggtgg ccatggccct gactctgggg taggccagca tgtgtagctc ggattgacca    120
gcacgctagg aacttctcca aaccatgggt ggcatcccca acatcaggag caaatctact    180
tttgtcgtag agcacataca gctggcctgc tcttaggatt atgcagacat tgaagtaacg    240
```

```
actcattgca tctttgccca gcgcatatct tccgacttga attttatccg aaagaatata      300
tccattgaaa cactatcact tgaaaacagg atcgactctg tggacttttc cacatcaga      359
```

<210> SEQ ID NO 26
<211> LENGTH: 391
<212> TYPE: DNA
<213> ORGANISM: Sus scrofa
<220> FEATURE:
<223> OTHER INFORMATION: G21-3' Locus

<400> SEQUENCE: 26

```
agttggtcgc aatatcccaa gatggttaaa agaaattctt tctgcaaaag aggaactaga       60
gtaaagaggt taagtgagtg gcctgactga ggatgagagc taagcaaccc aacactttgc      120
cctttggctg tgtcttcctc gtacatcttg tctaaggatg aggccagttg tattctgtga      180
ggagcgttgt gtggacctca tacacggaca acatgtcact gagtgcaaat gattttagta      240
aacagaaagg caaggtcata cctcagctgc accccagaag agctctgatc tcaagggaaa      300
atttgtaaaa cagcttctct gggtaaaagg gaaatgttgg gggctctgag ctgctacacc      360
tggaagagct gcatgatctg tgggcaaaga g                                    391
```

<210> SEQ ID NO 27
<211> LENGTH: 334
<212> TYPE: DNA
<213> ORGANISM: Sus scrofa
<220> FEATURE:
<223> OTHER INFORMATION: G22-3' Locus

<400> SEQUENCE: 27

```
gccatggcag ctaagaagat aaacttaata caaggctagc atacatagga aaagccttgc       60
taagtgagat gaaatcctag gggctactta taaaaggga cagattcaaa tagacagaag      120
tcaagtatgt gcatgaggtg gggcactca aggaagtcaa agaaaatttg aaactgaaaa      180
gacatttgca attttaaagt ctttaatgag tgaggaattt caacaaatca acttttttaaa     240 ggcaaacaga tgggaaatga tgtgacatat aggcccacaat acaaagggag gagagataaa    300
tatgcctatt gacatcacta ctaagaatat gcag                                 334
```

<210> SEQ ID NO 28
<211> LENGTH: 415
<212> TYPE: DNA
<213> ORGANISM: Sus scrofa
<220> FEATURE:
<223> OTHER INFORMATION: G23-3' Locus

<400> SEQUENCE: 28

```
caattccaaa cgtgttctcc ttcgtggaga aggcggattt ggcatgaaaa tgccttgtgt       60
gcacaagccc cagtcaccca cactgagcca cctaggagg gacctaccga aggcatatct      120
ccgaaacagc acaaaactcg cttctggaag ctgcattctg caaagggaaa ctgtgctcgg     180
ggaacaaacc tcaccccaa tgcgttttg ctctggaacg cagtgcttgc ctatttctcc       240
cctagcccta ggctcccttt agggccaagg agggtcgggc tgcctctggc tccgtgggca    300
cttctgctag gctggtgctc tctggagctt gaatccaaat caaatgtgtt ctccttcagg    360
gagaaggctg atttatcatg aaaaggcctt tgttgcatgg agaaagctga tttgg         415
```

<210> SEQ ID NO 29
<211> LENGTH: 377
<212> TYPE: DNA

<213> ORGANISM: Sus scrofa
<220> FEATURE:
<223> OTHER INFORMATION: G24-3' Locus
<220> FEATURE:
<221> NAME/KEY: modified_base
<222> LOCATION: (275)
<223> OTHER INFORMATION: n = g, a, c or t

<400> SEQUENCE: 29

| | | | | | |
|---|---|---|---|---|---|
| ctatacttta | atccacagct | tgtcactctg | ttgcaaagat | aagcttttac | cctatgaaaa | 60 |
| attctaagaa | aaatatgaaa | aagtgttgaa | gcatgaaatt | gtatggtaat | taaaagactt | 120 |
| ttgcaggaaa | cacttctaaa | tgccaaatgc | tataaagtag | taatagttca | aatggaagga | 180 |
| aagtgctaac | aaataaaatg | attcatagaa | atgtcttggt | tacaggattc | catagtagaa | 240 |
| gtaaattgtt | aaaccaatga | cgtgaagtgt | tcaanttctt | gtgaatgttc | ttaaatggtt | 300 |
| tggggcaaac | agaattgata | ttcccttggt | tatcagtaat | catcatttgt | tcagtctgtc | 360 |
| aacaaatatt | tgttgag | | | | | 377 |

<210> SEQ ID NO 30
<211> LENGTH: 357
<212> TYPE: DNA
<213> ORGANISM: Sus scrofa
<220> FEATURE:
<223> OTHER INFORMATION: G25-3' Locus
<220> FEATURE:
<221> NAME/KEY: modified_base
<222> LOCATION: (34)
<223> OTHER INFORMATION: n = g, a, c or t

<400> SEQUENCE: 30

| | | | | | |
|---|---|---|---|---|---|
| cattttcaaa | ccaagccagg | cttccccaca | caangagccc | gcgcttggag | tgccttgcac | 60 |
| gcagtgggaa | atcccttgca | cacacccggg | gccaagggag | ccctggggag | ccaggggcct | 120 |
| gtctggcctg | agcttgccag | aggcctacgt | gcgaccacgg | ctagggtggc | ttggcacatc | 180 |
| acaaccacat | tggggctggc | gttggttccc | tgagtaggcc | agcgctcgcc | aggagacagc | 240 |
| cgtccgcctc | ttctttggtc | gagtgtgtca | gagtgccccc | aggccaggat | tgccctggct | 300 |
| cagcagaggc | cctgcaggcc | gcttgggaca | ctatgggttt | tcacaccaaa | tcaggct | 357 |

<210> SEQ ID NO 31
<211> LENGTH: 227
<212> TYPE: DNA
<213> ORGANISM: Sus scrofa
<220> FEATURE:
<223> OTHER INFORMATION: G26-3' Locus

<400> SEQUENCE: 31

| | | | | | |
|---|---|---|---|---|---|
| aagggatag | acatttggag | gagctaagca | ctaggaatgc | aggttacctt | actagattta | 60 |
| agtgactaaa | gtggagaatt | ttgggttgtt | ttctcttttg | taacacctct | cttcctagga | 120 |
| ttctcatgca | tgaaaagtag | gtacactaac | attgaaaaaa | agataaatta | tttatactat | 180 |
| tagcatgtgt | aatgactcac | atgtttacaa | gcaaccagtg | aaaatgc | | 227 |

<210> SEQ ID NO 32
<211> LENGTH: 383
<212> TYPE: DNA
<213> ORGANISM: Sus scrofa
<220> FEATURE:
<223> OTHER INFORMATION: G27-3' Locus

<400> SEQUENCE: 32

| | | | | | |
|---|---|---|---|---|---|
| gataagccac | cacccatcag | tattgtactc | tgctatgtgt | gaaccagtca | tagtatatga | 60 |

```
acctagaggc tctcgtaaaa aataatttct caaggaggta ggcattttc tttctttctg      120 ttttttgtt tttgttttt tttttagggg ggtgctgtct ttttagggcc acacccactg      180
catacggagg gtcccaggct agggtcaaa tcagagccat agctaccggc ctacaccaca      240
gccacagcaa tacaggattt gagccacgtc tgtgacctac accacagctc atggcaatgc      300
tggaacctta agccactgag agaggccagg gatcaaaccg tgtcctcatg gatactaact      360
gggttcatta ctgctgagcc atg                                              383

<210> SEQ ID NO 33
<211> LENGTH: 463
<212> TYPE: DNA
<213> ORGANISM: Sus scrofa
<220> FEATURE:
<223> OTHER INFORMATION: G28-3' Locus
<220> FEATURE:
<221> NAME/KEY: modified_base
<222> LOCATION: (150)
<223> OTHER INFORMATION: n = g, a, c or t

<400> SEQUENCE: 33
tcagcccaag actactggtc agactataat ttgattgtaa aataaaacat cataaaagta       60
aattgataat aaatgtttct tgtcagcaaa catgagtttt cccgaggtgg acaatgagca      120
cccaattcat atcacccttt ccaccccctgn aacctgccca cttgggaagc aacctgggca      180
gggagggccc tttggacagc agagactttc agcagttgtc ttgcactaca gggacattaa      240
tttaagcccg tcattgcagt ggataaacaa gagagcaaca catggtgacc tatcaagaaa      300
tgcccatctt ggtcaccagc agtatgttgc aattactagt tttaaagagt cccactggca      360
tatcatactg agagtgactg ctgccatcag gtttcttctt agagtcaggg gctgattaac      420
agaacaactc tgaagagtga agtgctgtaa ccttagatgt ggc                        463

<210> SEQ ID NO 34
<211> LENGTH: 369
<212> TYPE: DNA
<213> ORGANISM: Sus scrofa
<220> FEATURE:
<223> OTHER INFORMATION: G29-3' Locus
<220> FEATURE:
<221> NAME/KEY: modified_base
<222> LOCATION: (71)
<223> OTHER INFORMATION: n = g, a, c or t

<400> SEQUENCE: 34
atccccagcc aaaacatctg gctgtgggca taggttgcaa ctgtggctta gattcggtcc       60
ctggccaggg naacttccct atgccattgg ctgcaaccat taaaaaaaat gcatcacttt      120
tatgaataat tattatcaac tagcaagact aaaattagat taatacagaa tttgttaaga      180
aaacatgata aatgaaagaa acaatgtatt cattttcata tttgccagaa agaatgggta      240
aaatccagta tgttttcctg attttaaaaa aaaagtaata gacttttaaa aaaaagtaat      300
tactttacaa aaaaaagtaa tagagagaaa tgttcttaac tagaattgtc ttctcaactc      360
actgacaat                                                              369

<210> SEQ ID NO 35
<211> LENGTH: 316
<212> TYPE: DNA
<213> ORGANISM: Sus scrofa
<220> FEATURE:
<223> OTHER INFORMATION: G30-3' Locus
```

```
<400> SEQUENCE: 35
aaagcagtgt tgagtaaagg gtagctttta tcattaacaa ccattatttc cagagcaatc      60
tctccccttc ttaaagcatg caggaggagg ggctcagggg agaggaagcc aaaagagagg     120
gggagaagca agatagagt atttattaag catctattat gtgccacaca tttactcagt     180
gattcctgac atataaatac tccctgaggg agaataaaat gtatagcata tatttctcct     240
tctctaaaat tctcccttaa cttcactcta acccttagac caaattctgc aggagcccaa     300
acacagaaaa atcacg                                                     316

<210> SEQ ID NO 36
<211> LENGTH: 20
<212> TYPE: DNA
<213> ORGANISM: Artificial Sequence
<220> FEATURE:
<223> OTHER INFORMATION: 5' G1 Primer

<400> SEQUENCE: 36
gtggggttaa tgattggggc                                                  20

<210> SEQ ID NO 37
<211> LENGTH: 25
<212> TYPE: DNA
<213> ORGANISM: Artificial Sequence
<220> FEATURE:
<223> OTHER INFORMATION: 3' G1 Primer

<400> SEQUENCE: 37
gcaatgaggt aaaggacctg tatgc                                            25

<210> SEQ ID NO 38
<211> LENGTH: 23
<212> TYPE: DNA
<213> ORGANISM: Artificial Sequence
<220> FEATURE:
<223> OTHER INFORMATION: 5' G2 Primer

<400> SEQUENCE: 38
gagggcttca ttattgtgtc ctg                                              23

<210> SEQ ID NO 39
<211> LENGTH: 24
<212> TYPE: DNA
<213> ORGANISM: Artificial Sequence
<220> FEATURE:
<223> OTHER INFORMATION: 3' G2 Primer

<400> SEQUENCE: 39
gctgtactac actgttcttt aagc                                             24

<210> SEQ ID NO 40
<211> LENGTH: 23
<212> TYPE: DNA
<213> ORGANISM: Artificial Sequence
<220> FEATURE:
<223> OTHER INFORMATION: 5' G3 Primer

<400> SEQUENCE: 40
cctttctttt cttttctgcc agc                                              23

<210> SEQ ID NO 41
<211> LENGTH: 24
<212> TYPE: DNA
<213> ORGANISM: Artificial Sequence
```

```
<220> FEATURE:
<223> OTHER INFORMATION: 3' G3 Primer

<400> SEQUENCE: 41
gaaaagaaac acggaaacaa tcac                                          24

<210> SEQ ID NO 42
<211> LENGTH: 20
<212> TYPE: DNA
<213> ORGANISM: Artificial Sequence
<220> FEATURE:
<223> OTHER INFORMATION: 5' G4 Primer

<400> SEQUENCE: 42
gaactcctct aaggttttga                                               20

<210> SEQ ID NO 43
<211> LENGTH: 20
<212> TYPE: DNA
<213> ORGANISM: Artificial Sequence
<220> FEATURE:
<223> OTHER INFORMATION: 3'G4 Primer

<400> SEQUENCE: 43
tgttggagct gaactttga                                                20

<210> SEQ ID NO 44
<211> LENGTH: 22
<212> TYPE: DNA
<213> ORGANISM: Artificial Sequence
<220> FEATURE:
<223> OTHER INFORMATION: 5' G5 Primer

<400> SEQUENCE: 44
cccccaaaag aagaagaat gc                                             22

<210> SEQ ID NO 45
<211> LENGTH: 22
<212> TYPE: DNA
<213> ORGANISM: Artificial Sequence
<220> FEATURE:
<223> OTHER INFORMATION: 3' G5 Primer

<400> SEQUENCE: 45
tcagacctgt tgctggaact cg                                            22

<210> SEQ ID NO 46
<211> LENGTH: 22
<212> TYPE: DNA
<213> ORGANISM: Artificial Sequence
<220> FEATURE:
<223> OTHER INFORMATION: 5' G6 Primer

<400> SEQUENCE: 46
tgatgcagca gaaatgattc cg                                            22

<210> SEQ ID NO 47
<211> LENGTH: 23
<212> TYPE: DNA
<213> ORGANISM: Artificial Sequence
<220> FEATURE:
<223> OTHER INFORMATION: 3' G6 Primer

<400> SEQUENCE: 47
tggtgaggtt tagggaaata ggc                                           23
```

```
<210> SEQ ID NO 48
<211> LENGTH: 24
<212> TYPE: DNA
<213> ORGANISM: Artificial Sequence
<220> FEATURE:
<223> OTHER INFORMATION: 5' G7 primer

<400> SEQUENCE: 48
atgtgcacgt gtgtgcatgt gaag                                           24

<210> SEQ ID NO 49
<211> LENGTH: 24
<212> TYPE: DNA
<213> ORGANISM: Artificial Sequence
<220> FEATURE:
<223> OTHER INFORMATION: 3' G7 Primer

<400> SEQUENCE: 49
atttctgaca taggagctgg atcc                                           24

<210> SEQ ID NO 50
<211> LENGTH: 22
<212> TYPE: DNA
<213> ORGANISM: Artificial Sequence
<220> FEATURE:
<223> OTHER INFORMATION: 5' G8 Primer

<400> SEQUENCE: 50
tggtatgttc ccccaaacct gg                                             22

<210> SEQ ID NO 51
<211> LENGTH: 24
<212> TYPE: DNA
<213> ORGANISM: Artificial Sequence
<220> FEATURE:
<223> OTHER INFORMATION: 3' G8 Primer

<400> SEQUENCE: 51
ttgacatgaa gaggacctcc acgg                                           24

<210> SEQ ID NO 52
<211> LENGTH: 25
<212> TYPE: DNA
<213> ORGANISM: Artificial Sequence
<220> FEATURE:
<223> OTHER INFORMATION: 5' G9 Primer

<400> SEQUENCE: 52
ccaccaaagg aaaatacaac agaac                                          25

<210> SEQ ID NO 53
<211> LENGTH: 18
<212> TYPE: DNA
<213> ORGANISM: Artificial Sequence
<220> FEATURE:
<223> OTHER INFORMATION: 3' G9 Primer

<400> SEQUENCE: 53
atcaggaaat gaagcggc                                                  18

<210> SEQ ID NO 54
<211> LENGTH: 24
<212> TYPE: DNA
<213> ORGANISM: Artificial Sequence
<220> FEATURE:
<223> OTHER INFORMATION: 5' G10 Primer
```

```
<400> SEQUENCE: 54
tctagtcaac tctgctccct cctg                                          24

<210> SEQ ID NO 55
<211> LENGTH: 21
<212> TYPE: DNA
<213> ORGANISM: Artificial Sequence
<220> FEATURE:
<223> OTHER INFORMATION: 3' G10 Primer

<400> SEQUENCE: 55
gtttccactg tgccacaatg g                                             21

<210> SEQ ID NO 56
<211> LENGTH: 18
<212> TYPE: DNA
<213> ORGANISM: Artificial Sequence
<220> FEATURE:
<223> OTHER INFORMATION: 5' G11 Primer

<400> SEQUENCE: 56
ctttgcctaa acacccag                                                 18

<210> SEQ ID NO 57
<211> LENGTH: 21
<212> TYPE: DNA
<213> ORGANISM: Artificial Sequence
<220> FEATURE:
<223> OTHER INFORMATION: 3' G11 Primer

<400> SEQUENCE: 57
attctaatgt aatcagagca g                                             21

<210> SEQ ID NO 58
<211> LENGTH: 25
<212> TYPE: DNA
<213> ORGANISM: Artificial Sequence
<220> FEATURE:
<223> OTHER INFORMATION: 5' G12 Primer

<400> SEQUENCE: 58
gtcttgatac cctaatgtga atgag                                         25

<210> SEQ ID NO 59
<211> LENGTH: 21
<212> TYPE: DNA
<213> ORGANISM: Artificial Sequence
<220> FEATURE:
<223> OTHER INFORMATION: 3' G12 Primer

<400> SEQUENCE: 59
tggttgcttt gatttgtcct g                                             21

<210> SEQ ID NO 60
<211> LENGTH: 24
<212> TYPE: DNA
<213> ORGANISM: Artificial Sequence
<220> FEATURE:
<223> OTHER INFORMATION: 5' G13 Primer

<400> SEQUENCE: 60
gcacatcaca ccaatcagaa tggc                                          24

<210> SEQ ID NO 61
```

```
<211> LENGTH: 22
<212> TYPE: DNA
<213> ORGANISM: Artificial Sequence
<220> FEATURE:
<223> OTHER INFORMATION: 3' G13 Primer

<400> SEQUENCE: 61
ttgggttgtt tccttgtctt gg                                              22

<210> SEQ ID NO 62
<211> LENGTH: 24
<212> TYPE: DNA
<213> ORGANISM: Artificial Sequence
<220> FEATURE:
<223> OTHER INFORMATION: 5' G14 Primer

<400> SEQUENCE: 62
caagctggca ctatgttctg taaa                                            24

<210> SEQ ID NO 63
<211> LENGTH: 21
<212> TYPE: DNA
<213> ORGANISM: Artificial Sequence
<220> FEATURE:
<223> OTHER INFORMATION: 3' G14 Primer

<400> SEQUENCE: 63
caaaaaaaac ccagtcccca g                                               21

<210> SEQ ID NO 64
<211> LENGTH: 19
<212> TYPE: DNA
<213> ORGANISM: Artificial Sequence
<220> FEATURE:
<223> OTHER INFORMATION: 5' G15 Primer

<400> SEQUENCE: 64
gctccatagg tttagtaag                                                  19

<210> SEQ ID NO 65
<211> LENGTH: 18
<212> TYPE: DNA
<213> ORGANISM: Artificial Sequence
<220> FEATURE:
<223> OTHER INFORMATION: 3' G15 Primer

<400> SEQUENCE: 65
atgtcattcc ctttgaac                                                   18

<210> SEQ ID NO 66
<211> LENGTH: 22
<212> TYPE: DNA
<213> ORGANISM: Artificial Sequence
<220> FEATURE:
<223> OTHER INFORMATION: 5' G16 Primer

<400> SEQUENCE: 66
gctccaccat ctgacctcat ag                                              22

<210> SEQ ID NO 67
<211> LENGTH: 20
<212> TYPE: DNA
<213> ORGANISM: Artificial Sequence
<220> FEATURE:
<223> OTHER INFORMATION: 3' G16 Primer

<400> SEQUENCE: 67
```
caaagaccca aagcaggaac                    20

<210> SEQ ID NO 68
<211> LENGTH: 25
<212> TYPE: DNA
<213> ORGANISM: Artificial Sequence
<220> FEATURE:
<223> OTHER INFORMATION: 5' G17 Primer

<400> SEQUENCE: 68
gtgactgtga aataagattc tgaac               25

<210> SEQ ID NO 69
<211> LENGTH: 21
<212> TYPE: DNA
<213> ORGANISM: Artificial Sequence
<220> FEATURE:
<223> OTHER INFORMATION: 3' G17 Primer

<400> SEQUENCE: 69
ccagtgttag tggcaatgtt c                   21

<210> SEQ ID NO 70
<211> LENGTH: 18
<212> TYPE: DNA
<213> ORGANISM: Artificial Sequence
<220> FEATURE:
<223> OTHER INFORMATION: 5' G18 Primer

<400> SEQUENCE: 70
tggtttgtcc catttgtg                       18

<210> SEQ ID NO 71
<211> LENGTH: 19
<212> TYPE: DNA
<213> ORGANISM: Artificial Sequence
<220> FEATURE:
<223> OTHER INFORMATION: 3' G18 Primer

<400> SEQUENCE: 71
cattgagtgt cagcgttcc                      19

<210> SEQ ID NO 72
<211> LENGTH: 23
<212> TYPE: DNA
<213> ORGANISM: Artificial Sequence
<220> FEATURE:
<223> OTHER INFORMATION: 5' G19 Primer

<400> SEQUENCE: 72
ccactctggt tacacaaaga aag                 23

<210> SEQ ID NO 73
<211> LENGTH: 20
<212> TYPE: DNA
<213> ORGANISM: Artificial Sequence
<220> FEATURE:
<223> OTHER INFORMATION: 3' G19 Primer

<400> SEQUENCE: 73 gagggtcca aaacttcag                       20

<210> SEQ ID NO 74
<211> LENGTH: 18
<212> TYPE: DNA

```
<213> ORGANISM: Artificial Sequence
<220> FEATURE:
<223> OTHER INFORMATION: 5' G20primer

<400> SEQUENCE: 74
gccttgctct tatgcttc                                                    18

<210> SEQ ID NO 75
<211> LENGTH: 18
<212> TYPE: DNA
<213> ORGANISM: Artificial Sequence
<220> FEATURE:
<223> OTHER INFORMATION: 3' G20 Primer

<400> SEQUENCE: 75
tctgatgtgg aaaagtcc                                                    18

<210> SEQ ID NO 76
<211> LENGTH: 21
<212> TYPE: DNA
<213> ORGANISM: Artificial Sequence
<220> FEATURE:
<223> OTHER INFORMATION: 5' G21 Primer

<400> SEQUENCE: 76
agttggtcgc aatatcccaa g                                                21

<210> SEQ ID NO 77
<211> LENGTH: 24
<212> TYPE: DNA
<213> ORGANISM: Artificial Sequence
<220> FEATURE:
<223> OTHER INFORMATION: 3' G21 Primer

<400> SEQUENCE: 77
ctctttgccc acagatcatg cagc                                             24

<210> SEQ ID NO 78
<211> LENGTH: 24
<212> TYPE: DNA
<213> ORGANISM: Artificial Sequence
<220> FEATURE:
<223> OTHER INFORMATION: 5' G22 Primer

<400> SEQUENCE: 78
gccatggcag ctaagaagat aaac                                             24

<210> SEQ ID NO 79
<211> LENGTH: 24
<212> TYPE: DNA
<213> ORGANISM: Artificial Sequence
<220> FEATURE:
<223> OTHER INFORMATION: 3' G22 Primer

<400> SEQUENCE: 79
ctgcatattc ttagtagtga tgtc                                             24

<210> SEQ ID NO 80
<211> LENGTH: 24
<212> TYPE: DNA
<213> ORGANISM: Artificial Sequence
<220> FEATURE:
<223> OTHER INFORMATION: 5' G23 Primer

<400> SEQUENCE: 80
caattccaaa cgtgttctcc ttcg                                             24
```

```
<210> SEQ ID NO 81
<211> LENGTH: 24
<212> TYPE: DNA
<213> ORGANISM: Artificial Sequence
<220> FEATURE:
<223> OTHER INFORMATION: 3' G23 Primer

<400> SEQUENCE: 81
ccaaatcagc tttctccatg caac                                        24

<210> SEQ ID NO 82
<211> LENGTH: 24
<212> TYPE: DNA
<213> ORGANISM: Artificial Sequence
<220> FEATURE:
<223> OTHER INFORMATION: 5' G24 Primer

<400> SEQUENCE: 82
ctatacttta atccacagct tgtc                                        24

<210> SEQ ID NO 83
<211> LENGTH: 24
<212> TYPE: DNA
<213> ORGANISM: Artificial Sequence
<220> FEATURE:
<223> OTHER INFORMATION: 3' G24 Primer

<400> SEQUENCE: 83
ctcaacaaat atttgttgac agac                                        24

<210> SEQ ID NO 84
<211> LENGTH: 24
<212> TYPE: DNA
<213> ORGANISM: Artificial Sequence
<220> FEATURE:
<223> OTHER INFORMATION: 5' G25 Primer

<400> SEQUENCE: 84
cattttcaaa ccaagccagg cttc                                        24

<210> SEQ ID NO 85
<211> LENGTH: 21
<212> TYPE: DNA
<213> ORGANISM: Artificial Sequence
<220> FEATURE:
<223> OTHER INFORMATION: 3' G25 Primer

<400> SEQUENCE: 85
agcctgattt ggtgtgaaaa c                                           21

<210> SEQ ID NO 86
<211> LENGTH: 21
<212> TYPE: DNA
<213> ORGANISM: Artificial Sequence
<220> FEATURE:
<223> OTHER INFORMATION: 5' G26 Primer

<400> SEQUENCE: 86
aaggggatag acatttggag g                                           21

<210> SEQ ID NO 87
<211> LENGTH: 25
<212> TYPE: DNA
<213> ORGANISM: Artificial Sequence
<220> FEATURE:
```

<223> OTHER INFORMATION: 3' G26 Primer

<400> SEQUENCE: 87
gcattttcac tggttgcttg taaac                                    25

<210> SEQ ID NO 88
<211> LENGTH: 20
<212> TYPE: DNA
<213> ORGANISM: Artificial Sequence
<220> FEATURE:
<223> OTHER INFORMATION: 5' G27 Primer

<400> SEQUENCE: 88
gataagccac caccaatcag                                          20

<210> SEQ ID NO 89
<211> LENGTH: 21
<212> TYPE: DNA
<213> ORGANISM: Artificial Sequence
<220> FEATURE:
<223> OTHER INFORMATION: 3' G27 Primer

<400> SEQUENCE: 89
catggctcag cagtaatgaa c                                        21

<210> SEQ ID NO 90
<211> LENGTH: 24
<212> TYPE: DNA
<213> ORGANISM: Artificial Sequence
<220> FEATURE:
<223> OTHER INFORMATION: 5' G28 Primer

<400> SEQUENCE: 90
tcagcccaag actactggtc agac                                     24

<210> SEQ ID NO 91
<211> LENGTH: 25
<212> TYPE: DNA
<213> ORGANISM: Artificial Sequence
<220> FEATURE:
<223> OTHER INFORMATION: 3' G28 Primer

<400> SEQUENCE: 91
gccacatcta aggttacagc acttc                                    25

<210> SEQ ID NO 92
<211> LENGTH: 18
<212> TYPE: DNA
<213> ORGANISM: Artificial Sequence
<220> FEATURE:
<223> OTHER INFORMATION: 5' G29 Primer

<400> SEQUENCE: 92
atccccagcc aaaacatc                                            18

<210> SEQ ID NO 93
<211> LENGTH: 20
<212> TYPE: DNA
<213> ORGANISM: Artificial Sequence
<220> FEATURE:
<223> OTHER INFORMATION: 3' G29 Primer

<400> SEQUENCE: 93
attgtcagtg agttgagaag                                          20

-continued

<210> SEQ ID NO 94
<211> LENGTH: 24
<212> TYPE: DNA
<213> ORGANISM: Artificial Sequence
<220> FEATURE:
<223> OTHER INFORMATION: 5' G30 Primer

<400> SEQUENCE: 94
aaagcagtgt tgagtaaagg gtag                                          24

<210> SEQ ID NO 95
<211> LENGTH: 21
<212> TYPE: DNA
<213> ORGANISM: Artificial Sequence
<220> FEATURE:
<223> OTHER INFORMATION: 3' G30 Primer

<400> SEQUENCE: 95 cgtgatttt ctgtgtttgg g                                              21

<210> SEQ ID NO 96
<211> LENGTH: 25
<212> TYPE: DNA
<213> ORGANISM: Artificial Sequence
<220> FEATURE:
<223> OTHER INFORMATION: Env5(1) Primer;
      290 bp upstream of PERY17013 env stop codon

<400> SEQUENCE: 96
cttctatgta gatcactcag gagcc                                         25

<210> SEQ ID NO 97
<211> LENGTH: 24
<212> TYPE: DNA
<213> ORGANISM: Artificial Sequence
<220> FEATURE:
<223> OTHER INFORMATION: Env4c Primer;
      56 bp upstream of PERY17013 env stop codon

<400> SEQUENCE: 97
ctggactgca ctcactcgtt ctct                                          24

<210> SEQ ID NO 98
<211> LENGTH: 24
<212> TYPE: DNA
<213> ORGANISM: Artificial Sequence
<220> FEATURE:
<223> OTHER INFORMATION: 5env Primer; 93 bp upstream of PERY17013 env
      start site

<400> SEQUENCE: 98
cagtctatgt tagacgccac cgtg                                          24

<210> SEQ ID NO 99
<211> LENGTH: 20
<212> TYPE: DNA
<213> ORGANISM: Sus scrofa
<220> FEATURE:
<223> OTHER INFORMATION: LTR34C:  89 bp downstream of stop codon of env
      gene of PERY17013

<400> SEQUENCE: 99
ctttttatta acttcctggg                                               20

<210> SEQ ID NO 100
<211> LENGTH: 23
<212> TYPE: DNA

```
<213> ORGANISM: Sus scrofa
<220> FEATURE:
<223> OTHER INFORMATION: LTR100C:  141 bp downstream of the stop codon
      of the env gene of PERY17013

<400> SEQUENCE: 100
tgtgaccttc tacctattta ctg                                             23

<210> SEQ ID NO 101
<211> LENGTH: 351
<212> TYPE: DNA
<213> ORGANISM: Sus scrofa
<220> FEATURE:
<223> OTHER INFORMATION: G1 5'flanking sequence

<400> SEQUENCE: 101
gttcctctgc cagcgattgg ttgctgttct gtgcgagtca tttcttctgt agatgtgctt     60
tttttgttgt gtttgtggga gagggcgagc gtgtccccct actcctccgc catcttgtcc    120
tctctcttta tgcattttga atattaactc cttatcaggc atatgtctga aaatatattt    180
tcagtttgtc aatattttc tttgctgtgc aaaaacttt aactttaact agatcacatt     240
tgtttatttt gcttttattt cccttacctg aggtgacaga tccaagcaaa tattgctaag    300
atttttgtca aagagtgtac tgcctatgtt cttctaggaa ttttatggtt t             351

<210> SEQ ID NO 102
<211> LENGTH: 329
<212> TYPE: DNA
<213> ORGANISM: Sus scrofa
<220> FEATURE:
<223> OTHER INFORMATION: G2 5'flanking sequence

<400> SEQUENCE: 102
tcagatggaa tccatggcca caggcctatg ccacagcaat gccagatcct aacccactg      60 aatgaggaca gggatggaac ccacatcttc atggacacta gcagggttct aaagtcactg    120
aggcacagga agactccaag taacatgtat ttttaattgt gttacattta gttccataat    180
tacctttgat tcttacatat tggagttttg ctgatattaa ggaaacatat gcttcataag    240
tttctcatga gcatcaaccc tgtacatgat tgcttgtttt taagcacttt tatggtaaca    300
ttggcatttg tccatcatct tttttccttt                                    329

<210> SEQ ID NO 103
<211> LENGTH: 303
<212> TYPE: DNA
<213> ORGANISM: Sus scrofa
<220> FEATURE:
<223> OTHER INFORMATION: G3 5'flanking sequence

<400> SEQUENCE: 103
tgaaatcaca cgatcctccc gcgactgcca cctggagaca gaattacaga aagggggata     60
aagaatgcaa gcactgtctc gtcattcaaa ctctaacatg tggttaaata agcctcacag    120
actgcacatg gaaattgaaa tcaagccagg aaaaccccaa ttttcacct gcctgtcact    180 tcgcagacat tccaagcgcg gggtctgtct tccggggcct gggccctctg ccttccttcc    240
atcatcttag agcaggtgct ctcagactgc ccttggcttg catagctcgt gtcgtacttc    300
cag                                                                  303

<210> SEQ ID NO 104
<211> LENGTH: 310
<212> TYPE: DNA
```

```
<213> ORGANISM: Sus scrofa
<220> FEATURE:
<223> OTHER INFORMATION: G4 5'flanking sequence
<220> FEATURE:
<221> NAME/KEY: modified_base
<222> LOCATION: (29)
<223> OTHER INFORMATION: n = g, a, c or t
<220> FEATURE:
<221> NAME/KEY: modified_base
<222> LOCATION: (41)
<223> OTHER INFORMATION: n = g, a, c or t
<220> FEATURE:
<221> NAME/KEY: modified_base
<222> LOCATION: (48)
<223> OTHER INFORMATION: n = g, a, c or t

<400> SEQUENCE: 104
ccccaccccc acccatttac ctttaaggnt ttttttgtc ntttgtcntt tttttttttt      60
ttttttcttg ttgttgttgt tgctatttct tgggccgctc ccgcggcata tggagattcc    120
caggctaggg gttgaatcgg agctgtagcc accggcctac gccagagcca cagcaacgcg    180
ggatccgagc cgcgtctgca acctacacca cagctcacgg caacgctgga tcgtcaaccc    240
actgagcaag ggcagggacc gaacccgcaa cctcatggtt cctagtcgga ttcgttaacc    300
actgcgccac                                                          310

<210> SEQ ID NO 105
<211> LENGTH: 385
<212> TYPE: DNA
<213> ORGANISM: Sus scrofa
<220> FEATURE:
<223> OTHER INFORMATION: G7 5'flanking sequence

<400> SEQUENCE: 105
ctaaagttgg atgtatcttt ggtagtaatt tttatctctg aaattagaaa atataatatt     60
atttcttcct ctctctgttc attagattga agaatctctt taaagcacat tttaaaatat   120
tatctaaaaa tactgacata atatttctgt acagtattaa taaatgtttt ttcattgcca   180
catacacaaa aagcttattg caatgctacg gcattcattc aatcttttgc caaatgttta   240
tcaagcacct gctatgttct aatatgttct aggcaatgtg gtatatacac tatttagttc   300
tccaaatata attatagttc ttcatcacaa atagttagaa ataaataac ttaaaatggg    360 tccaacccca taatctttct tgtag                                        385

<210> SEQ ID NO 106
<211> LENGTH: 315
<212> TYPE: DNA
<213> ORGANISM: Sus scrofa
<220> FEATURE:
<223> OTHER INFORMATION: G8 5'flanking sequence

<400> SEQUENCE: 106
aaaataacaa ctgaagagct ggtggtgaca cggttggtac agggtgctgg ggcccagggc     60
ttctcctatt gcagggtcag ggagccatgc cctccagcag gccagcctgt ggggggttgag   120 cctgtctctt ctcactggaa gtgttgagtt tgtaatgaaa ggtagacttg ttatcatcta    180
cctttgatcc tggccacgag cagggcctgt ggcccttgg gggtggtttc ctaataactg    240
acctgcacga agcacagaat agtcaaggct gtgtatgtcc atggcccctta tactagatgg   300 tagacagggg cccac                                                   315

<210> SEQ ID NO 107
<211> LENGTH: 393
```

```
<212> TYPE: DNA
<213> ORGANISM: Sus scrofa
<220> FEATURE:
<223> OTHER INFORMATION: G10 5'flanking sequence
<220> FEATURE:
<221> NAME/KEY: modified_base
<222> LOCATION: (358)
<223> OTHER INFORMATION: n = g, a, c or t

<400> SEQUENCE: 107
gtttctttta tactgtttac attattattt ttgtggtgaa gagaaggaat attcagtgct      60
ttggatcagt gcattaaaca aagagaaagg ggtcttttcc tctttgttta gaacttggat     120
gttttgagca tgtgtcgtac acctggcaga agtctaagca acccttctcc atcctggcag     180
gtgtgtgata cccagtggat ggagctaagg aattttataa aacttttttac ccagagagag     240 ccatgtattg catgaagcag cagggtgccc tcaagaatca cgtgacctgg cagaggcagc     300
agtgtccatg gcagtggcca gtatccattg gatgagggc aggtcctgtt ggagcctnca     360
aggtacttgg tggtgaatga gtccacagta ggc                                  393

<210> SEQ ID NO 108
<211> LENGTH: 337
<212> TYPE: DNA
<213> ORGANISM: Sus scrofa
<220> FEATURE:
<223> OTHER INFORMATION: G13 5'flanking sequence

<400> SEQUENCE: 108
aataatttgg gaattgccct tttggcacag ccagttatga aactgactag tattcatgag      60
gacacaggtt tgatctccgg cctcacttag tgaattaagc atctgtggta taggtcacag     120
atgaggctcg gatcccactt tgctgtttct gtgctgtagg cttgcagttg cagctccaat     180
tccaccccta gcctgagaac ttacatatgc caccatgccc taaaggaaa aaaaatggac     240 ctataaactc aaaagcttat acacagcaaa ggaatccata caaaaatgaa aaacaaccca     300
cacaatgaga gaaagtactt gaaaatgatg caactga                              337

<210> SEQ ID NO 109
<211> LENGTH: 276
<212> TYPE: DNA
<213> ORGANISM: Sus scrofa
<220> FEATURE:
<223> OTHER INFORMATION: G14 5'flanking sequence

<400> SEQUENCE: 109
ggtggggggg gggggtgccc gggctgactg tgtacagtga caacaggggc tgagccccgg      60
gaaggaagcc atcccccagg cggtctctat ttgtccataa acacagtcca ccccacgccc     120
cagggcggag gaggggcaaa gaaaccagcc cagctggagc tgccttccca ctgctttcct     180 ggcaggggc actcccaggc acccaggcac accacctcct cctcataggc tccatctccc     240
tcccagcacc accccctgag ttgtttccac agcaag                               276

<210> SEQ ID NO 110
<211> LENGTH: 345
<212> TYPE: DNA
<213> ORGANISM: Sus scrofa
<220> FEATURE:
<223> OTHER INFORMATION: G15 5'flanking sequence

<400> SEQUENCE: 110
atggtgtagg ccggcagctg cagctctgat ttgaccccta gtctgggaac ttccatatgc      60
```

```
tgcagatatg gccctaaaaa gcaaaaaata aataaaata aaatcttttt ataaatgtgc      120
aacttataaa atgtctttgt ttaaactacc attactaagt ttgaatctat aaagaatgaa      180
acatttacaa atttagacct aaaatatttt ctctctactt tgtactgtct ctctagggag      240
ctggaagaga tgctaaaggc aacaacctat ttaatttatg ttctttggaa tatcctgtgg      300
ctaactgaac cttttcagtc ttttcatgac tcctaccatt ccttt                     345

<210> SEQ ID NO 111
<211> LENGTH: 420
<212> TYPE: DNA
<213> ORGANISM: Sus scrofa
<220> FEATURE:
<223> OTHER INFORMATION: G17 5'flanking sequence

<400> SEQUENCE: 111
gatgagctga ggcgttagtg aagacttagg gagaaatttt gggactattt aaagtgctaa       60
tcaaaattgc tagtgggtag ttccaggaaa agacatttta tgctaatgct ttttccttt       120 attttaatct aatccattgg ctttacattt tgaaaatgt accttgtagg ctagttaaat       180
atgaatttac tgttaagtca cattaaggaa gattataggt taggcctgta gggctcctaa      240
acagcctgca gctgctaaca cttcactagg taaggcacag gcaaagtgta caatggccct      300
ggtaggcttt tcctcaataa attaattaat ataggtttac attcttctca gagagaatcg      360
gcgttctctg acatgcactc attaatgtaa gttacgagac aaagtatttt aattatatat      420

<210> SEQ ID NO 112
<211> LENGTH: 421
<212> TYPE: DNA
<213> ORGANISM: Sus scrofa
<220> FEATURE:
<223> OTHER INFORMATION: G19 5'flanking sequence

<400> SEQUENCE: 112
ttcacatgct cagaaaggag aaggaggtat ttcttttttct atctctggga ctggtaaagt       60
gagataggtt gtattttgat caacatttaa aaaaaaattc atgataagat agtatttggg      120
tgacatgagg agaaaggtct aaaccttaga ttttgtagca gattttacac acattggtca      180
tgtcagaaag gtctccctct tgggtatttc cagagctgct cactttcctt aacataaaat      240
gtggcctcat tagcgcagat gggaagaatg ggtcagcttt tcacaaaact ctcagggct       300 gctgtgtgtc tgatatattg agtattatag gattttaatc tattcaaatg agaaacactg      360
tgtgctattt tattataaac actttaaaaa aatagaggta gaccaccacc taaaatcctt      420
c                                                                       421

<210> SEQ ID NO 113
<211> LENGTH: 374
<212> TYPE: DNA
<213> ORGANISM: Sus scrofa
<220> FEATURE:
<223> OTHER INFORMATION: G20 5'flanking sequence

<400> SEQUENCE: 113
cctgcacccc aaacacgaag gtgcctagca accaggaag atggcgcttc gaacgaaggg       60
agtgggaggc acaccagctt ccagaaggcc cgggtctctg gttcctgtcc ttcctgctca      120
gggatctccc tggagccctg cctttgggga cagcccaggg cggaaggaag gcctgagctg      180
gatgtgtcaa tggtccaacc tcgatgatca ggccgtgccc tggctctcct gggtgtcatt      240
tttcccatct ggaaatcgat ctgggtggtg gcaagcgagt cctccttagg tgtggttcaa      300
```

<210> SEQ ID NO 114
<211> LENGTH: 365
<212> TYPE: DNA
<213> ORGANISM: Sus scrofa
<220> FEATURE:
<223> OTHER INFORMATION: G22 5'flanking sequence

<400> SEQUENCE: 114

```
tcgatcttta actagctgag caggattaag gatcaaatcc atatcctcat ggatacaaga      60
cagattcatt ccaatgagcc acaatgggaa ctcccaggtt tctataccct aggaggctct     120
tggtgtcagg gaagttatag aggccccccca aacccacccc tccctgcagg aatgtgacta    180
tgcagcctgc agaccccacc ccaggctcag gcaggaaatt ctcaagccca ccaccatcag     240
tgtctactgc cagggtggct cctccatgga cctgctttcc cctaagtgga tgacacagat     300
gagcccagga aaatgtcatg ccagctcttt tgaggcctgc ttgggtggct ttaaaagttc     360
acatg                                                                 365
```

<210> SEQ ID NO 115
<211> LENGTH: 406
<212> TYPE: DNA
<213> ORGANISM: Sus scrofa
<220> FEATURE:
<223> OTHER INFORMATION: G24 5'flanking sequence

<400> SEQUENCE: 115

```
caagccacat ccgtaaccaa ccccacagct cacagcaact ccagatcctt aacccactga      60
gggaggccag agatcaaagc tgtatcctca tggatactag tcaggtttgt taccactgag     120
ccacaatgga aattcctgag gatgttttct cgatagcata aacacctgtc atagtgagat     180
gattctttaa cagaattaag accacaaaaa actatttgag tagatctagc agtacatgag     240
agtagctgcc tatctactta ttttcccttt tacaactctg cccttatttt ctcagtaagt     300
atgattccct gaatttcatt ttttttttgg agcaaaaata catttgctgg ttacattcaa     360
cagatataac taatatgtca aaattattat ttactcagca tgtttc                    406
```

<210> SEQ ID NO 116
<211> LENGTH: 396
<212> TYPE: DNA
<213> ORGANISM: Sus scrofa
<220> FEATURE:
<223> OTHER INFORMATION: G26 5'flanking sequence

<400> SEQUENCE: 116

```
tcaggaatta attttacaac aatggaatga tatattctaa aatgcttaaa atcacacatt      60
ttatttttatt ttatttttcc tttagggctg caccgaggcg tctgaaagtt cccagtctag    120
gagtcaaatc agagctacag ctgtcggcct acgccacagc cacagcaacc caggatcctt     180
aacctgctga gcagggccgg ggatcggacc tgcatcctca tggatcctag tcgggttggt     240
tacagctgag ccatgacagg aactccctca catggcattt tatggccaaa tgcctttgtt     300
tgtgtttggt agctctttct tcctaacgtt ggcctacatt ttgaatttct tacctgaatc     360
tttataactt ggttaataat gataaattag gggaag                               396
```

<210> SEQ ID NO 117

```
<211> LENGTH: 303
<212> TYPE: DNA
<213> ORGANISM: Sus scrofa
<220> FEATURE:
<223> OTHER INFORMATION: G27 5'flanking sequence

<400> SEQUENCE: 117
cacccgtatt tggtgggtta ccagcactag cgcctggttt tgacattatt tctccttgat      60
gcgcaggtac gatttcattc ttgaatatga gctgttccct ggctgcctcc tcttttgca     120 ttaactgtgg cttccagttc cctttctccc cgtgctccct taacaactgc ctggacgtgt    180
cggttgcttt catggctcag tgccccttta tccttttatt cgtttactac ctttgcagtt    240
gtttattttt ttaatcaaat ttactctcct tatccttggg catttgtaaa ttacattctg    300
gat                                                                  303

<210> SEQ ID NO 118
<211> LENGTH: 403
<212> TYPE: DNA
<213> ORGANISM: Sus scrofa
<220> FEATURE:
<223> OTHER INFORMATION: G28 5'flanking sequence

<400> SEQUENCE: 118
cccaacttct ttcctctctc tgaacacaca gaaaaataaa attcaaatag attttgtctt      60
gaataaatca ccagaggtta attttattgc attttactta caaataaaaa tagggtgggt    120
cctagctact ttttactata tttaactgga attctctacc agattttta aattatattt     180 ttaaactgtg tcatctaaaa ggttttgtgg gggaagtaag caaaaacaca aattgatgtc    240
catttcctct cattttccat gtgtttcctt tggttaaata aatacgctaa aaatataata    300
tgcttcatgt gttaaaagaa ctctctggaa ggcacacatt gtttgcactc aattacttca    360
ccagcagatt tatagcagta acggcggggt tgataaatcc tgc                      403

<210> SEQ ID NO 119
<211> LENGTH: 20
<212> TYPE: DNA
<213> ORGANISM: Artificial Sequence
<220> FEATURE:
<223> OTHER INFORMATION: G1-5' primer sequence;
      G1 locus

<400> SEQUENCE: 119
tactcctccg ccatcttgtc                                                 20

<210> SEQ ID NO 120
<211> LENGTH: 20
<212> TYPE: DNA
<213> ORGANISM: Artificial Sequence
<220> FEATURE:
<223> OTHER INFORMATION: G2-5' primer sequence;
      G2 locus

<400> SEQUENCE: 120
tcactgaggc acaggaagac                                                 20

<210> SEQ ID NO 121
<211> LENGTH: 20
<212> TYPE: DNA
<213> ORGANISM: Artificial Sequence
<220> FEATURE:
<223> OTHER INFORMATION: G3-5' primer sequence;
      G3 locus
```

```
<400> SEQUENCE: 121
catcatctta gagcaggtgc                                              20

<210> SEQ ID NO 122
<211> LENGTH: 20
<212> TYPE: DNA
<213> ORGANISM: Artificial Sequence
<220> FEATURE:
<223> OTHER INFORMATION: G4-5' primer sequence;
      G4 locus

<400> SEQUENCE: 122
tcgtcaaccc actgagcaag                                              20

<210> SEQ ID NO 123
<211> LENGTH: 24
<212> TYPE: DNA
<213> ORGANISM: Artificial Sequence
<220> FEATURE:
<223> OTHER INFORMATION: G7-5' primer sequence;
      G7 locus

<400> SEQUENCE: 123
gccaaatgtt tatcaagcac ctgc                                         24

<210> SEQ ID NO 124
<211> LENGTH: 21
<212> TYPE: DNA
<213> ORGANISM: Artificial Sequence
<220> FEATURE:
<223> OTHER INFORMATION: G8-5' primer sequence;
      G8 locus

<400> SEQUENCE: 124
gaagcacaga atagtcaagg c                                            21

<210> SEQ ID NO 125
<211> LENGTH: 22
<212> TYPE: DNA
<213> ORGANISM: Artificial Sequence
<220> FEATURE:
<223> OTHER INFORMATION: G10-5' primer sequence;
      G10 locus

<400> SEQUENCE: 125
aagcaaccct tctccatcct gg                                           22

<210> SEQ ID NO 126
<211> LENGTH: 19
<212> TYPE: DNA
<213> ORGANISM: Artificial Sequence
<220> FEATURE:
<223> OTHER INFORMATION: G13-5' primer sequence;
      G13 locus

<400> SEQUENCE: 126
ttctgtgctg taggcttgc                                               19

<210> SEQ ID NO 127
<211> LENGTH: 20
<212> TYPE: DNA
<213> ORGANISM: Artificial Sequence
<220> FEATURE:
<223> OTHER INFORMATION: G14-5' primer sequence;
      G14 locus

<400> SEQUENCE: 127
```
aggaggggca aagaaaccag                                          20

<210> SEQ ID NO 128
<211> LENGTH: 20
<212> TYPE: DNA
<213> ORGANISM: Artificial Sequence
<220> FEATURE:
<223> OTHER INFORMATION: G15-5' primer sequence;
      G15 locus

<400> SEQUENCE: 128
gctggaagag atgctaaagg                                          20

<210> SEQ ID NO 129
<211> LENGTH: 19
<212> TYPE: DNA
<213> ORGANISM: Artificial Sequence
<220> FEATURE:
<223> OTHER INFORMATION: G17-5' primer sequence;
      G17 locus

<400> SEQUENCE: 129
aggtaaggca caggcaaag                                           19

<210> SEQ ID NO 130
<211> LENGTH: 22
<212> TYPE: DNA
<213> ORGANISM: Artificial Sequence
<220> FEATURE:
<223> OTHER INFORMATION: G19-5' primer sequence;
      G19 locus

<400> SEQUENCE: 130
aaaactctca ggggctgctg tg                                       22

<210> SEQ ID NO 131
<211> LENGTH: 19
<212> TYPE: DNA
<213> ORGANISM: Artificial Sequence
<220> FEATURE:
<223> OTHER INFORMATION: G20-5' primer sequence;
      G20 locus

<400> SEQUENCE: 131
ttacggagca tcaccatcg                                           19

<210> SEQ ID NO 132
<211> LENGTH: 18
<212> TYPE: DNA
<213> ORGANISM: Artificial Sequence
<220> FEATURE:
<223> OTHER INFORMATION: G22-5' primer sequence;
      G22 locus

<400> SEQUENCE: 132
gatgagccca ggaaaatg                                            18

<210> SEQ ID NO 133
<211> LENGTH: 19
<212> TYPE: DNA
<213> ORGANISM: Artificial Sequence
<220> FEATURE:
<223> OTHER INFORMATION: G24-5' primer sequence;
      G24 locus

<400> SEQUENCE: 133

<210> SEQ ID NO 134
<211> LENGTH: 22
<212> TYPE: DNA
<213> ORGANISM: Artificial Sequence
<220> FEATURE:
<223> OTHER INFORMATION: G26-5' primer sequence;
    G26 locus

<400> SEQUENCE: 134
gcctttgttt gtgtttggta gc                                    22

<210> SEQ ID NO 135
<211> LENGTH: 20
<212> TYPE: DNA
<213> ORGANISM: Artificial Sequence
<220> FEATURE:
<223> OTHER INFORMATION: G27-5' primer sequence;
    G27 locus

<400> SEQUENCE: 135
ttccagttcc ctttctcccc                                       20

<210> SEQ ID NO 136
<211> LENGTH: 20
<212> TYPE: DNA
<213> ORGANISM: Artificial Sequence
<220> FEATURE:
<223> OTHER INFORMATION: G28-5' primer sequence;
    G28 locus

<400> SEQUENCE: 136
aaaagaactc tctggaaggc                                       20

<210> SEQ ID NO 137
<211> LENGTH: 8764
<212> TYPE: DNA
<213> ORGANISM: Sus scrofa
<220> FEATURE:
<223> OTHER INFORMATION: porcine endogenous retrovirus (PERV)
    G3 locus; G3 PERV genome

<400> SEQUENCE: 137
tgaaaggatg aaaatgcaac cttaaccctc ccagaaccca ggaagttaat aaaaagctct    60
aaatgccccc gaattccaga ccctgctggc tgccagtaaa taggtagaag gtcacacttc   120
ctattgttcc agggcctgct atcctggcct aagtaagata caggaaatg agttgactaa    180 tcgcttatct ggattctgta aaactgactg gcaccataga agaattgatt acacattgac   240
agccctagtg acctatctca actgcaatct gtcactctgc ccaggagccc acgcagatgc   300
ggacctccgg agctatttta aaatgattgg tccacggagc gcgggctctc gatattttaa   360
aatgattggt ccacggagcg cgggctctcg atattttaaa atgattggtt tgtgacgcac   420
aggctttgtt gtgaacccca taaagctgt cccgattccg cactcggggc cgcagtcctc    480 taccctgcg tggtgtacga ctgtgggccc cagcgcgctt ggaataaaaa tcctcttgct   540
gtttgcatca agaccgcttc tcgtgagtga tttgggggtgt cgcctcttcc gagcccggac   600 gaggggggatt gttcttttac tggccttttca tttggtgcat tggccgggaa accctgcgac   660 cacccctttac acccgagaac cgacttggag gtaaagggat ccccttttgga acttgtgtgt   720 gtgtcggccg gcgtctctgt tctgagtgtc tgttttcggt gatgcgcgct ttcggtttgc   780
agctgtcctc tcagaccgta aggactggag gactgtgatc agcagacgtg ctaggaggat   840

-continued

| | |
|---|---|
| cacaggctgc cacccctgggg gacgccccgg gaggtgggga gagccaggga cgcctggtgg | 900 |
| tctcctactg tcggtcagag gaccgagttc tgttgttgaa gcgaaagctt ccccctccgc | 960 |
| ggccgtccga ctcttttgcc tgcttgtgga agacgcggac gggtcgcgtg tgtctggatc | 1020 |
| tgttggtttc tgtttcgtgt gtctttgtct tgtgcgtcct tgtctacagt tttaatatgg | 1080 |
| gacagacagt gacgaccccc cttagtttga ctctcgacca ttggactgaa gttagatcca | 1140 |
| gggctcataa tttgtcagtt caggttaaga agggaccttg gcagactttc tgtgcctctg | 1200 |
| aatggccaac attcgatgtt ggatggccat cagaggggac cttttaattct gaaattatcc | 1260 |
| tggctgttaa ggcaatcatt tttcagactg gacccagctc tcatcctgat caggagccct | 1320 |
| atatccttac gtggcaagat ttggcagaag atcctccgcc atgggttaaa ccatggctaa | 1380 |
| ataaaccaag aaagccaggt ccccgaatcc tggctcttgg agagaaaaac aaacactcgg | 1440 |
| ccgaaaagt cgagccctct cctcgtatct accccgagat cgaggagccg ccgacttggc | 1500 |
| cggaacccca acctgttccc cccaccccctt atccagcaca gggtgctgtg aggggaccct | 1560 |
| ctgcccctcc tggagctccg gtggtggagg gacctgctgc cgggactcgg agccggagag | 1620 |
| gcgccacccc ggagcggaca gacgagatcg cgatattacc gctgcgcacc tatggccctc | 1680 |
| ccatgccggg gggccaattg cagccctccc agtattggcc ctttcttct gcagatctct | 1740 |
| ataattggaa aactaaccat cccctttct cggaggatcc ccaacgcctc acggggttgg | 1800 |
| tggagtccct tatgttctct caccagccta cttgggatga ttgtcaacag ctgctgcaga | 1860 |
| cactcttcac aaccgaggag cgagagagaa ttctgttaga ggctagaaaa aatgttcctg | 1920 |
| gggccgacgg gcgacccacg cagttgcaaa atgagattga catgggattt cccttgactc | 1980 |
| gccccggttg ggactacaac acggctgaag gtagggagag cttgaaaatc tatcgccagg | 2040 |
| ctctggtggc gggtctccgg ggcgcctcaa gacggcccac taatttggct aaggtaagag | 2100 |
| aggtgatgca gggaccgaac gaacctccct cggtatttct tgagaggctc atggaagcct | 2160 |
| tcaggcggtt cacccctttt gatcctacct cggaggccca gaaagcctca gtggccctgg | 2220 |
| ccttcattgg gcagtcggct ctggatatca gaaagaaact tcagagactg gaagggttac | 2280 |
| aggaggctga gttacgtgat ctagtgagag aggcagagaa ggtgtattac agaagggaga | 2340 |
| cagaagagga gaaggaacag agaaaagaaa aggagagaga agaaagggag gaaagacgtg | 2400 |
| atagacggca agagaagaat ttgactaaga tcttggccgc agtggttgaa gggaagagca | 2460 |
| gcagggagag agagagagat tttaggaaaa ttaggtcagg ccctagacag tcagggaacc | 2520 |
| tgggcaatag gaccccactc gacaaggacc agtgtgcgta ttgtaaagaa aaaggacact | 2580 |
| gggcaaggaa ctgccccaag aagggaaaca aaggaccgaa ggtcctagct ctagaagaag | 2640 |
| ataaagatta ggggagacgg ggttcggacc ccctccccga gcccagggta actttgaagg | 2700 |
| tggaggggca accagttgag ttcctggttg ataccggagc ggagcattca gtgctgctac | 2760 |
| aaccattagg aaaactaaaa gaaaaaaat cctgggtgat gggtgccaca gggcaacggc | 2820 |
| agtatccatg gactacccga agaaccgttg acttggcagt gggacgggta acccactcgt | 2880 |
| ttctggtcat ccctgagtgc ccagtacccc ttctaggtag agacttactg accaagatgg | 2940 |
| gagctcaaat ttcttttgaa caaggaagac cagaagtgtc tgtgaataac aaacccatca | 3000 |
| ctgtgttgac cctccaatta gatgatgaat atcgactata ttctccccaa gtaaagcctg | 3060 |
| atcaagatat acagtcctgg ttggagcagt tccccaagc ctgggcagaa accgcaggga | 3120 |
| tgggtttggc aaagcaagtt ccccccacagg ttattcaact gaaggccagt gctacaccag | 3180 |

```
tatcagtcag acagtacccc ttgagtagag aggctcgaga aggaatttgg ccgcatgttc    3240
aaagattaat ccaacagggc atcctagttc ctgtccaatc cccttggaat actcccctgc    3300
taccggttag gaagcctggg accaatgatt atcgaccagt acaggacttg agagaggtca    3360
ataaaagggt gcaggacata cacccaacgg tcccgaaccc ttataacctc ttgagcgccc    3420
tcccgcctga acggaactgg tacacagtat tggacttaaa agatgccttc ttctgcctga    3480
gattacaccc cactagccaa ccgcttttg ccttcgaatg gagagatcca ggtacgggaa     3540
gaaccgggca gctcacctgg acccgactgc cccaagggtt caagaactcc ccgaccatct    3600
ttgacgaagc cctacacagg gacctggcca acttcaggat ccaacaccct caggtgaccc    3660
tcctccagta cgtggatgac ctgcttctgg cgggagccac caaacaggac tgcttagaag    3720
gtacgaaggc actactgctg gaattgtctg acctaggcta cagagcctct gctaagaagg    3780
cccagatttg caggagagag gtaacatact tggggtacag tttgcggggc gggcagcgat    3840
ggctgacgga ggcacggaag aaaactgtag tccagatacc ggcccaacc acagccaaac     3900 aagtgagaga gttttgggg acagctggat tttgcagact gtggatcccg ggtttgcga     3960 ccttagcagc cccactctac ccgctaacca agaaaaagg ggaattctcc tgggctcctg     4020
agcaccagaa ggcatttgat gctatcaaaa aggccctgct gagcgcacct gctctggccc    4080
tccctgacgt aactaaaccc tttacccttt atgtggatga cgtaaggga gtagcccgag      4140 gagtttttaac ccaaacccta ggaccatgga ggagacctgt tgcctacctg tcaaagaagc   4200
ttgatcctgt agccagtggt tggcccgtat gcctgaaggc tatcgcagct gtggccatac    4260
tggtcaagga cgctgacaaa ttgactttgg gacagaatat aactgtaata gcccccccatg   4320 cattggagaa catcgttcgg cagccccag accgatggat gaccaacgcc cgcatgaccc     4380
actatcaaag cctgcttctc acagagaggg tcactttcgc tccaccagcc gctctcaacc    4440
ctgccactct tctgcctgaa gagactgatg aaccagtgac tcatgattgc catcaactat    4500
tgattgagga gactggggtc cgcaaggacc ttacagacat accgctgact ggagaagtgc    4560
taacctggtt cactgacgga agcagctatg tggtggaagg taagaggatg gctggggcgg    4620
cggtggtgga cgggacccac acgatctggg ccagcagcct gccggaagga acttcagcgc    4680
aaaaggctga gctcatggcc ctcacgcaag ctttgcggct ggccgaaggg aaatccataa    4740
acatttatac ggacagcagg tatgcctttg cgactgcaca cgtacacggg gccatctata    4800
aacaaggggg gttgcttacc tcagcaggga gggaaataaa gaacaaagag gaaattctaa    4860
gcctattaga agccttacat ttgccaaaaa ggctagctat tatacactgt cctggacatc    4920
agaaagccaa agatctcata tctagaggga accagatggc tgaccgggtt gccaagcagg    4980
cagcccaggc tgttaacctt ctgcctataa tagaaacgcc caaagcccca gaacccagac    5040
gacagtacac cctagaagac tggcaagaga taaaaaagat agaccagttc tctgagactc    5100
cggaggggac ctgctatacc tcatatggga aggaaatcct gccccacaaa gaagggttag    5160
aatatgtcca acagatacat cgtctcaccc acctaggaac taaacacctg cagcagttgg    5220
tcagaacatc cccttatcat gttctgaggc taccaggagt ggctgactcg gtggtcaaac    5280
attgtgtgcc ctgccagctg gttaatgcta atccttccag aatacctcca ggaaagagac    5340
taagggaaag ccacccaggc gctcactggg aagtggactt cactgaggta aagccggcta    5400
aatacggaaa caaatatcta ttggttttg tagacacctt ttcaggatgg gtagaggctt     5460
atccctacta agaaagagact tcaaccgtgg tggctaaaaa aatactggag gaaatttttc    5520
cgagatttgg aataccctaag gtaatcgggt cagacaatgg tccagctttt gttgcccagg    5580
```

```
taagtcaggg actggccaag atattgggga ttgattggaa actgcattgt gcatacagac    5640
cccaaagctc aggacaggta gagaggatga atagaaccat aaagagacc cttaccaaat    5700
tgaccacaga gactggcatt aatgattgga tagctctcct gcccttgtg cttttaggg    5760
ttaggaacac ccctggacag tttgggctga cccctatga attgctctac ggggacccc    5820
ccccgttggt agaaattgct tctgtacata gtgctgatgt gctgctttcc cagccttgt    5880
tctctaggct caaggcgctc gagtgggtga ggcaacgagc gtggaagcag ctccgggagg    5940
cctactcagg agaaggagac ttgcaagttc cacatcgctt ccaagtggga gattcagtct    6000
atgttagacg ccaccgtgca ggaaacctcg agactcggtg aagggccct tatctcgtac    6060
ttttgaccac accaacggct gtgaaagtcg aaggaatctc cacctggatc catgcatccc    6120
acgttaagct ggcgccacct cccgactcgg ggtggagagc cgaaaagact gagaatcccc    6180
ttaagcttcg cctccatcgc ctggttcctt actctaacaa taactcccca ggccagtagt    6240
aaacgcctta tagacagctc gaaccccat agacctttat cccttacctg gctgattatt    6300
gaccctgata cgggtgtcac tgtaaatagc actcgaggtg ttgctcctag aggcacctgg    6360
tggcctgaac tgcatttctg cctccgattg attaaccccg ctgttaaaag cacacctccc    6420
aacctagtcc gtagttatgg gttctattgc tgcccaggca cagagaaaga gaatactgt    6480
gggggttctg gggaatcctt ctgtaggaga tggagctgcg tcacctccaa cgatggagac    6540
tggaaatggc cgatctctct ccaggaccgg gtaaaattct cctttgtcaa ttccggcccg    6600
ggcaagtaca aagtgatgaa actatataaa gataagagct gctccccatc agacttagat    6660
tatctaaaga taagttttcac tgaaaaagga aaacaggaaa atattcaaaa gtggataaat    6720
ggtatgagct ggggaatagt ttttttataaa tatggcgggg gagcagggtc cactttaacc    6780
attcgcctta ggatagagac ggggacagaa ccccctgtgg cagtgggacc cgataaagta    6840
ctggctgaac aggggccccc ggccctggag ccaccgcata acttgccggt gccccaatta    6900
acctcgctgc ggcctgacat aacacagccg cctagcaacg gtaccactgg attgattcct    6960
accaacacgc tagaaactc cccaggtgtt cctgttaaga caggacagag actcttcagt    7020
ctcatccagg gagctttcca agccatcaac tccaccgacc ctgatgccac ttcttcttgt    7080
tggctttgtc tatcctcagg gcctccttat tatgagggga tggctaaaga aggaaaattc    7140
aatgtgacca aagagcatag aaatcaatgt acatgggggt cccgaaataa gcttaccctc    7200
actgaagttt ccgggaaggg gacatgcata ggaaaagctc ccccatccca ccaacacctt    7260
tgctatagta ctgtggttta tgagcaggcc tcagaaaatc agtatttagt acctggttat    7320
aacaggtggt gggcatgcaa tactgggtta accccctgtg tttccacctc agtcttcaac    7380
caatccaaag atttctgtgt catggtccaa atcgtccccc gagtgtacta ccatcctgag    7440
gaagtggtcc ttgatgaata tgactatcgg tataaccgac aaaaagaga acccgtatcc    7500
cttaccctag ctgtaatgct cggattaggg acggccgttg gcgtaggaac agggacagct    7560
gccctgatca caggaccaca gcagctagag aaaggacttg gtgagctaca tgcggccatg    7620
acagaagatc tccgagcctt agaggagtct gttagcaacc tagaagagtc cctgacttct    7680
ttgtctgaag tggttctaca gaaccggagg ggattagatc tgctgtttct aagagaaggt    7740
gggttatgtg cagccttaaa agaagaatgt tgcttctatg tagatcactc aggagccatc    7800
agagactcca tgagcaagct tagagaaagg ttagagaggc gtcgaaggga aagagaggct    7860
gaccagggt ggtttgaagg atggttcaac aggtctcctt ggatgaccac cctgcttct    7920
```

-continued

```
gctctgacgg gacccctagt agtcctgctc ctgttactta cagttgggcc ttgcttaatt      7980
aataggtttg ttgcctttgt tagagaacga gtgagtgcag tccagatcat ggtacttagg      8040
caacagtacc aaggccttct gagccaagga gaaactgacc tctagccttc ccagttctaa      8100
gattagaact attaacaaga caagaagtgg ggaatgaaag gatgaaaatg caacctaacc      8160
ctcccagaac ccaggaagtt aataaaaagc tctaaatgcc cccgaattcc agaccctgct      8220
ggctgccagt aaataggtag aaggtcacac ttcctattgt tccagggcct gctatcctgg      8280
cctaagtaag ataacaggaa atgagttgac taatcgctta tctggattct gtaaaactga      8340
ctggcaccat agaagaattg attacacatt gaaagcccta gtgacgtatc tcaactgcaa      8400
tctgtcactc tgcccaggag cccgtgcaga tgcggacctc cggagctatt ttaaaatgat      8460
tggtccacgg agcgcgggct ctcgatattt taaaatgatt ggtccacgga gcgcgggctc      8520
tcgatatttt aaaatgattg gtttgtgacg cacaggcttt gttgtgaacc ccataaaagc      8580
tgtcccgatt ccgcactcgg ggccgcagtc ctctaccccct gcgtggtgta cgactgtggg      8640
ccccagcgcg cttggaataa aaatcctctt gctggttgca tcaagaaccg cttctcgtga      8700
gtgatttggg gtgtcgcctc ttccgagccc ggacgagggg gattgttctt ttactggcct      8760
ttca                                                                   8764
```

<210> SEQ ID NO 138
<211> LENGTH: 8919
<212> TYPE: DNA
<213> ORGANISM: Sus scrofa
<220> FEATURE:
<223> OTHER INFORMATION: porcine endogenous retrovirus (PERV)
      G319 locus; G19 PERV genome

<400> SEQUENCE: 138

```
tgaaaggatg aaaatgcaac ctgactctcc cagaacccag gaagttaata agaagctcta      60
aatgccctcg aattccagac cctgttccct ataggtaaaa gatcatactt tttgctgttt      120
tagggcttgc tttctgctct gtacaaaact tgtggaagg ggaaaaacag gcccctgagt       180
atgtgcctct atgcttgaaa cttcttgaaa ctgctcctaa ctgcttgttt ggcttctgta      240
aacctgcttg cataagataa aaagaggaga agtcaattgc ctaacggacc ccagtaagat      300
cgggcgtgcc acaaaatgtt gaaaatcctg ataaatatat cttggtgaca atatgtctcc      360
cccaccccaga gacaggcaca acatgtaac tccagaacaa cttaaaatta ttggtccac      420
aaagcgcggg ctctcgaagt tttgaattga ctggtttgcg atatttttaaa aatgattagt      480
ttgtaaaagc gcgggctttg ttgtgaaccc cataaaagct gtcccgactc cacactcggg      540
gccgcagtcc tctaccccct cgtggcgtac gactgtgggc cccagcgcgc tcggaataaa      600
aatcctcttg ctgtttgcat caagaccgct ctcgtgagt gatttggggt gtcgcctctt      660
ccgagtcagg atgagaggga tttaactcg actggccttt cagtttggtg cgttggccgg       720
gaaacccgcg actacccctc acaccgaga accgacttgg aggtaaaggg atcccctttg       780
gaacgtgtga gtgtgtgtgt cggctggcgt ctctgttctg agtgtctgtt ttcggtgatg      840
cgcgctttcg gtttgcagct gtcctctcag accgtaagga ctgggggact gtgatcagca      900
gacgtgctag gaggatcaca ggctgccacc ctggggacg ccccgggagg tggggagagc       960
cagggacgcc tggtggtctc cttctgtcgg tcagaggacc gagttctgtt gttgaagcga      1020
aagcttcccc ctccgcggcc gtccgactct tttgcctgct tgtggaagac gcggacgggt      1080
cgcgtgtgtc tggatctgtt ggtttctgtt ttgtgtgtct ttgtcttgtg cgtccttgtc      1140
```

-continued

```
tacagtttta atatgggaca gacggtgacg acccctctta gtttgactct cgaccattgg    1200
actgaagtta aatccagggc tcataatttg tcagttcagg ttaagaaggg accttggcag    1260
actttctgtg tctctgaatg ccgacatttt gatgttggat ggccatcaga ggggaccttt    1320
aattctgaga ttatcctggc tgttaaagca attattttc agactggacc cggctctcat    1380
cccgatcagg agcctatat ccttacgtgg caagatttgg cagaggatcc tccgccatgg    1440
gttaaacctt ggctgaataa gccaagaaag ccaggtcccc gaattctggc tcttggagag    1500
aaaaacaaac actcggctga aaagtcaag ccctctcctc atatctaccc cgagattgag    1560
gagccgccgg cttggccgga accccaatct gttcccccac cccttatcc ggcacagggt    1620
gctgcgaggg gaccctctgc ccctcctgga gctccggcgg tggagggacc tgctgcaggg    1680
actcggagcc ggaggggcgc caccccggag cggacagacg agatcgcgac attaccgctg    1740
cgcacgtacg gccctcccat accgggggc caattgcagc cctccagta ttggcccttt    1800
tcttctgcag atctctataa ttggaaaact aaccatcccc ctttctcgga ggatccccaa    1860
cgcctcacgg ggttggtgga gtcccttatg ttctctcacc agcctacttg ggatgattgt    1920
caacagctgc tgcagacact cttcacaacc gaggagcgag agagaattct gttagaggct    1980
agaaaaaatg ttcctggggc cgacgggcga cccacgcagt tgcaaaatga gattgacatg    2040
ggatttccct tgactcgccc cggttgggac tacaacacgg ctgaaggtag ggagagcttg    2100
aaaatctatc gccaggctct ggtggcgggt ctccggggcg cctcaagacg gcccactaac    2160
ttggctaagg taagagaggt gatgcaggga ccgaatgaac ctccctcagt ttttcttgag    2220
aggctcatgg aagccttcag gcggttcacc ccttttgatc ctacctcgga ggctcagaaa    2280
gcctcagtgg ctctggcctt cataggacag tcagccctgg atatcagaaa gaagcttcag    2340
agactggaag ggttacagga ggctgagtta cgtgatctag tgaaggaggc agagaaagtg    2400
tattacaaaa gggagacaga agaagaaagg gaacaaagaa aagagagaga aagagaggaa    2460
agggaggaaa gacgtaataa acggcaagag aagaatttga ctaagatctt ggctgcagtg    2520
gttgaaggga aaagcaatag ggaaagagag agagatttta ggaaaattag gtcaggccct    2580
agacagtcag ggaacctggg caataggacc ccactcgaca aggaccaatg tgcatattgt    2640
aaagaaaaag gacactgggc aagggactgc cccaagaagg gaaacaaagg actgaaggtc    2700
ttagctctgg aagaagataa agactaggga agacgggtt cggaccccct ccccgagccc    2760
agggtaactt taaggtggga ggggcaacca gttgagtttc tggttgatac cggagcgaaa    2820
cattcagtgc tactacagcc attaggaaaa ctaaaagata aaaaatcctt gggtgatggg    2880
tgccacaggg aaacaacaat atccatggac taccgaaga acagttgact tgggagtggg    2940
acgggtaacc cactcgtttc tggtcatacc tgagtgccca gcacccctct taggtagaga    3000
cttactgacc aagatgggag cacaaatttc ttttgaacaa gggaaaccag aagtgtctgc    3060
aaataacaaa cctatcactg tgttgaccct ccaattagat gacgaatatc gactatattc    3120
tcccctagta aagcctgatc aaaatataca attctggttg gaacagtttc cccaagcctg    3180
ggcagaaacc gcaggatgg gtttggcaaa gcaagttccc ccacaggtta ttcaactgaa    3240
ggccagtgct gcaccagtgt cagtcagaca gtaccccttg agtaaagaag ctcgagaagg    3300
aattcggccg catgttcaaa gattaatcca acagggcatc ctagttcctg tccaatctcc    3360
ctggaatact ccctgctac cggttagaaa gcctgggact aatgactatc gaccagtaca    3420
ggacttgaga gaggtcaata aacgggtgca ggatatacac ccaacagtcc cgaaccctta    3480
taacctcttg tgtgctctcc cacccccaacg gagctggtat acagtattgg acttaaagga    3540
```

```
tgccttcttc tgcctgagac tacatcccac tagccaacca cttttgcct tcgaatggag    3600
agatccaggt gcgggaagaa ccgggcagct cacttggact cgactgcccc aagggttcaa    3660
aaactccccg accatctttg acgaagccct acacagagac ctggccaact tcaggatcca    3720
acacccccag gtgaccctcc tccagtacgt ggatgacctg cttctggcgg agccaccaa    3780
acaggactgc ttagaaggta cgaaggcact actgctggaa ttgtctgacc taggctacag    3840
agcctccgct aagaaggccc agatttgcag gagagaggta acatacttgg ggtacagttt    3900
gcggggcggg cagcgatggc tgacggaggc acggaagaga actgtagtcc agataccggc    3960
ccccaccaca gccaaacaag tgagagagtt tttggggaca gctggatttt gcagactgtg    4020
gatcccgggg tttgcgacct tagcagcccc actctaccca ctaaccaaag aaaaagggga    4080
attctcctgg gctcctgagc accagaaggc atttgatgct atcaaaaagg ccctgctgag    4140
cgcacctgct ctggccctcc ctgacgtgac taaacccttt acctttatg tggatgagcg    4200
taagggagta gcccggggag ttttaaccca aactctagga ccatggagga gacctgttgc    4260
ctacctgtca aagaagctcg atcctgtagc cagtggttgg cccgtatgcc tgaaggctat    4320
cgcagctgtg gccatactgg tcaaggacgc tgacaaattg actttgggac agaatataac    4380
tgtaatagcc ccccatgcat ggagaacat cgttcggcag ccccagacc gatggatgac    4440
caacgcccgc atgacccact atcaaagcct gcttctcaca gagagggtca cgttcgctcc    4500
accagccgct ctcaaccctg ccactcttct gcctgaagag actgatgaac cagtgactca    4560
tgattgccat caactattga ttgaggagac tggggtccgc aaggacctta cagacatacc    4620
gctgactgga gaagtgttaa cctggttcac tgacggaagc agctatgtgg tggaaggtaa    4680
gaggatggct ggggcggcgg tggtggacgg gacccgcacg atctgggcca gcagcctgcc    4740
ggaaggaact tcagcacaaa aggctgagct catggccctc acgcaagctt gcggctggc    4800
cgaagggaaa tccataaaca tttatacaga cagcaggtat gcctttgcga ctgcacacgt    4860
acacggggcc atctataagc aaaggggggtt gcttacctca gcagggaggg aaataaagaa    4920
caaagaggaa attctaagcc tattagaagc cttacatttg ccaaaaaggc tagctattat    4980
acactgtcct ggacatcaga aagccaaaga tcccatatcc agagggaacc agatggctga    5040
ccgggttgcc aagcaggcag cccagggtgt taaccttctg cctatgatag aaacacccaa    5100
agccccagaa cccggacgac agtacaccct agaagactgg caagaaataa aaagataga    5160
ccagttctct gaaactccgg aggggacctg ctatacctca gatgggaagg aaatcctgcc    5220
ccacaaagaa gggttagaat atgtccaaca gatacatcgt ctaaccccacc taggaactaa    5280
acacctgcag cagttggtca gaacatcccc ttatcatgtt ctgaggctac caggagtggc    5340
tgactcggtg gtcaaacatt gtgtgccctg ccagctggtt aatgctaatc cttccagaat    5400
acctccagga aagagactaa ggggaagcca cccaggcgct cactgggaag tggacttcac    5460
tgaggtaaag ccggctaaat acggaaacaa atatctattg gtttttgtag acaccttttc    5520
aggatgggta gaggcttatc ctactaagaa agagacttca accgtggtgg ctaagaaaat    5580
actggaggaa attttccaa gatttggaat acctaaggta atagggtcag acaatggtcc    5640
agctttcgtt gcccaggtaa gtcagggact ggccaagata ttgggggattg attggaaact    5700
gcattgtgca tacagacccc aaagctcagg acaggtagag aggatgaata gaaccattaa    5760
agagaccctt accaaaattga ccacagagac tggcattaat gattggatag ctctcctgcc    5820
cttttgtgctt tttagggtga ggaacacccc tggacagttt gggctgaccc cctatgaatt    5880
```

```
gctctacggg ggaccccccc cgttggcaga aattgccttt gcacatagtg ctgatgtgct    5940
gctttcccag cctttgttct ctaggctcaa ggcgctcgag tgggtgaggc agcgagcgtg    6000
gaagcagctc cgggaggcct actcaggagg agacttgcaa gttccacatc gcttccaagt    6060
tggagattca gtctatgtta gacgccaccg tgcaggaaac ctcgagactc ggtggaaggg    6120
accttatctc gtacttttga ccacaccaac ggctgtgaaa gtcgaaggaa tccccacctg    6180
gatccatgca tcccacgtta agccggcgcc acctcccgat tcgggtgga aagccgaaaa     6240 gactgaaaat ccccttaagc ttcgcctcca tcgcgtggtt ccttactctg tcaataactc    6300
ctcaagttaa tggtaaacgc cttgtggaca gcccgaactc ccataaaccc ttatctctca    6360
cctggttact tactgactcc ggtacaggta ttaatattaa cagcactcaa ggggaggctc    6420
ccttggggac ctggtggcct gagttatatg tctgccttcg atcagtaatc cctggtctca    6480
atgaccaggc cacacccccc gatgtactcc gtgcttacgg gttttacgtt tgcccaggac    6540
ccccaaataa tgaagaatat tgtggaaatc ctcaggattt cttttgcaag caatggagct    6600
gcgtaacttc taatgatggg aattggaaat ggccagtctc tcagcaagac agagtaagtt    6660
actcttttgt taacaatcct accagttata atcaatttaa ttatggccat gggagatgga    6720
aagattggca acagcgggta caaaaagatg tacgaaataa gcaaataagc tgtcattcgt    6780
tagacctaga ttacttaaaa ataagtttca ctgaaaaagg aaaacaagaa atattcaaa     6840 agtgggtaaa tggtatgtct tggggaatag tgtactatgg aggctctggg agaaagaaag    6900
gatctgttct gactattcgc ctcagaatag aaactcagat ggaacctccg gttgctatag    6960
gaccaaataa gggtttggcc gaacaaggac ctccaatcca agaacagagg ccatctccta    7020 accctctga ttacaataca acctctggat cagtccccac tgagcctaac atcactatta     7080
aaacaggggc gaaactttt agcctcatcc agggagcttt tcaagctctt aactccacga     7140
ctccagaggc tacctcttct tgttggcttt gcttagcttc gggcccacct tactatgagg    7200
gaatggctag aggagggaaa ttcaatgtga caaaggaaca tagagaccaa tgtacatggg    7260
gatcccaaaa taagcttacc cttactgagg tttctggaaa aggcacctgc atagggatgg    7320
ttcccccatc ccaccaacac ctttgtaacc acactgaagc ctttaatcga acctctgaga    7380
gtcaatatct ggtacctggt tatgacaggt ggtgggcatg taatactgga ttaaccccctt   7440 gtgtttccac cttggttttc aaccaaacta agactttg cgttatggtc caaattgtcc      7500
cccgggtgta ctactatccc gaaaaagcag tccttgatga atatgactat agatataatc    7560
ggccaaaaag agagcccata tccctgacac tagctgtaat gctcggattg ggaatggctg    7620
caggcgtggg aacaggaacg gctgccctaa tcacaggacc gcaacagctg gagaaaggac    7680
ttagtaacct acatcgaatt gtaacggaag atctccaagc cctagaaaaa tctgtcagta    7740
acctggagga atccctaacc tccttatctg aagtggttct acagaacaga agggggttag    7800
atctgttatt tctaaaagaa ggagggttat gtgtagcctt aaaagaggaa tgctgcttt     7860 atgtggatca ttcaggagct atcagggact ccatgagcaa gctcagagaa aggttagaaa    7920
aacgtcacaa agaaaagag gctggccaag atggtttga gggatggttc aacaagtccc      7980
catgggtgac caccctgctt tctgctctaa caggacccct agtaatactg ctcctgttgc    8040
ttacagttgg gccttgctta attaatcggt tgttgcctt tgttagagaa caagtgagtg      8100
cagttcggat catggtactt agacagcagt accaaggcct tccaagctaa ggagaaactg    8160
acctttagcc ttcctagttc taagattaga actattaaca agagaagaag tggggaatga    8220
aaggatgaaa atgcaacctg actctcccag aacccaggaa gttaataaga agctctaaat    8280
```

```
gccctcgaat tccagaccct gttccctata ggtaaaagat catactttt  gctgttttag    8340 ggcttgcttt ctgctctgta caaaactttg tggaagggga aaaacaggcc cctgagtatg    8400
tgcctctatg cttgaaactt cttgaaactg ctcctaactg cttgtttggc ttctgtaaac    8460
ctgcttgcat aagataaaaa gaggagaagt caattgccta acggacccca gtaagatcgg    8520
gcgtgccaca aaatgttgaa aatcctgata aatatatctt ggtgacaata tgtctccccc    8580
acccagagac aggcacaaac atgtaactcc agaacaactt aaaattaatt ggtccacaaa    8640
gcgcgggctc tcgaagtttt gaattgactg gtttgcgata ttttaaaaat gattagtttg    8700
taaaagcgcg ggctttgttg tgaacccat  aaaagctgtc ccgactccac actcggggcc    8760
gcagtcctct accctgcgt  ggcgtacgac tgtgggcccc agcgcgctcg gaataaaaat    8820
cctcttgctg tttgcatcaa gaccgcttct cgtgagtgat ttggggtgtc gcctcttccg    8880
agtcaggatg agagggattt taactcgact ggcctttca                          8919
```

<210> SEQ ID NO 139
<211> LENGTH: 8916
<212> TYPE: DNA
<213> ORGANISM: Sus scrofa
<220> FEATURE:
<223> OTHER INFORMATION: porcine endogenous retrovirus (PERV)
      G28 locus; G28 PERV genome

<400> SEQUENCE: 139

```
tgaaaggatg aaaatgcaac ctgactctcc cagaacccag gaagttaata agaagctcta     60
aatgccctcg aattccagac cctgttccct ataggtaaaa gatcatactt tttgctgttt    120
tagggcttgc tttctgctct gtacaaaact ttgtggaagg ggaaaaacag gcccctgagt    180
atgtgcctct atgcttgaaa cttcttgaaa ctgctcctaa ctgcttgttt ggcttctgta    240
aacctgcttg cataagataa aaagaggaga agtcaatcgc ctaaccgacc ccagtaagat    300
cgggcgtgcc acaaaatgtt gaaaatcctg ataaatatat cttggtgaca atatgtctcc    360
cccacccaga gacaggcaca acatgtaac  tccagaacaa cttaaaatta attggtccac    420
aaagcgcggg ctctcgaagt tttgaattga ctggtttgcg atattttaaa atgattagtt    480
tgtaaaagcg cgggctttgt tatgaacccc ataaaagctg tcccgactcc acactcgggg    540
ccgcagtcct ctaccctgc  gtggcgtacg actgtgggcc ccagcgcgct cggaataaaa    600
atcctcttgc tgtttgcatc aagaccgctt ctcgtgagtg atttggggtg tcgcctcttc    660
cgagtcagga cgagagggat tttaactcga ctggcctttc agtttggtgc gttggccggg    720
aaacccgcga ctaccctca  cacctgagaa ccgactggga ggtaaaggga tcccctttgg    780
aacgtgtgag tgtgtatgtc ggctggcgtc tctgttctga gtgtctgttt tcggtgatgc    840
gcgctttcgg tttgcagctg tcctctcaga ccgtaaggac tgggggactg tgatcagcag    900
acgtgctagg aggatcacag gctgccaccc tgggggacgc cccgggaggt ggggagagcc    960
agggacgcct ggtggtctcc ttctgtcggt cagaggaccg agttctgttg ttgaagcgaa   1020
agcttccccc tccgcggccg tccgactctt ttgcctgctt gtggaagacg cggacgggtc   1080
gcgtgtgtct ggatctgttg gtttctgttt tgtgtgtctt tgtcttgtgc gtccttgtct   1140
acagttttaa tatgggacag acggtgacga ccctcttag  tttgactctc gaccattgga   1200
ctgaagttaa atccagggct cataatttgt cagttcaggt taagaaggga ccttggcaga   1260 cttctgtgt  ctctgaatgg ccgacattcg atgttggatg ccatcagag  gggacccttta  1320 attctgagat tatcctggct gttaaagcaa ttattttca  gactggaccc ggctctcatc   1380
```

```
ccgatcagga gccctatatc cttacgtggc aagatttggc agaggatcct ccgccatggg    1440
ttaaaccttg gctgaataag ccaagaaagc caggtccccg aattctggct cttggagaga    1500
aaaacaaaca ctcggctgaa aaagtcaagc cctctcctca tatctacccc gagattgagg    1560
agccgccggc ttggccggaa ccccaatctg ttcccccacc cccttatccg gcacagggtg    1620
ctgcgagggg accctctgcc cctcctggag ctccggcggt ggaggacct gctgcaggga     1680 ctcggagccg aggggcgcc accccggagc ggacagacga gatcgcgaca ttaccgctgc     1740
gcacgtacgg ccctcccata ccgggggggcc aattgcagcc cctccagtat tggcccttt    1800 cttctgcaga tctctataat tggaaaacta accatccccc tttctcggag gatccccaac    1860
gcctcacggg gttgatggag tcccttatgt tctctcacca gcctacttgg gatgattgtc    1920
aacagctgct gcagacactc ttcacaaccg aggagcgaga gagaattctg ttagaggcta    1980
gaaaaaatgt tcctggggcc gacggcgac ccacgcagtt gcaaaatgag attgacatgg     2040 gatttcccctt gactcgcccc ggttgggact acaacacggc tgaaggtagg gagagcttga   2100
aaatctatcg ccaggctctg gtggcgggtc tccggggcgc ctcaagacgg cccactaact   2160
tggctaaggt aagagaggtg atgcagggac cgaatgaacc tccctcagtt tttcttgaga    2220
ggctcatgga agccttcagg cggttcaccc cttttgatcc tacctcggag gctcagaaag    2280
cctcagtggc cctggccttc ataggacagt cagccctgga tatcagaaag aagcttcaga    2340
gactggaagg gttacaggag gctgagttac atgatctagt gaaggaggca gagaaagtgt    2400
attacaaaag ggagacagaa gaagaaaggg aacaaagaaa agagagagaa agagaggaaa    2460
gggaggaaag acgtaataaa cggcaagaga gaatttgac taagatcttg gctgcagtgg     2520
ttgaagggaa aagcaatagg gaaagagaga gagattttag gaaaattagg tcaggcccta    2580
gacagtcagg gaacctgggc aataggaccc cactcgacaa ggaccaatgt gcatattgta    2640
aagaaaaagg acactgggca agggactgcc ccaagaaggg aaacaaagga ctgaaggtct    2700
tagctctgga agaagataaa gactagggaa gacggggttc ggacccccctc cccgagccca   2760 gggtaacttt aaaggtggag gggcaaccag ttgagtttct ggttgatacc ggagcgaaac    2820
attcagtgct actacagcca ttaggaaaac taaaagataa aaaatcctgg gtgatgggtg    2880
ccacagggca acaacaatat ccatggacta cccgaagaac agttgacttg ggagtgggac    2940
gggtaaccca ctcgtttctg gtcatacctg agtgcccagc acccctctta ggtagagact    3000
tactgaccaa gatgggagca caaatttctt ttgaacaagg gaaaccagaa gtgtctgcaa    3060
ataacaaacc tatcactgtg ttgaccctcc aattagatga cgaatatcga ctatattctc    3120
ccctagtaaa gcctgatcaa aatatacaat tctggttgga acagtttccc caagcctggg    3180
cagaaaccgc agggatgggt ttggcaaagc aagttccccc acaggttatt caactgaagg    3240
ccagtgctgc accagtgtca gtcagacagt accccttgag taaagaagct cgagaaggaa    3300
ttcggccgca tgttcaaaga ttaatccaac agggcatcct agttcctgtc caatctccct    3360
ggaatactcc cctgctaccg gttagaaagc ctgggactaa tgactatcga ccagtacagg    3420
acttgagaga ggtcaataaa cgggtgcagg atatacaccc aacagtcccg aacccttata    3480
acctcttgtg tgctctccca ccccaacgga gctggtatac agtattggac ttaaaggatg    3540
ccttcttctg cctgagacta catcccacta gccaaccact ttttgccttc gaatggagag    3600
atccaggtgc gggaagaacc gggcagctca cttggactcg actgcccaa gggttcaaaa     3660 actccccgac catctttgac gaagccctac acagagacct ggccaacttc aggatccaac    3720
```

```
acccccaggt gaccctcctc cagtacgtgg atgacctgct tctggcggga gccaccaaac    3780
aggactgctt agaaggtacg aaggcactac tgctggaatt gtctgaccta ggctacagag    3840
cctccgctaa gaaggcccag atttgcagga gagaggtaac atacttgggg tacagtttgc    3900
ggggcgggca gcgatggctg acggaggcac ggaagagaac tgtagtccag ataccggccc    3960
caaccacagc caaacaagtg agagagtttt tggggacagc tggattttgc agactgtgga    4020
tcccggggtt tgcgacctta gcagcccac tctacccact aaccaaagaa aaagggggaat    4080 tctcctgggc tcctgagcac cagaaggcat ttgatgctat caaaaaggcc ctgctgagcg    4140
cacctgctct ggccctccct gacgtgacta aacccttta cctttatgtg gatgagcgta    4200
agggagtagc ccggggagtt ttaacccaaa ccctaggacc atggaggaga cctgttgcct    4260
acctgtcaaa gaagctcgat cctgtagcca gtggttggcc cgtatgcctg aaggctatcg    4320
cagctgtggc catactggtc aaggacgctg acaaattgac tttgggacag aatataactg    4380
taatagcccc ccatgcgttg gagaacatcg ttcggcagcc cccagaccga tggatgacca    4440
acgcccgcat gacccactat caaagcctgc ttctcacaga gagggtcacg ttcgctccac    4500
cagccgctct caaccctgcc actcttctgc ctgaagagac tgatgaacca gtgactcatg    4560
attgccatca actattgatt gaggagactg gggtccgcaa ggaccttaca gacataccgc    4620
tgactggaga agtgttaacc tggttcactg acggaagcag ctatgtggtg aaggtaagaa    4680
ggatggctgg ggcggcggtg gtggacggga cccgcacgat ctgggccagc agcctgccgg    4740
aaggaacttc agcacaaaag gctgagctca tggcccctcac gcaagctttg cggctggccg    4800
aagggaaatc cataaacatt tatacagaca gcaggtatgc ctttgcgact gcacacgtac    4860
acggggccat ctataagcaa aggggggttgc ttacctcagc agggagggaa ataaagaaca    4920
aagaggaaat tctaagccta ttagaagcct tacatttgcc aaaaaggcta gctattatac    4980
actgtcctgg acatcagaaa gccaaagatc ccatatccag agggaaccag atggctgacc    5040
gggttgccaa gcaggcagcc cagggtgtta accttctgcc tatgatagaa acacccaaag    5100
ccccagaacc cggacgacag tacaccctag aagactggca agaaatataaaa aagatagacc    5160 agttctctga aactccggag gggacctgct atacctcaga tgggaaggaa atcctgcccc    5220
acaaagaagg gttagaatat gtccaacaga tacatcgtct aacccaccta ggaactaaac    5280
acctgcagca gttggtcaga acatcccctt atcatgttct gaggctacca ggagtggctg    5340
actcggtggt caaacattgt gtgccctgcc agctggttaa tgctaatcct tccagaatac    5400
ctccaggaaa gagactaagg gggagccacc caggcgctca ctgggaagtg gacttcactg    5460
aggtaaagcc ggctaaatac ggaaacaaat acctattggt ttttgtagac accttttcag    5520
gatgggtaga ggcttatcct actaagaaag gacttcaac cgtggtggct aagaaaaatac    5580 tggaggaaat ttttccaaga tttggaatac ctaaggtaat agggtcagac aatggtccag    5640 cttttcgttgc ccaggtaagt cagggactgg ccaagatatt ggggattgat tggaaactgc    5700
attgtgcata cagaccccaa agctcaggac aggtagagag gatgaataga accattaaag    5760
agacccttac caaattgacc acagagactg gcattaatga ttggatagct ctcctgcccc    5820
ttgtgctttt tagggtgagg aacacccctg acagtttgg gctgacccc tatgaattgc    5880 tctacagggg accccccccg ttggcagaaa ttgcctttgc acatagtgct gatgtgctgc    5940
tttcccagcc tttgttctct aggctcaagg cgctcgagtg ggtgaggcag cgagcgtgga    6000
agcagctccg ggaggcctac tcaggaggag acttgcaagt tccacatcgc ttccaagttg    6060
gagattcagt ctatgttaga cgccaccgtg caggaaacct cgagactcgg tggaagggac    6120
```

```
cttatctcgt acttttgacc acaccaacgg ctgtgaaagt cgaaggaatc cccacctgga    6180
tccatgcatc ccacgttaag ccggcgccac ctcccgattc ggggtggaaa gccgaaaaga    6240
ctgaaaatcc ccttaagctt cgcctccatc gcgtggttcc ttactctgtc aataactcct    6300
caagttaatg gtaaacgcct tgtggacagc ccgaactccc ataaaccctt atctctcacc    6360
tggttactta ctgactccgg tacaggtatt aatattaaca gcactcaagg ggaggctccc    6420
ttggggacct ggtggcctga attatatgtc tgccttcgat cagtaatccc tggtctcaat    6480
gaccaggcca caccccccga tgtactccgt gcttacgggt tttacgtttg cccaggaccc    6540
ccaaataatg aagaatattg tggaaatcct caggatttct tttgcaagca atggagctgc    6600
gtaacttcta atgatgggaa ttggaaatgg ccagtctctc agcaagacag agtaagttac    6660
tcttttgtta acaatcctac cagttataat caatttaatt atggccatgg gagatggaaa    6720
gattggcaac agcgggtaca aaagatgta cgaaataagc aaataagctg tcattcgtta    6780
gacctagatt acttaaaaat aagtttcact gaaaaaggaa acaagaaaa tattcaaaag    6840
tgggtaaatg gtatgtcttg gggaatagtg tactatggag ctctgggag aaagaaagga    6900
tctgttctga ctattcgcct cagaatagaa actcagatgg aacctccggt tgctatagga    6960
ccaaataagg gtttggccga caaggacct ccaatccaag aacagaggcc atctcctaac    7020
ccctctgatt acaatacaac ctctggatca gtccccactg agcctaacat cactattaaa    7080
acagggcga aacttttag cctcatccag ggagcttttc aagctcttaa ctccacgact    7140
ccagaggcta cctcttcttg ttggcttttgc ttagcttcgg gcccaccta ctatgaggga    7200
atggctagag gagggaaatt caatgtgaca aggaacata gagaccaatg tacatgggga    7260
tcccaaaata agcttaccct tactgaggtt tctggaaaag gcacctgcat agggagggtt    7320
cccccatccc accaacacct ttgtaaccac actgaagcct ttaatcgaac ctctgagagt    7380
cagtatctgg tacctggtta tgacaggtgg tgggcatgta atactggatt aaccccttgt    7440
gtttccacct tggttttcaa ccaaactaaa gactttgcg ttatggtcca aattgtcccc    7500
cgggtgtact actatcccga aaaagcagtc cttgatgaat atgactatag atataatcgg    7560
ccaaaaagag agcccatatc cctgacacta gctgtaatgc tcggattggg agtggctgca    7620
ggcgtgggaa caggaacggc tgccctaatc acaggaccgc aacagctgga gaaggactt    7680
agtaacctac atcgaattgt aacggaagat ctccaagccc tagaaaaatc tgtcagtaac    7740
ctggaggaat ccctaacctc cttatctgaa gtggttctac agaacagaag ggggttagat    7800
ctgttatttc taaaagaagg agggttatgt gtagccttaa aagaggaatg ctgcttttat    7860
gtggatcatt caggagctat cagggactcc atgagcaagc tcagagaaag gttagaaaaa    7920
cgtcacaaag aaaagaggc tggccaagga tggtttgagg gatggttcaa caagtcccca    7980
tgggtgacca ccctgctttc tgctctaaca ggaccctag taatactgct cctgttgctt    8040
acagttgggc cttgcttaat taatcggttt gttgcctttg ttagagaaca agtgagtgca    8100
gttcggatca tggtacttag acagcagtac caaggccttc caagctaagg agaaactgac    8160
ctttagcctt cctagttcta agattagaac tattaacaag agaagaagtg gggaatgaaa    8220
ggatgaaaat gcaacctgac tctcccagaa cccaggaagt aataagaag ctctaaatgc    8280
cctcgaattc cagaccctgt tccctatagg taaaagatca tacttttgc tgttttaggg    8340
cttgctttct gctctgtaca aaactttgtg gaagggaaa acaggcccc tgagtatgtg    8400
cctctatgct tgaaacttct tgaaactgct cctaactgct tgtttggctt ctgtaaacct    8460
```

```
                                            -continued
gcttgcataa gataaaaaga ggagaagtca atcgcctaac cgaccccagt aagatcgggc    8520
gtgccacaaa atgttgaaaa tcctgataaa tatatcttgg tgacaatatg tctcccccac    8580
ccagagacag gcacaaacat gtaactccag aacaacttaa aattaattgg tccacaaagc    8640
gcgggctctc gaagttttga attgactggt ttgcgatatt ttaaaatgat tagtttgtaa    8700
aagcgcgggc tttgttatga acccataaa agctgtcccg actccacact cggggccgca    8760
gtcctctacc cctgcgtggc gtacgactgt gggcccagc gcgctcggaa taaaaatcct    8820
cttgctgttt gcatcaagac cgcttctcgt gagtgatttg gggtgtcgcc tcttccgagt    8880
caggacgaga gggattttaa ctcgactggc ctttca                              8916
```

ELIMINATION OF ENDOGENOUS PORCINE RETROVIRUS

CROSS-REFERENCE TO RELATED APPLICATIONS

The present application claims priority to U.S. Ser. No. 60/279,337, filed Mar. 28, 2001, herein incorporated by reference in its entirety.

STATEMENT AS TO RIGHTS IN INVENTIONS MADE UNDER FEDERALLY SPONSORED RESEARCH AND DEVELOPMENT

Not applicable.

BACKGROUND OF THE INVENTION

1. Field of the Invention

This invention relates to compositions and methods for detecting the presence of endogenous retroviruses, in particular, the detection of porcine endogenous retroviruses (PERV) in tissues useful as a xenograft.

2. General Background and State of the Art

The most common source of tissue used today as donor tissue for transplantation is the allograft (same species, different person). However, there are insufficient resources of human organs and cells for use as donor tissue. The shortage of human donor material has resulted in alternative solutions for transplantation. Xenotranplantation, which is the use of living tissue from non-human animals is one viable alternative. However, when using alternative sources, ethical, practical, biological and economic concerns must be considered. Therefore, among the animal species most suitable for use as a xenotranplant is the pig.

Examples of porcine tissue already being tested in clinical trials include fetal pig pancreatic islet cells for treating diabetes (Groth et al., Lancet 1994), pig neuronal cells for treating Parkinson's disease (Deacon et al., Nat Med 1997) and extracorporeal (ex vivo) pig liver or kidney perfusion for treating liver (Foley et al., Transplantation 2000, Levy et al., Transpl. 2000. 69: 272) or kidney failure (Breimer et al., Xenotransplantation 1996). However, as the potential for success increases the use of porcine tissue as a resource, the potential for introducing an infectious agent from the pig into the recipient becomes an increasing concern. Although risks associated with some pathogens can be reduced by breeding for and using specific-pathogen-free (SPF) animal colonies, this approach is not feasible for preventing infection from endogenous retroviruses, because these pathogens exist in the germine of all pigs.

Porcine Endogenous Retrovirus (PERV) is a C-type retrovirus that is permanently integrated in the pig genome. PERVs exist in the pig genome at an estimated 25–50 copies per cell. Early scientific reports dating back to the 1970's indicated that some porcine (pig) cells grown in culture produced type C retrovirus particles. This suggested their potential to be infectious. However, other studies of cells cultured directly from pig tissue (primary culture) showed no evidence of infectious potential. More recent reports indicate that there is a low frequency of PERV infection of human cells that are co-cultured with a pig cell line, PK15 (Le Tissier et al., Nature 1997; Patience et al., Nature Medicine, 1997). This reemphasized the concern regarding potential risk of PERV infection to human recipients of porcine tissue xenografts. Augmenting this risk is the use of immunosuppressive therapies necessary for preventing graft rejection by a recipient. Suppression of the recipient's immune system may also significantly increase the recipient's susceptibility to infection by PERV. Therefore, there is a need for methods to detect and monitor porcine tissues and cells for the presence of infectious PERV.

To date, there are three classes of PERV (PERV-A, PERV-B, and PERV-C). The differences between the three classes are primarily based on sequence differences in their envelope gene region. Recent identification of PERV sequences allows for development of molecular based detection methods. For example, methods that can detect specific sequences of DNA such as the polymerase chain reaction (PCR) can be used to identify the presence of PERV in a tissue sample. Keeping in mind that all pig genomes have PERV sequences, but that not all PERV are infectious, prescreening of a transplant tissue merely for presence of a PERV sequence is not a sufficient indicator of its infectious potential. Therefore, current methods for detecting the presence of PERV are limited by their inability to determine which PERV loci are infectious.

Thus, there is a need for methods and compositions capable of reducing the risk of transmission of PERV from porcine tissues suitable for use as xenografts. Particularly needed are compositions and methods for detecting the presence of infectious PERV in a biological sample.

INVENTION SUMMARY

The present invention provides compositions and methods for detecting porcine endogenous retroviruses (PERV). These methods and compositions are particularly effective in detecting the presence of PERV loci capable of producing infectious virus. The present invention provides methods for detecting the presence of PERV in samples useful for xenotransplantation.

In one embodiment, the invention provides compositions that are capable of detecting potentially infectious PERV using nucleic acid sequences comprising porcine sequences flanking infectious PERV insertion sites. The unique 3' flanking sequences or unique 5' flanking sequences can be used to provide nucleic acid probes that are specific for potentially infectious PERV loci. In addition, nucleic acids sequences and subsequences thereof from the PERV genome of three infectious PERV loci, G3, G19, and G28 can be used to provide nucleic acid probes, including primers (SEQ ID NO:137–139). Such genomic sequences can also be used to provide nucleic acid probes that are specific for potentially infectious PERV loci.

Accordingly, a unique 3' flanking sequence from a PERV locus can include any one of SEQ ID NO:6–35 or any nucleic acid sequence capable of hybridizing under suitably stringent conditions to any one of SEQ ID NO:6–35. Furthermore, the invention also provides nucleic acid sequences having suitable sequence identity, such as at least 80% sequence identity, to a porcine 3' end flanking sequence of an infectious PERV insertion site. The provided nucleic acid sequences and probes can be used for diagnosis, monitoring or screening of specific PERV loci in cells, tissues, or organs suitable for use as a xenotransplant.

The provided porcine sequences flanking potentially infectious PERV integration sites can be used as probes in methods for detecting presence of potentially infectious PERV in a biological sample. Suitable detection assays include use of the PERV probes in Southern Blot Analysis, PCR Analysis, or other molecular biological assay comprising formation of a PERV genomic target region:probe duplex and detection of the target region:probe duplex in the sample.

The invention further provides methods for making probes suitable for detecting the presence of potentially infectious PERV. Such methods include isolation of nucleic acid sequences which flank a PERV integration site and identification of the sequences as unique flanking sequences. Isolation of nucleic acid sequences flanking a PERV integration site can be by use of a conserved PERV sequence; or use of a conserved PERV sequence derived from the envelope region of a PERV sequence. The unique flanking sequences can be a unique 3' flanking sequence or, alternatively, can be a unique 5' flanking sequence. The unique 3' flanking sequences or unique 5' flanking sequences can be identified using DNA sequence analysis. Therefore, the invention also provides methods for detecting sequences capable of hybridizing to a unique 3' flanking sequence or a unique 5' flanking sequence.

Such methods include isolation of nucleic acid sequences which flank a PERV integration site and identification of the sequences as unique flanking sequences. Such methods include isolation of nucleic acid sequences which flank a PERV integration site and identification of the sequences as unique flanking sequences. The unique flanking sequences can be a unique 3' flanking sequence or, alternatively, can be a unique 5' flanking sequence suitable for detecting presence of potentially infectious PERV.

Therefore, the compositions of the present invention also provide methods for reducing the risk of transmission of PERV from a xenotransplant tissue to a host or recipient.

Accordingly in another aspect of the invention, methods for selecting animals free of specific PERV loci are provided. Pigs having a negative profile for a specific PERV locus or a potentially infectious PERV can be used to breed a pig for use as a xenograft donor. A selective breeding method would include determination of a pig's PERV allele polymorphism profile. Selection of those pigs having a profile that is negative for a specific PERV locus can then be made. Those having a negative PERV locus profile can be bred to obtain offspring whose genome are free of one or more specific PERV loci. An animal produced by the present invention can therefore be used as a source of xenograft tissue that is free of potentially infectious PERV loci, such as a G3 (SEQ ID NO:8), a G19 (SEQ ID NO:24) or a G28 (SEQ ID NO:33) locus.

BRIEF DESCRIPTION OF THE DRAWINGS

FIG. 2 shows a map of a vector including a PERV insert.

FIG. 3 shows a map of a PERV locus indicating locations of oligonucleotide primers useful for PCR analysis.

FIG. 4 illustrates allele polymorphism of PERV locus by Southern blot analysis.

FIG. 5 illustrates allele polymorphism of PERV locus by PCR analysis.

FIG. 6 shows identification of allele polymorphism of a PERV locus.

FIG. 7 shows identification of allele polymorphism of a PERV locus.

FIG. 8 shows a map of a PERV clone indicating locations of oligonucleotide primers useful for determination of 3' flanking sequences.

FIG. 9 shows a map of a PERV clone indicating locations of oligonucleotide primers useful for determination of 5' flanking sequences.

FIG. 10 shows a flow diagram of a method of subcloning a PERV locus.

FIG. 11 shows the complete G3 PERV genome (SEQ ID No: 137).

FIG. 12 shows the complete G19 PERV genome (SEQ ID No: 138).

FIG. 13 shows the complete G28 PERV genome (SEQ ID No: 139).

DETAILED DESCRIPTION OF THE PREFERRED EMBODIMENTS

Figure 1:
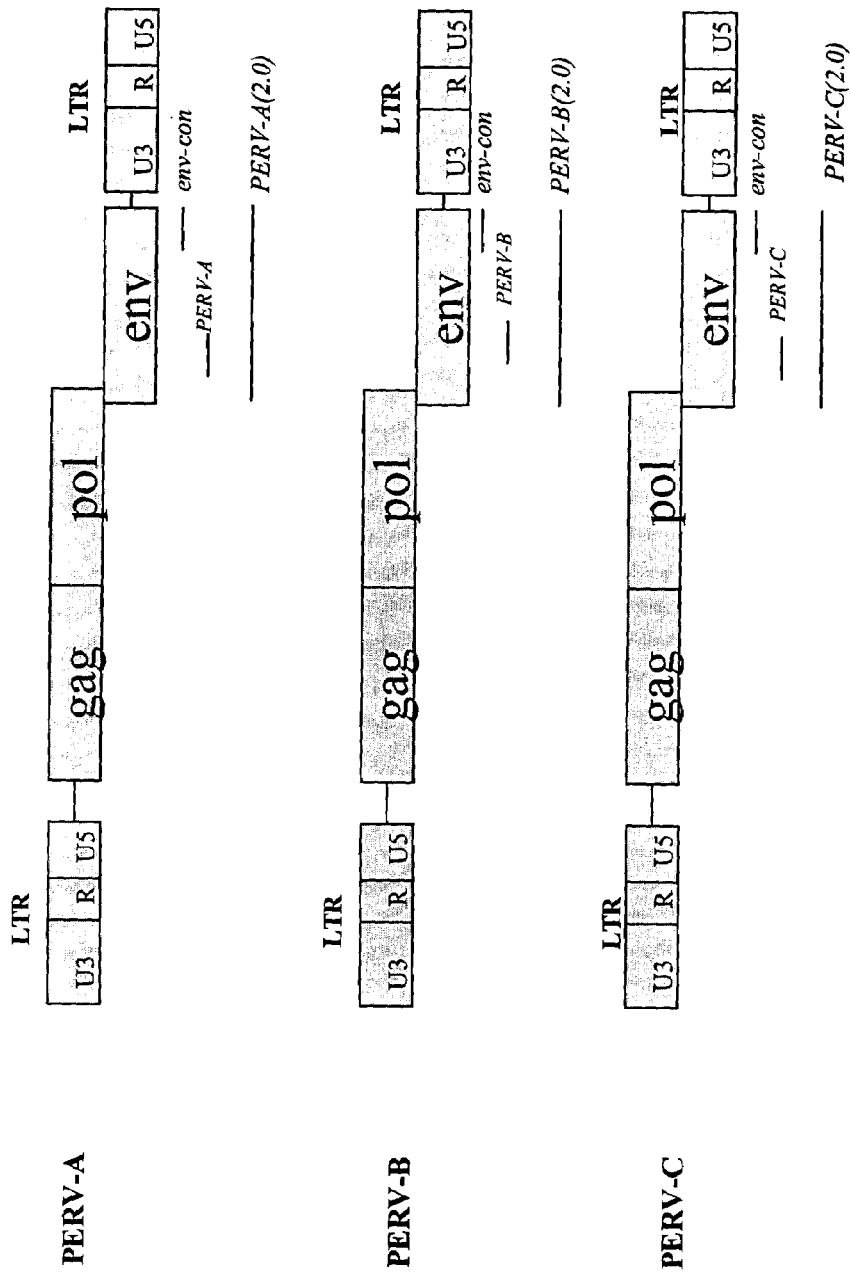
FIG. 1 shows regions of PERV genes used to develop probes

The present invention includes compositions and methods for detecting porcine endogenous retrovirus (PERV) and methods for making probes suitable for use in detecting PERV. In particular, compositions comprising molecular probes such as nucleic acid sequences specific for infectious endogenous retroviruses are provided. Also provided are methods of making and using such probes as well as assays employing such probes. The present invention is applicable to the breeding or selection of donor transplant tissue, for example, porcine tissue, that is free of infectious endogenous retroviruses. The foregoing strategy can be utilized with any infectious or potentially infectious endogenous retroviral sequence to practice the method of the invention and accordingly, the present invention is not specifically limited to compositions and methods of making and detecting PERV loci alone nor only those PERV loci specifically disclosed herein. While the present invention is not so limited, an appreciation of various aspects of the invention will be gained through a discussion of the examples provided below.

PERV belongs to the mammalian type C class of retroviruses. Attachment of the retrovirus to a host cell prior to infection is mediated by viral surface proteins, which are encoded by the envelope (Env) gene region of the retroviral sequence. These viral surface proteins bind host cell surface proteins. The Env gene proteins play a role in determining host range specificity. There are three classes of PERV identified thus far based on their Env gene sequences. These sequences have been published and deposited (Perv-A=Genbank Accession No: AF038601; Perv-B=EMBL Accession No: PERY17013; PERV-C=Genbank Accession No: AF038600).

PERV exists in the genome of all pigs. As discussed previously, the ability of some cultured pig cells to infect human cells in vitro raises the concern that pig tissue used for xenotransplantation may be capable of transmitting infectious PERV to the recipient. Although co-culture assays have identified some pig cells that are infectious by their ability to infect human cell lines in culture, this technique cannot be used as a reliable screening assay due to its low sensitivity. For example, co-culture with activated lymphocytes or hepatocytes from one source of transgenic pig failed to show any evidence of productive infection. This could indicate either that the particular line of transgenic pig did not have infectious PERV, that the sequences were not activated, or that PERV sequences from these pigs are not able to infect the particular line of human cells used.

Multiple PERV proviral sequences exist within a pig genome. The degree of homology within these sequences is high, making them difficult to distinguish by sequence polymorphism. One embodiment of the present invention is based upon each PERV proviral integration into the pig genome representing a unique event. PERV clones were isolated from a genomic library constructed using DNA from a transgenic pig in our herd, and unique sequences flanking the 3' and 5' region of each PERV gene were identified as described more fully in the examples below. The pigs are known and described as 603-57 transgenic line (Byrne et al. 1997 *Transplantation* 63:149–155). The pigs carry the human CD59 and human CD55 transgenes. Pig d711, a DNA donor for a porcine genomic library was obtained by crossing a transgenic founder pig (603-57) to a nontransgenic sow. Both pigs were from a Camborough 15 Line (Pig Improvement Company, Franklin, Ky.). A Camborough 15 pig is 25% Large White, 25% Landrace, and 50% Duroc. Alternatively, PERV clones can, if desired, be isolated from a genomic library using DNA from any pig or any transgenic pig whose organs or tissues are suitable for use in xenotransplantation.

As used herein, the term "unique", "unique flanking" or "unique flanking sequence" refers to those sequences from a pig genome which flank a PERV integration site and which can be distinguishable from non-PERV flanking genomic sequence based on flanking sequence polymorphism.

Since those PERV loci that have an envelope gene are competent to be infectious, this region of the PERV sequence was used to construct probes for isolating each PERV sequence. Based on known PERV envelope sequences, conserved envelope sequence probes (env-cons) which correspond to the transmembrane domain of the PERV envelope gene were constructed: PERV-A (1881–2133 bp, Y12238) (SEQ ID NO:1); PERV-B (2572–2824 bp, Y12239) (SEQ ID NO:2); and PERV-C (7227–7479 bp, AF038600) (SEQ ID NO:3). Additional probes used to screen the genomic library included: PERV-A (94–2133 bp, Y12238) (SEQ ID NO:4) and PERV-B (794–2823, Y12239) (SEQ ID NO:5). However, any region of a PERV sequence, such as for example, a sequence from a gag, pol, signal or LTR region of a PERV sequence could be used to construct probes for isolating a PERV locus.

All probes were initially generated by PCR amplification as described in the examples below. Any method, however, for nucleotide sequence replication can be used to generate a PERV probe. Such methods include, for example, ligase-chain reaction, isothermal amplification, or use of more basic cloning techniques such as use of cloning vectors or plasmids, and propagation from a bacterial stock. For additional details and explanation of nucleotide sequence amplification or replication techniques, see Ausubel et al. *Current Protocols in Molecular Biology* (Wiley Interscience Publishers, 1995); US Dept Commerce/NOAA/NMFS/NWFSC Molecular Biology Protocols (URL:http://research.nwfsc-.noaa.gov/protocols.html); or Protocols Online (URL: www.protocol-online.net/molbio/index.htm).

PERV envelope probes were used to screen a pig genomic library and isolate PERV loci. Sequence analysis of each clone into the flanking genomic DNA identified each clone as unique or not unique. As set forth in Examples 2–4, the PERV clones (G3–25 (SEQ ID NO:8); G19-A45 (SEQ ID NO:24)and G28-402A (SEQ ID NO:33)) were made. Therefore, the invention provides methods of obtaining clones and their use in constructing probes for identification of unique PERV flanking sequences.

The invention further provides newly identified and isolated nucleotide sequences (SEQ ID NOS:6–35; and 101–118) flanking integrated PERV genes. Probes corresponding to the 3' flanking PERV integration sequences were then obtained by amplification using 5' primers (5'G1–5'G30) (SEQ ID NOS:36; 38; 40; 42; 44; 46; 48; 50; 52; 54; 56; 58; 60; 62; 64; 66; 68; 70; 72; 74; 76; 78; 80; 82; 84; 86; 88; 90; 92; and 94) and 3' primers (3'G1–3'G30) (SEQ ID NOS:37; 39; 41; 43; 45; 47; 49; 51; 53; 55; 57; 59; 61; 63; 65; 67; 69; 71; 73; 75; 77; 79; 81; 83; 85; 87; 89; 91; 93; and 95). Primers used as pairs for amplification are listed in Example 2, Table 1.

The size or length of genomic flanking sequence sufficient to allow for identification of a unique PERV locus was approximately 300–500 bp of DNA downstream (for identification of unique 3' flanking sequence) or upstream (for identification of unique 5' flanking sequence) of each individual PERV gene. However, as would be known to one skilled in the art, a length of approximately less than 100 bp, or greater than 1000 bp, or of 100–2000 bp, can also be used if necessary, depending upon the extent of polymorphism in the flanking region, the degree of comparison desired, or the level of sequence distinction required.

A flanking sequence was identified as unique by DNA sequence analysis and comparison. Sequence reactions and analysis was performed using standard sequence reaction kits (PE Applied Biosystems, Foster City, Calif.), but can be performed by other methods well known in the art and described, for example, in Sambrook et al. *Molecular Cloning: A Laboratory Manual* (New York: Cold Spring Harbor Press, 1989) or in Innis et al., PCR Strategies (*Academic Press, Inc.: NY.,* 1995). In some cases, sequence information was obtained from the genomic DNA flanking the upstream (5' region) of the PERV gene. As would be apparent to one skilled in the art, if sequence analysis is performed on 5' flanking sequence, then sequences would be compared to other 5' flanking sequence and not 3' flanking sequences. The size or length of flanking sequence sufficient for DNA sequence analysis and comparison was similar to that for the 3' flanking regions.

The unique 3' flanking sequences from each PERV locus provides locus specific flanking probes. Based on the unique 3' flanking sequence from each PERV locus, a locus specific probe was obtained for each locus (SEQ ID NOS:6–35) also referred to herein as G1–G30, and as described more fully in the Examples below. As used herein, a "unique 3' flanking sequence" is used to refer to a genomic pig sequence that is a unique sequence flanking the 3' end of a PERV integration locus. A unique 3' flanking sequence as used herein also refers to any nucleic acid sequence having at least about 80%, 90%, 95% or greater DNA sequence identity or homology with the 3' flanking sequence shown in Table 1, which sets forth the 3' probe and primer sets for each PERV locus (G1–G30); (SEQ ID NOS:6–35).

TABLE 1

| Locus | Type | 3'probe (bp) | Primer set | |
|-------|------|------|------|------|
| | | | 5' primer(base) | 3' primer(base) |
| G1 | B | 307 | 5'G1(20) | 3'G1(25) |
| G2 | A | 324 | 5'G2(23) | 3'G2(24) |
| G3 | B | 337 | 5'G3(23) | 3'G3(24) |
| G4 | B | 329 | 5'G4(20) | 3'G4(20) |
| G5 | A | 263 | 5'G5(22) | 3'G5(22) |
| G6 | A | 289 | 5'G6(22) | 3'G6(23) |
| G7 | B | 316 | 5'G7(24) | 3'G7(24) |
| G8 | B | 317 | 5'G8(22) | 3'G8(24) |
| G9 | B | 466 | 5'G9-216(25) | 3'G9-680(18) |
| G10 | A | 310 | 5'G10(24) | 3'G10(21) |
| G11 | B | 375 | 5'G11(18) | 3'G11(21) |
| G12 | B | 277 | 5'G12(25) | 3'G12(21) |
| G13 | B | 293 | 5'G13(24) | 3'G13(22) |
| G14 | B | 275 | 5'G14(24) | 3'G14(21) |
| G15 | A | 232 | 5'G15(19) | 3'G15(18) |

TABLE 1-continued

| Locus | Type | 3'probe (bp) | Primer set 5' primer(base) | 3' primer(base) |
|---|---|---|---|---|
| G16 | A | 354 | 5'G16(22) | 3'G16(20) |
| G17 | A | 535 | 5'G17(25) | 3'G17(21) |
| G18 | A | 397 | 5'G18(18) | 3'G18(19) |
| G19 | A | 251 | 5'G19(23) | 3'G19(20) |
| G20 | A | 360 | 5'G20(18) | 3'G20(18) |
| G21 | A | 392 | 5'G21(21) | 3'G21(24) |
| G22 | A | 335 | 5'G22(24) | 3'G22(24) |
| G23 | B | 416 | 5'G23(24) | 3'G23(24) |
| G24 | A | 378 | 5'G24(24) | 3'G24(24) |
| G25 | B | 358 | 5'G25(24) | 3'G25(21) |
| G26 | A | 228 | 5'G26(21) | 3'G26(25) |
| G27 | B | 384 | 5'G27(20) | 3'G27(21) |
| G28 | A | 464 | 5'G28(24) | 3'G28(25) |
| G29 | A | 370 | 5'G29(18) | 3'G29(20) |
| G30 | A | 317 | 5'G30(24) | 3'G30(21) |

As used herein, a "unique 5' flanking sequence" is used to refer to a genomic sequence flanking the 5' end of a PERV integration locus. A unique 5' flanking sequence as used herein also refers to any nucleic acid sequence having at least about 80%, 90%, 95% or greater DNA sequence identity or homology with a 5' flanking sequence (SEQ ID NOS:101–118) corresponding to PERV loci, or as identified using the methods described herein.

The invention further provides those endogenous retroviral sequence loci having infectious potential. The ability of each individual PERV gene to produce infectious virus was assessed. Plasmid containing one PERV gene as well as a selectable drug resistance marker was transfected into 293 cells. The cell supernatant from drug-resistant clones was assayed for RT activity. Any clone which gave rise to measurable RT activity was then analyzed for the ability to produce infectious retrovirus by co-culturing the supernatant with fresh 293 cells. Cell supernatant from this culture was assayed for RT activity, and those cells collected on a weekly basis were analyzed to detect PERV integration. Thus far, three PERV clones, G3–25 (SEQ ID NO:8); G19-A45 (SEQ ID NO:24), and G28-402 A (SEQ ID NO:33) when transfected into 293 cells, result in RT activity in the supernatant. Additional endogenous retroviral sequences with infectious potential from other animals can also be identified using the probes, screening methods and strategy described above to identify novel endogenous retroviral integration sites.

The invention further provides assays for detecting the presence of specific endogenous retrovirus that are potentially infectious in a sample, including organs, tissues, cells, and fluids. Samples identified as being positive or negative for specific infectious endogenous retroviral sequence are determined by testing for presence or absence of novel flanking sequences, such as for example, a unique 3' flanking or a unique 5' flanking sequence associated with a specific PERV gene.

Analysis of PERV loci or any other endogenous retroviral sequence locus can be by methods such as Southern blot analysis, conventional PCR amplification. See, e.g., Innis et al., *PCR Strategies* (Academic Press, Inc.: NY., 1995); Dieffenbach et al., *PCR Primer: A Laboratory Manual* (New York: Cold Spring Harbor Press, 1995), denaturing gradient gel-electrophoresis (Myers, et al., 1987. Meth. Enzymol. 155: 501), single-strand conformational analysis (Hayashi, 1992. Genet Anal Biomol E 9: 73), ligase-chain reaction (Barany. 1991. Proc Natl Acad Sci 88: 189), isothermal amplification (Fahy et al. 1991. PCR Methods Appl 1: 25), branched chain analysis (Urdea. 1993. Clin Chem 39: 725), and signal amplification techniques such as Third Wave's linear amplification. DNA sequence analysis may also be achieved by detecting alteration in electrophoretic mobility of DNA fragments in gels with or without denaturing agents. Samples containing PERV insertions adjacent to a unique 3' flanking sequence or a unique 5' flanking sequence can also be visualized by high resolution gel electrophoresis or distinguished according to differences in DNA sequence melting points. See, e.g., Myers et al., *Science*. 230: 1242 (1982). Methods for detecting presence of specific sequences include detection techniques such as fluorescence-based detection methods, immune-based assays such as RIA, antibody staining such as Western blot analysis or in situ hybridization, using appropriately labeled probe, based on the sequences provided herein. Using the methods and strategy described hereinabove, any unique 3' flanking sequence or unique 5' flanking sequences in addition to those specifically disclosed herein can be identified and used as probes for detection or analysis of PERV presence.

PERV Allele Polymorphism

The invention also provides a method to screen for the existence of PERV with potential to infect in a sample by determining PERV loci allele polymorphism. Identification of allelic polymorphism in a sample allows for selection of animals suitable for use either directly as a xenograft tissue donor or as a breeder to provide a source of xenograft tissue that is negative for, or free of PERV sequence that are infectious or have potential to be infectious. One method for detecting presence of a PERV locus is analysis of allele polymorphism by Southern blot using a unique flanking sequence as a probe, such as a unique 3' flanking sequence or a unique 5' flanking sequence. Using Southern blot analysis, a different banding pattern will emerge if PERV is present depending upon whether PERV is present on both alleles, on one allele, or on neither allele. Southern analysis of three infectious PERV loci, G3 (SEQ ID NO:8, see also SEQ ID NO:137 (complete G3 PERV genome), FIG. 11); G19 (SEQ ID NO:24, see also SEQ ID NO:138 (complete G19 PERV genome), FIG. 12); and G28 (SEQ ID NO:33, see also SEQ ID NO:139 (complete G28 PERV genome), FIG. 13) (Examples 5 & 6) demonstrate that all three loci exhibit allele polymorphism. The olymorphic genome sequences produce RT activity. These PERV loci, including genome and flanking sequences, can therefore be detected using the probes derived from the PERV and PERV loci sequences of the invention. This will allow for breeding of animals that are negative for G3; G19, and/or G28 by crossing or mating an animal that is homozygous-negative for both alleles of a particular locus with another animal that is homozygous-negative for both alleles of the same locus. Alternatively, animals that are hemizygous can be used as F0 breeders. In this latter case, subsequent screening will need to be performed to identify offspring, which are homozygous negative for the G3; G19, and/or G28 loci.

Sequences useful for constructing probes suitable for use in detecting presence of PERV include any one of G1–G30 (SEQ ID NOS:6–35) or any nucleic acid sequence having at least about 80%, 90%,95% or greater sequence identity or homology with a unique 3' flanking sequence (SEQ ID NOS:6–35) as determined by a Blast search. "Percent (%) sequence identity" or "percent (%) sequence homology" with respect to sequences identified herein is defined as the percentage of nucleic acid residues in a candidate sequence that are identical with the nucleic acid residues disclosed herein (any one of SEQ ID NOS:6–35), after aligning the sequences and introducing gaps, if necessary to achieve maximum percent sequence identity, and not considering any conservative substitutions as part of the sequence identity. Methods for performing sequence alignment and determining sequence identity are well known in the art, may be performed without undue experimentation, and calculations of % identity values may be obtained for example, using available computer programs such as WU-BLAST-2 (Altschul et al., *Methods in Enzymology* 266:460–480 (1996). One may optionally perform the alignment using set default parameters in the computer software program (Blast search, MacVector and Vector NTI).

Based upon the restriction map of a particular locus, a banding pattern can be predicted when the Southern blot is hybridized with a probe which recognizes a unique flanking sequence, such as a unique 3' flanking sequence. The level of stringency of hybridization used can vary depending upon the level of sensitivity desired, a particular probe characteristic, such as probe length and/or annealing temperature, or degree of homology between probe sequence and genomic sequence flanking a 3' or a 5' region of a PERV locus. Therefore, considerations of sensitivity and specificity will determine stringency of hybridization required for a particular assay.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperatures. The higher the degree of desired homology between the probe and hybridizable sequence, the higher the relative temperature that can be used. For additional details and explanation of stringency of hybridization reactions, see Ausubel et al. *Current Protocols in Molecular Biology* (Wiley Interscience Publishers, 1995) or Protocols Online URL: (www.protocolonline.net/molbio/index.htm).

"Stringent conditions" or "high-stringency", as defined herein, may be identified by those that use low ionic strength and high temperature for washing, for example 0.1×SSC, 0.2% SDS @65–70° C. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Moderately-stringent conditions" may be identified as described by Sambrook et al., supra, and include the use of washing solution and hybridization conditions (e.g. temperature, ionic strength, and % SDS) less stringent that those described above. Onbe example of moderately stringent conditions is 0.2×SSC, 0.1% SDS @58–65° C. Exemplary "moderately stringent hybridization conditions" include a hybridization in a buffer of 40% formamide, 1 M NaCl, 1% SDS at 37° C., and a wash in 1×SSC at 45° C. The skilled artisan will recognize how to adjust temperature, ionic strength, etc. as necessary to accommodate factors such as probe length, degree of homology between probe and target site and the like. Therefore, in addition to the unique 3' flanking sequences and unique 5' flanking sequences described herein, it is contemplated that additional or alternative probe sequences which vary from those specifically disclosed herein (SEQ ID NOS:6–35) will also be useful in screening for PERV loci having infectious potential.

Another method to determine the existence of an allele containing or missing a specific PERV integration utilizes PCR analysis. For example, presence or absence of a PERV locus in a sample can be determined by detecting a change in size of the amplified product in comparison to the expected size product from a known genotype. Genomic DNA from a test sample is analyzed with specific primers that flank a particular PERV locus. Suitable primers include SEQ ID NOS:36–95; useful as primer pairs as disclosed in Table 2. FIG. 3 shows an example of identification of allele polymorphism using PCR analysis. Primer pairs are selected so that the 5' (forward) primer corresponds to a sequence flanking the 5' end of a PERV gene (Gn-5'). The 3' (reverse) primer will correspond to a sequence flanking the 3' end of a unique 3' flanking sequence such as G3 (SEQ ID NO:8); G19 (SEQ ID NO:24) or G28 (SEQ ID NO:33). In a sample containing an allele, which carries the PERV integration, the PCR reaction will fail when performed under standard conditions due to the large size of the expected PCR product (approximately 9 KB). Amplification of a smaller (approximately 300 bp) PCR product will indicate absence of PERV on at least one allele. Further confirmation of the presence of PERV in the sample resulting in a negative PCR product can be performed by a second round of PCR using a PERV specific primer and a primer specific to the flanking sequence or can be confirmed by sequence analysis using conventional procedures as described in Sambrook et al., supra.

The present invention includes methods of detecting the potential for infection by a specific PERV by detecting presence of a PERV locus-specific integration site using novel flanking sequences. The sample to be tested or analyzed may be obtained from any biological source known to or suspected to carry potentially infectious PERV, and is preferably taken from an animal prior to use as a donor. For example, the sample may be a cell sample, tissue sample, or biological fluid, such as blood, urine, semen, saliva, sputum, tissue culture fluid, ascitites fluid, synovial fluid, and the like. The sample may also be a hair sample where DNA from the follicle can be isolated for analysis. A laboratory research sample such as a cell culture or embryo culture can also be used as the test sample. The sample is collected and processed for genomic DNA using methods well known to those skilled in the art.

The molecular based assays described herein, such as the PCR based assay, are ideal in that they have a high degree of sensitivity and specificity, thereby reducing the chance for false-positive or false-negative results. Alternatively, the unique flanking sequences (unique 3' flanking sequences or unique 5' flanking sequences) can be used to develop probes for use in a DNA detection method such as, for example, a conventional Southern blot assay. Probes suitable for such screening assays can comprise any one of the unique flanking sequences disclosed herein. For example, a probe suitable for use in a Southern blot assay would include a unique 3' flanking sequences such as SEQ ID NO:8; SEQ ID NO:24 or SEQ ID NO:33. Furthermore, detection of a potentially infectious PERV locus could be performed indirectly by use of sequences capable of hybridizing or complexing to the unique flanking sequences described herein. Methods for performing Southern blot assays are well known in the art and described in Sambrook et al., supra. Therefore, the invention also provides an assay kit for the detection of PERV loci in a sample. The assay kit will preferably contain necessary reagents and tools for reacting the sample with a PERV detection probe.

The provided porcine sequences flanking potentially infectious PERV integration sites can also be used to generate pigs whose genome lacks potentially infectious PERV.

Such "knock-out" pigs whose genome are free of one or more specific PERV loci, can be produced using the unique 3' flanking sequences or unique 5' flanking sequences with standard recombination-based techniques well-known in the art and described, for example in te Riele et al., Highly efficient gene targeting in embryonic stem cells through homologous recombination with isogenic DNA constructs. *Proc. Natl. Acad. Sci.* U.S.A. 89:5128 (1992) and Rulicke T. Transgenic technology: an introduction, *Int J. Exp Pathol* 77:243 (1996). The "knock-out" pigs having a negative profile for a specific PERV locus or a potentially infectious PERV can be used directly as a source of donor tissue or can be used to further breed pigs for use as a xenograft donor.

The present invention is further illustrated by the following examples.

EXAMPLES

Commercially available reagents referred to in the Examples were used according to manufacturer's instructions unless otherwise indicated. The source of those cells identified in the following examples, and throughout the specification, is human 293 cells (ATCC: CRL-1573). Unless otherwise noted, the present invention uses standard procedures of recombinant DNA technology, such as those described in: Sambrook et al., supra; Ausubel et al. *Current Protocols in Molecular Biology On CD-ROM* (Green Publishing Associates and Wiley Interscience, N.Y., 1993); Ausubel et al. *Short Protocols in Molecular Biology.* 4$^{th}$ Edition (Wiley Interscience, N.Y., 1999); Innis et al., *PCR Protocols: A Guide to Methods and Applications* (Academic Press, Inc.: N.Y., 1990); Gait, *Oligonucleotide Synthesis* (IRL Press: Oxford, 1984); Freshney, *Animal Cell Culture.* 1987; Cell and Molecular Biology Online (URL: www.cellbio.com/protocols.html); Protocols Online (URL: www.protocol-online.net/molbio/index.htm).

Example 1

The following is provided for exemplary purposes only and to further aid in the understanding of the invention. As is apparent from the disclosure provided herein, one skilled in the art can make, use or obtain any clone or clones to unique flanking sequences of PERV loci using the methods as exemplified below and described herein.

Cloning of Unique Flanking Sequences

Construction of Pig Genomic Library

All unique 3' flanking sequence and unique 5' flanking sequence clones were isolated from a genomic pig library constructed as follows:

High molecular weight (>100 kb) genomic liver DNA from a transgenic (CD59/DAF) male pig (for example, an F2 outcross consisting of Large White, Landrace, and Duroc) was partially digested with Sau3AI, and 9–24 KB fragments were isolated by sucrose gradient ultracentrifugation. The fragments were cloned into a Lambda FIX II vector (Stratagene, Calif.) to construct a pig genomic library.

The amplified library titer was 5.2×10$^9$ pfu/ml. Nine million phage were screened using several different probes, all of which detect the PERV envelope gene. It is the envelope sequence of a PERV gene that is responsible for its ability to infect a cell. Envelope probes were chosen to restrict isolation of PERV sequences to only those PERV loci having infectious potential, and therefore to those sequences which carry an envelope gene.

Probes Used to Screen Porcine Genomic Library

PERV loci in the transgenic pig library that contain a PERV envelope gene were isolated. Those PERV loci that have an envelope gene will be competent to be infectious. Therefore, various probes were generated using published PERV envelope sequences. See, for example, Akiyoshi et al., (*J. Virology.* 72:4503 1998) and Le Tisser et al., (*Nature.* 389:681, 1997).

Referring to FIG. 1, probes using PERV envelope sequences were generated and used to screen the porcine genomic library. PERV probe "env-cons" corresponds to the transmembrane domain of the PERV envelope gene, and has a high degree (about 99.6%) homology between PERV-A and PERV-B as per sequences Y12238, Y12239, deposited in GenBank (Le Tisser et al. *Nature,* 389:681, 1997). There is 80.6% homology between PERV-A and PERV-C env-cons region, based on the sequences in GenBank (Genbank Accession No: AF03860 and AF38600, respectively) as described in Akiyoshi et al., (*J. Virology* 72:4503, 1998). The env-cons probe was generated by PCR amplification using primers Env5(1) (SEQ ID NO:96) and Env4c (SEQ ID NO:97), based upon published sequence, and genomic DNA as the template. Probes designated "PERV-A" (SEQ ID NO:4) and "PERV-B" (SEQ ID NO:5) correspond to the entire envelope gene from either PERV-A or PERV-B, and were generated by PCR amplification using primers "5env" (SEQ ID NO:98) and "Env4C" (SEQ ID NO:97), and clones isolated as described above, as template DNA. These clones were originally isolated using "env-cons" PERV-A (SEQ ID NO:1), PERV-B (SEQ ID NO:2) or PERV-C (SEQ ID NO:3) and determined to belong to either the PERV-A family or the PERV-B family.

Primers were designed using MacVector primer design program (Oxford Molecular, Madison, Wis.) and synthesized by Gibco BRL (Life Technologies, Inc., Rockville, Md.) to amplify the env-cons probe by PCR. Primers synthesized:

```
Env5(1):
5'CTTCTATGTAGATCACTCAGGAGCC3'    (SEQ ID NO:96)
Located 290 bp upstream of env stop codon,
PERY 17013.

Env4c:
5'CTGGACTGCACTCACTCGTTCTCT3'    (SEQ ID NO:97)
Located 56 bp upstream of env stop codon,
PERY 17013.
```

The PCR Reaction Used:

| | |
|---|---|
| Pig genomic DNA | 500 ng |
| 10X Taq DNA polymerase buffer | 5 ul |
| dNTPs (2.5 mM/each) | 4 ul |
| Env5(1) (20 pmol/ul) | 1 ul |
| Env4c (20 pmol/ul) | 1 ul |
| Taq (5 u/ul) | 0.5 ul |
| Add ddH20 to total | 50 ul |

PCR Program:

Initial denaturation for 3 min @95° C., followed by 35 cycles of:

95° C. for 0.5 min
55° C. for 0.5 min
72° C. for 0.5 min;
extension for 7 min at 72° C.

Primers were designed using MacVector primer design program (Oxford Molecular, Madison, Wis.) and synthesized by Gibco BRL (Life Technologies, Inc., Rockville, Md.) to amplify the envelope gene from either PERV-A or PERV-B using PCR:

5env: 5'CAGTCTATGTTAGACGCCACCGTG3' (SEQ ID NO:98)
(93 bp upstream of env start site based on
PERY 17013 sequence deposited in GenBank by
Toenjes (Czauderna, et al., 2000. J. Virol.
4028–38).

Env4c: 5'CTGGACTGCACTCACTCGTTCTCT3' (SEQ ID NO:97)
(56 bp upstream of env stop codon based on
PERY 17013 sequence deposited by Toenjes).

The PCR Reaction Used:

| PERV lambda clone DNA | 50 ng |
| 10X Taq DNA polymerase | 5 ul |
| dNTPs (2.5 mM/each) | 4 ul |
| 5env (20 pmol/ul) | 1 ul |
| Env4c (20 pmol/ul) | 1 ul |
| Taq (5 u/ul) | 0.5 ul |
| Add ddH20 to total | 50 ul |

PCR Program:

| 95° C., 3 min | |
| 35 cycles of | 95° C., 0.5 min |
| | 55° C., 0.5 min |
| | 72° C., 2 min |
| | 72° C., 7 min |
| 4° C. hold. | |

Identification of PERV Loci By Unique 3' Porcine Genomic Flanking Sequences:

Multiple PERV proviral sequences exist, and have similar nucleotide sequence, making them difficult to distinguish by sequence polymorphism. However each PERV proviral integration into the pig genome represents a unique event. PERV loci were identified as unique based on sequence analysis of genomic DNA flanking each PERV gene. Approximately 300–500 bp of genomic DNA downstream (3'flanking) of each individual PERV gene was sequenced using an ABI automated sequencer (Perkin Elmer, Foster City, Calif.). In some cases, sequence information was obtained from the genomic DNA flanking the upstream 5' flanking region of the PERV gene as well, which is described below.

Identification of PERV Loci By Unique 5' Porcine Genomic Flanking Sequences

The strategy for obtaining unique 5' flanking sequences was essentially similar as that used for obtaining unique 3' flanking sequences, with the difference that reverse primers, such as LTR34C (SEQ ID NO:99) or LTR100C (SEQ ID NO:100), were used to sequence DNA flanking the upstream 5' flanking region of PERV loci. Referring to FIG. 9, unique 5' flanking sequences were determined from amplification of PERV lambda clone DNA using gag3' and T3 or T7 oligonucleotide primers. Amplification with these primer pairs generated fragments corresponding to 5' flanking sequences containing 5'LTR and portion of gag sequence of PERV. The PCR product was then sequenced using either LTR34C (SEQ ID NO:99) or LTR100 (SEQ ID NO:100) to obtain 5' flanking sequence. The 5' flanking probe can also be amplified with the Gn-F and Gn-R oligonucleotide primers, with Gn-5' (See Table 2, below, for listing of Gn-5' primer sequences) as a primer used in allelic polymorphism analysis. Using the methods as described herein, unique 5' flanking sequences (SEQ ID NOS:101–118) from each PERV locus were identified.

TABLE 2

Gn-5' primer sequences

| LOCUS | Gn-5' | SEQUENCE | SEQ ID NO: |
|---|---|---|---|
| G1 | G1-5' | 5'TACTCCTCCGCCATCTTGTC3' | 119 |
| G2 | G2-5' | 5'TCACTGAGGCACAGGAAGAC3' | 120 |
| G3 | G3-5' | 5'CATCATCTTAGAGCAGGTGC3' | 121 |
| G4 | G4-5' | 5'TCGTCAACCCACTGAGCAAG3' | 122 |
| G7 | G7-5' | 5'GCCAAATGTTTATCAAGCACCTGC3' | 123 |
| G8 | G8-5' | 5'GAAGCACAGAATAGTCAAGGC3' | 124 |
| G10 | G10-5' | 5'AAGCAACCCTTCTCCATCCTGG3' | 125 |
| G13 | G13-5' | 5'TTCTGTGCTGTAGGCTTGC3' | 126 |
| G14 | G14-5' | 5'AGGAGGGGCAAAGAAACCAG3' | 127 |
| G15 | G15-5' | 5'GCTGGAAGAGATGCTAAAGG3' | 128 |
| G17 | G17-5' | 5'AGGTAAGGCACAGGCAAAG3' | 129 |
| G19 | G19-5' | 5'AAAACTCTCAGGGGCTGCTGTG3' | 130 |
| G20 | G20-5' | 5'TTACGGAGCATCACCATCG3' | 131 |
| G22 | G22-5' | 5'GATGAGCCCAGGAAAATG3' | 132 |
| G24 | G24-5' | 5'TCCCTTTTACAACTCTGCC3' | 133 |
| G26 | G26-5' | 5'GCCTTTGTTTGTGTTTGGTAGC3' | 134 |
| G27 | G27-5' | 5'TTCCAGTTCCCTTTCTCCCC3' | 135 |
| G28 | G28-5' | 5'AAAAGAACTCTCTGGAAGGC3' | 136 |

Sequence reactions were done using ABI Prism dRhodamine Terminator Cycle Sequencing Ready Reaction Kits from PE Applied Biosystems (Perkin Elmer, Foster City, Calif.). A 20 μl sequence reaction consisted of 30–1000 ng of a DNA template (lambda DNA, plasmid DNA or PCR product), 8 μl terminator ready reaction mix, and 4 pmol of each primer. The PCR sequence programs were: 96° C. for 1 min, 35 cycles of 96° C. for 10 sec, 52° C. for 10 sec and 60° C. for 4 min. The PCR products were purified using a centri-sep column according to manufacture's protocol (Princeton Separations, Inc., Adelphia, N.J.), and sequences were analyzed by an ABI Prism 310 genetic Analyzer (Perkin Elmer, Foster City, Calif.).

3' Genomic Flanking Probes

Based on the unique 3' flanking sequences from each PERV locus, locus-specific 3' flanking probes were amplified using specific primers (SEQ ID NOS:36–95). Each probe was subcloned into a TA cloning vector (Invitrogen, Carlsbad, Calif.), and sequence-confirmed.

Blast Search of 3' Flanking Sequences Against Databases

The sequences of 3' flanking probes of all PERV loci identified as described above, were searched against 11 databases (nr, dbests, dbsts, mouse ests, human ests, other ests, pdb, patents, epd, gss, and htgs, Altschul et al., 1997. Nucl. Acids Res. 3389–3402). The following PERV loci had no significant homologies with any of the sequences deposited in the above identified databases: G1–8, G10–12, G14–16, G19–22, G24–26 and G28–30. The PERV G6, G9, G13, G17, G18, G23, and G27 had homologies with certain database sequences as listed below in Table 3.

TABLE 3

Blast search of 3' flanking sequences against databases

| Database | G6 (%) | G9 (%) | G13 (%) | G17 (%) | G18 (%) | G23 (%) | G27 (%) |
|---|---|---|---|---|---|---|---|
| Nr | 57 (pig) | 73 (hum) | 86 (pig) | | 51 (pig) | 60 (pig) | 41 (pig) |
| Dbests | 54 (pig) | | 40 (pig) | | | 57 (hum) | 31 (pig) |
| Dbsts | 26 (pig) | | 31 (pig) | | | | 22 (pig) |
| Mouse ests | | | | | | | |
| Human ests | 54 (hum) | | 43 (hum) | | | 57 (hum) | 40 (hum) |
| Other ests | 55 (pig) | | 46 (pig) | | | | 31 (pig) |
| Pdb | | | | | | | |
| Patents | 55 | | | | | | 33 |
| Epd | | | | | | | |
| Gss | | | 32 (hum) | | | | |
| Htgs | | 73 (hum) | 40 (hum) | 62 (hum) | | | |
| probe length (bp) | 288 | 465 | 292 | 534 | 396 | 415 | 383 |
| Comments | SINE | | L1 repeat | | Pig male-specific repeat 1 | Pig centromeric repeat region | SINE |

Example 2

Cloning of a Unique 3' Flanking Sequence, G3–25 (SEQ ID NO:8)

The following illustrates how one skilled in the art would make or obtain a PERV clone having a unique 3' flanking sequence. Given the following description and teachings, one skilled in the art can apply the following methods to obtain any PERV clone described herein and is not intended to be limited to isolation of a specific PERV clone. A lambda library was constructed as described in Example 1. A PERV clone was isolated from a lambda FIX II vector using the env-cons probe (SEQ ID NO:1). In order to distinguish a 3' flanking sequence as distinct and unique (i.e. as a PERV locus), the PERV lambda clone was amplified using the primer pairs env5(2) and T3 or T7 (see FIG. 8) in order to generate a product corresponding from the end of the env region of PERV to porcine genomic sequence flanking the 3' region of PERV LTR. The purified PCR product was then sequenced with the LTR530 (located 100 bp upstream from the end of PERV LTR) oligonucleotide and based on the resulting 3' flanking sequence, a primer pair specific for the G3 locus was designed. The primer pair (5'G3(SEQ ID NO:40)/3'G3 (SEQ ID NO:41)) was used to amplify the G3 probe.

The G3–25 clone, containing a unique 3' flanking sequence suitable for identification of potentially infectious PERV, was then subcloned into a pZerO-2 vector (Invitrogen, Calif.) at the vector's Not I site (FIG. 10). The pZerO-2 vector's backbone was modified with a neomycin gene inserted at the vector's StuI site (FIG. 10), thereby allowing for selection of those plasmids containing a G3–25 clone insert.

Once subcloned, G3–25 containing plasmids were transfected into human 293 cells (ATCC: CRL-1573) and positive transfectants obtained following G418 selection. Supernatant from the 293 cells containing a G3–25 clone was then co-cultured with hygromycin resistant 293 cells (Hyg") and grown under hygromycin selection.

Example 3

Cloning of a Unique 3' Flanking Sequence, G19-A45 (SEQ ID NO:24)

The following illustrates how one skilled in the art would make or obtain a PERV clone having a unique 3' flanking sequence. Given the following description and teachings, one skilled in the art can apply the following methods to obtain any PERV clone described herein and is not intended to be limited to isolation of a specific PERV clone. A lambda library was constructed as described in Example 1. A PERV clone was isolated from a lambda FIX II vector using the PERV-A probe (SEQ ID NO:4). In order to distinguish a 3' flanking sequence as distinct and unique (i.e. as a PERV locus), the PERV lambda clone was amplified using the primer pairs env5(2) and T3 or T7 (see FIG. 8) in order to generate a product corresponding from the end of the env region of PERV to porcine genomic sequence flanking the 3' region of PERV LTR. The purified PCR product was then sequenced with the LTR530 (located 100 bp upstream from the end of PERV LTR) oligonucleotide and based on the resulting 3' flanking sequence, a primer pair specific for the G19 locus was designed. This primer pair (5'G19 (SEQ ID NO:72)/3'G19 9SEQ ID NO:73)) was used to amplify the G19-A45 probe.

The G19-A45 clone, containing a unique 3' flanking sequence suitable for identification of potentially infectious PERV, was then subcloned into a pZerO-2 vector (Invitrogen, Calif.) at the vector's Not I site (FIG. 10). The pZerO-2 vector's backbone was modified with a neomycin gene inserted at the vector's StuI site (FIG. 10), thereby allowing for selection of those plasmids containing a G19-A45 clone insert.

Once subcloned, G19-A45 containing plasmids were transfected into human 293 cells (ATCC: CRL-1573) and positive transfectants obtained following G418 selection. Supernatant from the 293 cells containing a G19-A45 clone was then co-cultured with hygromycin resistant 293 cells (Hyg$^r$) and grown under hygromycin selection.

Example 4

Cloning of a Unique 3' Flanking Sequence, G28-402A (SEQ ID NO:33)

The following illustrates how one skilled in the art would make or obtain a PERV clone having a unique 3' flanking sequence. Given the following description and teachings, one skilled in the art can apply the following methods to obtain any PERV clone described herein and is not intended to be limited to isolation of a specific PERV clone. A lambda library was constructed as described in Example 1. A PERV clone was isolated from a lambda FIX II vector using the PERV-A probe (SEQ ID NO:4). In order to distinguish a 3' flanking sequence as distinct and unique (i.e. as a PERV locus), the PERV lambda clone was amplified using the primer pairs env5(2) and T3 or T7 (see FIG. 10) in order to generate a product corresponding from the end of the env region of PERV to porcine genomic sequence flanking the 3' region of PERV LTR. The purified PCR product was then sequenced with the LTR530 (located 100 bp upstream from the end of PERV LTR) oligonucleotide and based on the resulting 3' flanking sequence, a primer pair specific for the G28 locus was designed. This primer pair (5'G28 (SEQ ID NO:90)/3'G28 (SEQ ID NO 91):) was used to amplify the G28-402A probe.

The G28-402A clone, containing a unique 3' flanking sequence suitable for identification of potentially infectious PERV, was then subcloned into a pZerO-2 vector (Invitrogen, Calif.) at the vector's Not I site (FIG. 10). The pZerO-2 vector's backbone was modified with a neomycin gene inserted at the vector's StuI site (FIG. 10), thereby allowing for selection of those plasmids containing a G28-402A clone insert.

Once subcloned, G28-402A containing plasmids were transfected into human 293 cells (ATCC: CRL-1573) and positive transfectants obtained following G418 selection. Supernatant from the 293 cells containing a G28-402A clone was then co-cultured with hygromycin resistant 293 cells (Hyg$^r$) and grown under hygromycin selection.

Example 5

PCR Analysis to Identify Allele Polymorphism of PERV Loci

A method to determine the existence of an allele containing or missing a specific PERV integration includes use of PCR analysis. Pig genomic DNA is analyzed with specific primers, which flank a particular PERV locus. Referring to FIG. 3, specific primer pairs used are notated as Gn-5'/3'-Gn; "n" refers to each specific PERV locus, which is identified by a number. In the case of an allele without the particular PERV integration, this primer pair will amplify a DNA product of approximately 200–400 bp in size. In a sample containing an allele, which carries the particular PERV integration, the PCR reaction will fail under normal conditions. This is because the projected PCR product is approximately 9 Kb (a size too large for successful amplification under the PCR conditions used). The smaller amplification product (200–400 bp) was sequenced. Sequence analysis of the smaller PCR product revealed the locus-specific integration site. Results of an exemplary analysis for allele polymorphism of the G3 (SEQ ID NO:8) and G19 (SEQ ID NO:24) PERV loci are shown in FIG. 5. Results of an exemplary analysis for allele polymorphism of the G28 (SEQ ID NO:33) locus are shown in FIG. 7.

Referring to FIG. 5, primer pairs that flank the G19-A45 (SEQ ID NO:25) locus are run with each sample as an internal control and results are shown in the top row of FIG. 5. The lower portion of FIG. 5 depicts a map indicating location of the oligonucleotide primers. As shown in the second row of the table contained in the upper region of FIG. 5, a PCR product from primer pair G19-5'/3'G19, (forward primer=5' end of the PERV gene; reverse primer=3' end of a unique 3'-flanking sequence) indicates absence of PERV-G19 on at least one allele. Results of PCR analysis using the Env5(2)/3'G19 primers (forward primer=within 3' end of PERV gene; reverse primer=3' end of unique 3'-flanking sequence) are also shown in FIG. 5 (middle region). Presence of a PCR product signifies that at least one allele in the sample has PERV-G19.

Results of genotype analysis for allele polymorphism in a series of transgenic pigs is shown in the upper region of FIG. 5. As indicated in FIG. 5, genotype analysis of DNA from a total of 11 pigs indicated that genomic DNA from pigs P7665 and P7679 lacked potentially infectious PERV-G19 locus. Use of these pigs as breeders will allow selective breeding for generation of PERV-G19-free pigs for use as a source of xenotransplant donor tissue.

Example 6

Southern Blot Analysis to Identify Allele Polymorphism of PERV Loci

Another method to determine PERV loci allele polymorphism is by Southern blot analysis. Based upon the restriction map of each locus, a banding pattern can be predicted when the Southern blot is hybridized with a probe which recognizes each particular 3' flanking genomic region. A different banding pattern will emerge if PERV is present depending upon whether PERV is present on both alleles, on one allele, or on neither allele. The noted polymorphism could be due to sequence polymorphism at the site of the particular restriction enzyme used, or to PERV integration genetic polymorphism. This can be tested by using multiple restriction enzymes. An example of a Southern blot analysis used to identify the various allele polymorphisms for a specific PERV locus is shown in FIGS. 4 and 6.

Southern Blot Analysis Conditions:

Porcine genomic DNA was digested with various restriction enzymes, size-fractionated on agarose gels, and transferred to nylon membranes. After cross-linking, the membranes were pre-hybridized in hybridization buffer (1% bovine serum albumin, 1 mM EDTA, 0.5 M NaHPO$_4$, pH 7.2, 7% sodium dodeyl sulfate) for 2 hours at 65° C. Then fresh hybridization buffer containing $^{32}$P-labeled PERV probe was added and incubated overnight at 65° C. Probes were labeled with ($^{32}$P) dCTP using T7 QuickPrime (Pharmacia, Piscataway, N.J.) After hybridization, nylon membranes were washed at 65° C. once in 2×SSC/0.2% SDS, once in 0.2×SSC/0.2% SDS, and subjected to autoradiography overnight.

Restriction digest with HindIII will result in a 1.3 kb fragment when probed with the G3–25, 3'flanking probe (SEQ ID NO:8) if a PERV-G3 allele is present in the sample. A sample not containing a PERV-G3 allele will result in a 3 kb size fragment. FIG. 4 shows a Southern blot analysis using HindIII digestion and the G3–25 probe (SEQ ID NO:8). DNA in lanes 1,8, 9, 10, 11, and 12 contain PERV-G3 on both alleles (+/+). DNA in lanes 3, 6, and 7 do not contain PERV-G3 on either allele (−/−). DNA in lanes 2, 4, and 5 contain PERV-G3 on only one allele (±).

Results from a Southern blot analysis of the PERV G19 locus are shown in FIG. 6. Restriction digest with BamHI will result in a 2 kb fragment if a PERV allele is present. Absence of PERV G19 produces a 3 kb sized product. As indicated in FIG. 6, samples L26-3, L26-4, L26-5, 42-2, and 42-4 are homozygous negative (−/−) for the PERV G19locus. Animals 42-3 and 42-5 contain the PERV G19locus on one allele (+/−), while 42-1 has PERV-G19 on both alleles (+/+).

Results from PCR and Southern blot analysis of the PERV G28 locus are shown in FIG. 7. As shown in FIG. 7, genotype analysis of the PERV G28 locus indicate that pigs p7714, p7715 and p7721 are homozygous negative (−/−) for the PERV G28 locus. Animals p7348, p7710 and p7711 contain the PERV G28 locus on one allele (+/−).

These methods allow screening of individual pigs to identify pigs that have one or both alleles without a specific PERV integration, making it possible to breed pigs in order to generate offspring which do not contain PERV loci that have the potential to be infectious.

As indicated in the examples above, Southern blot and PCR analysis demonstrated that all three PERV loci exhibit allele polymorphisms. Therefore, the present invention allows for breeding pigs that are negative for G3, G19 and G28 PERV loci.

Deposit of Material

The following materials have been deposited with the American Type Culture Collection, 10801 University Blvd., Manassas, Va., 20110-2209, USA (ATCC):

| Material | ATCC Deposit No. | Deposit Date |
| --- | --- | --- |
| Plasmid DNA (G3-25) | | Mar. 20, 2001 |
| Plasmid DNA (G19-A45) | | Mar. 20, 2001 |
| Plasmid DNA (G28-402A) | | Mar. 20, 2001 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Nextran, Inc. and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present invention is not to be limited in scope by the construct(s) deposited, since the deposited embodiment(s) is/are intended as single illustration(s) of certain aspects of the invention and any constructs that are functionally equivalent are within the scope of this invention. The deposit of material(s) herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

This application contains reference to numerous publications and patents, each of which is hereby incorporated, by reference in their entirety.

We claim:

1. A method for providing a pig whose genome is homozygous negative for at least two porcine endogenous retroviruses (PERV) loci selected from the group consisting of a G3 locus, a G19 locus, and a G28 locus, the method comprising:
   determining in a plurality of pigs whether their genomes are homozygous negative, homozygous positive or heterozygous for each of at least two PERV loci selected from the group consisting of a G3 locus, a G19 locus, and a G28 locus;
   selecting a first pig and a second pig from said plurality of pigs wherein the genome of said first pig is either homozygous negative or heterozygous for a first PERV locus selected from the group consisting of a G3 locus, a G19 locus, and a G28 locus and the genome of said second pig is either homozygous negative or heterozygous for a second PERV locus selected from the group consisting of a G3 locus, a G19 locus, and a G28 locus; and
   breeding said first pig and said second pig for one or more generations to produce a progeny whose genome is homozygous negative for both said first and said second PERV loci.

2. The method of claim 1, wherein the genome of said first pig is homozygous negative for said first PERV locus and the genome of said second pig is homozygous negative for said second PERV locus.

3. A method for providing a pig whose genome is homozygous negative for a PERV locus selected from a G3 locus, a G19 locus, or a G28 locus, the method comprising:
   determining in one or more pigs for a PERV locus selected from a G3 locus, a G19 locus, or a G28 locus whether each genome of said one or more pigs is homozygous negative, homozygous positive or heterozygous for said PERV locus;
   selecting a pig whose genome is either homozygous negative or heterozygous for said PERV locus from said one or more pigs; and
   breeding said selected pig and a second pig for one or more generations to produce a progeny whose genome is homozygous negative for said PERV locus.

4. The method of claim 3 wherein the genomes of both the selected pig and the second pig are homozygous negative for the PERV locus.

* * * * *